US007880002B2

(12) United States Patent
Carson et al.

(10) Patent No.: US 7,880,002 B2
(45) Date of Patent: Feb. 1, 2011

(54) SUBSTITUTED PIPERAZINYL-PYRROLIDINE COMPOUNDS USEFUL AS CHEMOKINE RECEPTOR ANTAGONISTS

(75) Inventors: Kenneth G. Carson, Princeton, NJ (US); Prakash Raman, Acton, MA (US); Francois Soucy, Stoneham, MA (US); Qing Ye, Westborough, MA (US); Shomir Ghosh, Brookline, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 1227 days.

(21) Appl. No.: 11/320,414

(22) Filed: Dec. 28, 2005

(65) Prior Publication Data

US 2006/0172994 A1    Aug. 3, 2006

Related U.S. Application Data

(60) Provisional application No. 60/639,912, filed on Dec. 29, 2004.

(51) Int. Cl.
C07D 403/00 (2006.01)
A61K 31/497 (2006.01)
(52) U.S. Cl. .................. 544/372; 514/254.02
(58) Field of Classification Search ......... 544/372; 514/254.02
See application file for complete search history.

(56) References Cited

U.S. PATENT DOCUMENTS

| | | | |
|---|---|---|---|
| 3,265,698 A | 8/1966 | Allen, Jr. et al. | |
| 5,338,852 A | 8/1994 | Efange et al. | |
| 5,756,508 A | 5/1998 | Thompson et al. | |
| 5,773,442 A | 6/1998 | Akamatsu et al. | |
| 5,789,420 A | 8/1998 | Efange et al. | |
| 5,876,694 A | 3/1999 | Efange et al. | |
| 5,985,878 A | 11/1999 | Stokbroekx et al. | |
| 6,057,324 A | 5/2000 | Matsumoto et al. | |
| 6,166,037 A | 12/2000 | Budhu et al. | |
| 6,391,865 B1 * | 5/2002 | Baroudy et al. | 514/63 |
| 6,642,226 B2 | 11/2003 | Kolczewski et al. | |
| 6,906,072 B1 | 6/2005 | Yamamoto et al. | |
| 6,930,104 B2 | 8/2005 | Kakihana et al. | |
| 6,977,265 B2 | 12/2005 | Du Bois et al. | |
| 7,291,618 B2 | 11/2007 | Hulin et al. | |
| 2002/0151547 A1 | 10/2002 | Kolczewski et al. | |
| 2003/0229121 A1 | 12/2003 | Du Bois et al. | |
| 2004/0157850 A1 | 8/2004 | Kakihana et al. | |
| 2004/0186135 A1 | 9/2004 | Dolle et al. | |
| 2004/0220193 A1 | 11/2004 | Yamamoto et al. | |
| 2005/0137211 A1 | 6/2005 | Blanco et al. | |
| 2005/0256310 A1 | 11/2005 | Hulin et al. | |
| 2006/0040950 A1 | 2/2006 | Janssens et al. | |
| 2006/0079498 A1 | 4/2006 | Hulin et al. | |
| 2006/0084658 A1 | 4/2006 | Yamamoto et al. | |
| 2006/0128721 A1 | 6/2006 | Janssens et al. | |
| 2006/0167008 A1 | 7/2006 | Janssens et al. | |
| 2006/0189628 A1 | 8/2006 | Rosse et al. | |
| 2006/0217392 A1 | 9/2006 | Anilkumar et al. | |
| 2007/0021611 A1 | 1/2007 | McGuinness et al. | |
| 2007/0054919 A1 | 3/2007 | Rosenblum et al. | |
| 2007/0099897 A1 | 5/2007 | Hulin et al. | |
| 2007/0161664 A1 | 7/2007 | Hulin et al. | |

FOREIGN PATENT DOCUMENTS

| | | |
|---|---|---|
| EP | 0121972 A2 | 10/1984 |
| EP | 0542363 A2 | 5/1993 |
| EP | 0810215 A1 | 12/1997 |
| EP | 0905129 A1 | 3/1999 |
| EP | 1254895 A1 | 11/2002 |
| EP | 1382598 A1 | 1/2004 |
| GB | 1080680 | 8/1967 |
| JP | 43020190 | 8/1968 |
| WO | WO 93/10091 A2 | 5/1993 |
| WO | WO 93/24457 A1 | 12/1993 |
| WO | WO 97/16192 A1 | 5/1997 |
| WO | WO 97/26258 A1 | 7/1997 |
| WO | WO 99/09984 A1 | 3/1999 |
| WO | WO 00/66558 A1 | 11/2000 |
| WO | WO 02/062784 A1 | 8/2002 |
| WO | WO 02/079194 A1 | 10/2002 |
| WO | WO 03/004487 A1 | 1/2003 |
| WO | WO 03/020716 A1 | 3/2003 |
| WO | WO 03-031441 * | 4/2003 |
| WO | WO 03/033490 A1 | 4/2003 |

(Continued)

OTHER PUBLICATIONS

Sigma-Aldrich Chemical On-line Catalog—Halogenated Heterocycles, May 22, 2009.*

(Continued)

*Primary Examiner*—Rita J Desai
*Assistant Examiner*—John Mabry

(57) ABSTRACT

The present invention relates to compounds useful as Chemokine Receptor antagonists. Compounds of general formula I are provided:

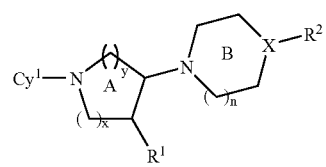

or pharmaceutically acceptable salts thereof. The invention also provides pharmaceutically acceptable compositions comprising said compounds and methods of using the compounds and compositions for the inhibition of Chemokine Receptors and also for the treatment of various diseases, conditions, or disorders, including acute or chronic inflammatory disease, cancer or osteolytic bone disorders.

17 Claims, No Drawings

FOREIGN PATENT DOCUMENTS

| WO | WO 03/045937 A1 | 6/2003 |
|---|---|---|
| WO | WO 2004/033428 A1 | 4/2004 |
| WO | WO 2004/056770 A2 | 7/2004 |
| WO | WO 2004/056772 A1 | 7/2004 |
| WO | WO 2004/056799 A2 | 7/2004 |
| WO | WO 2004/082623 A2 | 9/2004 |
| WO | WO 2004/110415 A2 | 12/2004 |
| WO | WO 2005/030188 A2 | 4/2005 |
| WO | WO 2005/101838 A2 | 10/2005 |
| WO | WO 2005/116014 A1 | 12/2005 |
| WO | WO 2006/008644 A1 | 1/2006 |
| WO | WO 2006/088840 A1 | 8/2006 |
| WO | WO 2006/088919 A2 | 8/2006 |
| WO | WO 2006/088921 A2 | 8/2006 |

OTHER PUBLICATIONS

F. Zaragoza Dorwald Side Reactions in Organic Synthesis 2005, Wiley-VCH.*

International Search Report dated Jun. 1, 2006 issued in PCT Application No. PCT/US05/047096, which corresponds to U.S. Appl. No. 11/320,414.

Assaad, Thaer, et al., "Synthesis and in vitro evaluation of N-substituted aza-trozamicol analogs as vesicular acetylcholine transporter ligands," *Bioorganic & Medicinal Chemistry Letters*, vol. 16, No. 10 (2006) pp. 2654-2657.

Coffeen, Paul R., et al., "Measurement of functional cholinergic innervation in rat heart with a novel vesamicol receptor ligand," *Nuclear Medicine & Biology*, vol. 23, No. 7 (1996) pp. 923-926.

Custers, Franciscus G. J., et al., "Vesamicol and some of its derivatives: Questionable ligands for selectively labelling acetylcholine transporters in rat brain," *European Journal of Pharmacology*, vol. 338, No. 2 (1997) pp. 177-183.

Efange, S.M.N., et al., "Nonsymmetrical bipiperidyls as inhibitors of vesicular acetylcholine storage," *Journal of Medicinal Chemistry*, vol. 36, No. 8 (1993) pp. 985-989.

Efange, S.M.N, et al., "Synthesis and tissue distribution of (m [$^{125}$I]iodobenzyl)trozamicol ([ $^{125}$I]MIBT): potential radioligand for mapping central cholinergic innervation," *Journal of Medicinal Chemistry*, vol. 36, No. 12 (1993) pp. 1754-1760.

Efange, S.M.N., et al., "p-[$^{18}$F]fluorobenzyltrozamicol ([$^{18}$F]FBT): molecular decomposition-reconstitution approach to vesamicol receptor radioligands for positron emission tomography," *Applied Radiation and Isotopes*, vol. 45, No. 4 (1994) pp. 465-472.

Efange, Simon M. N., et al., "Vesamicol analogues as sigma ligands," *Biochemical Pharmacology*, vol. 49, No. 6 (1995) pp. 791-797.

Efange, Simon M. N., et al., "Age-related diminution of dopamine antagonist-stimulated vesamicol receptor binding," *The Journal of Nuclear Medicine*, vol. 37, No. 7 (Jul. 1996) pp. 1192-1196.

Efange, Simon M. N., et al., "N-hydroxyalkyl derivatives of 3β-phenyltropane and 1-methylspirol[1H-indoline-3,4'-piperidine]: vesamicol analogues with affinity for monoamine transporters," *Journal of Medicinal Chemistry*, vol. 40, No. 24 (1997) pp. 3905-3914.

Efange, Simon M. N., et al., "The vesamicol receptor ligand (+)-meta-[$^{125}$I]iodobenzyltrozamicol {(+)-[$^{125}$I]-MIBT}reveals blunting of the striatal cholinergic response to dopamine D2 receptor blockade in the 6-hydroxydopamine (6-OHDA)-lesioned rat: possible implications for Parkinson's disease," *Life Sciences*, vol. 58, No. 16 (1996) pp. 1367-1374.

Efange, S.M.N., et al., "Vesicular acetylcholine transporter density and Alzheimer's disease," *Neurobiology of Aging*, vol. 18, No. 4 (1997) pp. 407-413.

Efange, S.M.N., et al., "(+)-p-([$^{18}$F]fluorobenzyl)spirotrozamicol {(+)-[$^{18}$F]spiro-FBT}: synthesis and biological evaluation of a high-affinity ligand for the vesicular acetylcholine transporter (VAChT)," *Nuclear Medicine & Biology*, vol. 26, No. 2 (1999) pp. 189-192.

Gage, H. Donald, et al., "Reproducibility of repeated measures of cholingeric terminal density using [$^{18}$F](+)-4-fluorobenzyltrozamicol and PET in the Rhesus monkey brain," *Journal of Nuclear Medicine*, vol. 41, No. 12 (2000) pp. 2069-2076.

Gage, H. Donald, et al., "Morphine-induced spinal cholinergic activation: in vivo imaging with positron emission tomography," *Pain*, vol. 91, No. 1-2 (2001) pp. 139-145.

Gaina, C., et al., "Polyimides containing 4,4'-bipyridinium units," *Journal of Applied Polymer Science*, vol. 94 (2004) pp. 2091-2100.

Hiessbock, Romana, et al., "Synthesis and in vitro multidrug resistance modulating activity of a series of dihydrobenzopyrans and tetrahydroquinolines," *Journal of Medicinal Chemistry*, vol. 42, No. 11 (1999) pp. 1921-1926.

Khare, A. B., et al., "N-(3-iodophenyl)trozamicol (IPHT) and related inhibitors of vesicular acetylcholine transport: synthesis and preliminary biological characterization," *Nuclear Medicine & Biology*, vol. 26, No. 6 (1999) pp. 609-617.

Mach, Robert H., et al., "Imaging of cholinergic terminals using the radiotracer [$^{18}$F](+)-4- fluorobenzyltrozamicol: in vitro binding studies and positron emission tomography studies in nonhuman primates," *Synapse*, vol. 25, No. 4 (1997) pp. 368-380.

Mach, Robert H., et al., "[$^{18}$F]4-fluorobenzyl iodide as a useful precursor in PET research: application in the development of dopaminergic and cholinergic radiotracers," *Synthesis and Applications of Isotopically Labelled Compounds*, vol. 8 Proceedings of the International Symposium, Boston, MA, USA, Jun. 1-5, 2003 (2004), meeting date 2003, pp. 183-186, editors: Dean, Dennis C., et al., publisher: John Wiley & Sons Ltd., Chichester, UK.

Staley, Julie K., et al., "Pharmacological characterization of the vesamicol analogue (+)-[$^{125}$I]MIBT in primate brain," *European Journal of Pharmacology*, vol. 338, No. 2 (1997) pp. 159-169.

Suero, Ruben, et al., "Synthesis of 3-aminopyrrolidines by cyclization of neutral C-centered α-aminoalkyl radicals," *Tetrahedron*, vol. 58, No. 31 (2002) pp. 6211-6221.

Sugiyama, Atsushi, et al., "Direct cardiac effects of a novel vesamicol receptor ligand, m-iodobenzyl-trozamicol, assessed in the canine isolated, blood-perfused heart preparations," *Journal of Cardiovascular Pharmacology*, vol. 34, No. 6 (1999) pp. 843-847.

Sugiyama, Atsushi, et al., "Effects of a novel vesamicol receptor ligand, m-(iodobenzyl)trozamicol, on the canine-isolated, blood-perfused atrioventricular node preparation," *Japanese Journal of Pharmacology*, vol. 82, No. 2 (2000) pp. 150-154.

"3-Piperidinepropanoic acid, 4-[4-(2-methoxyphenyl)-1-piperazinyl]-1-(phenylmethyl)-, ethyl ester (CA INDEX NAME)," CAS Registry No. 519018-38-3, entered May 22, 2003.

"3-Piperidinepropanoic acid, 4-[4-(2-fluorophenyl)-1-piperazinyl]-1-(phenylmethyl)-, ethyl ester (CA INDEX NAME)," CAS Registry No. 519018-37-2, entered May 22, 2003.

"2,5-Pyrrolidinedione, 3-[(4-chlorophenyl)thiol]-4-[4-[3-chloro-5-(trifluoromethyl)-2-pyridinyl]-1-piperazinyl]-1-(phenylmethyl)- (CA INDEX NAME)," CAS Registry No. 321433-54-9, entered Feb. 12, 2001.

International Search Report dated Jun. 1, 2006, issued in PCT Application No. PCT/US05/047327, which corresponds with U.S. Appl. No. 11/320,298 (U.S. Publication No. 2006/0189628 A1).

Chemical Abstract Services CAPLUS Database Abstract for JP 43020190 (B15).

* cited by examiner

SUBSTITUTED PIPERAZINYL-PYRROLIDINE COMPOUNDS USEFUL AS CHEMOKINE RECEPTOR ANTAGONISTS

PRIORITY INFORMATION

The present application claims priority under 35 U.S.C. §119(e) to U.S. Provisional Application No. 60/639,912, filed Dec. 29, 2004, entitled "Compounds Useful as Chemokine Receptor Antagonists", the entire contents of which are hereby incorporated by reference.

BACKGROUND OF THE INVENTION

Chemoattractant cytokines, Chemoattractant cytokines or chemokines are a family of proinflammatory mediators that are released by a wide variety of cells to promote recruitment and activation of cells such as T and B lymphocytes, eosinophils, basophils, and neutrophils (Luster et al. *New Eng. J. Med*, 1998, 338, 436). The chemokines are related in primary structure and contain four conserved cysteines, which form disulfide bonds. The chemokine family includes the C—X—C chemokines (α-chemokines), and the C—C chemokines (β-chemokines), in which the first two conserved cysteines are separated by an intervening residue, or are adjacent, respectively (Baggiolini, M. and Dahinden, C. A., *Immunology Today*, 1994, 15, 127).

Chemokines exert their biological activity by binding to specific cell-surface receptors belonging to the family of G-protein-coupled seven-transmembrane-domain proteins (Horuk, *Trends Pharm. Sci.* 1994, 15, 159) which are termed "chemokine receptors". On binding their cognate ligands, chemokine receptors then transduce signals important for the development and trafficking of specific leukocyte subsets (Baggiolini, et. al., *Nature* 1994, 15, 365). The chemokines and their cognate receptors have been implicated as being important mediators of inflammatory, and allergic diseases, disorders, and conditions, as well as autoimmune pathologies such as rheumatoid arthritis and atherosclerosis (see, Carter, *Current Opinion in Chemical Biology* 2002, 6, 510; Trivedi et al., *Ann. Reports Med. Chem.* 2000, 35, 191; Saunders et al., *Drug Disc. Today* 1999, 4, 80; and Premack et al., *Nature Medicine*, 1996, 2, 1174).

The first receptor for the C—C chemokines that was cloned and expressed binds the chemokines MIP-1α and RANTES. Accordingly, this MIP-1α/RANTES receptor was designated C—C chemokine receptor 1 (also referred to as CCR-1 or CKR-1; Neote, K., et al., *Cell*, 72:415-425 (1993); Horuk, R. et al., WO 94/11504, May 26, 1994; Gao, J.-I. et al., *J. Exp. Med.*, 177:1421-1427 (1993)). CCR1 also binds the chemokines CCL2 (MCP-1) CCL4 (MIP-1β), CCL7 (MCP-3), CCL8 (MCP-2), CCL13 (MCP-4), CCL14 (HCC-1), CCL15 (Lkn-1), CCL23 (MPIF-1). (Murphy P. M. et al., International Union of Pharmacology. XXII. Nomenclature for Chemokine Receptors, *Pharmacol. Reviews,* 52:145-176 (2000)).

Small molecule antagonists of the interaction between C—C chemokine receptors (e.g., CCR1) and their ligands, (e.g., CCL2 (MCP-1) CCL3 (MIP-1α), CCL4 (MIP-1β), CCL5 (RANTES), CCL7 (MCP-3), CCL8 (MCP-2), CCL13 (MCP-4), CCL14 (HCC-1), CCL15 (Lkn-1), or CCL23 (MPIF-1)), would inhibit those processes or cellular responses mediated by the binding of a chemokine to CCR1. Accordingly, these compounds would inhibit those pathogenic processes "triggered" by receptor ligand interactions (e.g., leukocyte migration, integrin activation, transient increases in the concentration of intracellular free calcium $[Ca^{++}]_i$, and/or granule release of proinflammatory mediators) and would be useful in the treatment of diseases, conditions, or disorders mediated by these pathogenic processes. Indeed, there has been substantial interest in the discovery and development of antagonists of CCR1 for a treatment of a variety of disorders including, but not limited to rheumatoid arthritis, multiple sclerosis, transplant rejection, and allergic inflammation (see, Cascieri et al., *Curr. Opin. Chem. Biol.* 2000, 4, 420; Onuffer et al., *Trends Pharmacol. Sci.* 2002, 23, 459; and Pease et al., *Expert Opin. Investig. Drugs* 2005, 14, 785). Additionally, studies have suggested that CCR1 antagonists would be useful for the treatment of cancer, including multiple myeloma, and for the treatment of other bone disorders resulting from the chemotactic and other responses of osteoclasts to the CC chemokine macrophage inflammatory protein (MIP-1α) (see, *Exp. Hematol.* 2005, 33, 272; *J. Clin. Invest.* 2001, 108, 1833; *Cancer* 2003, 97, 813; and *Blood* 2003, 102, 311 and references cited therein).

There remains a need, however, for the discovery and development of antagonists of CCR1 for use in the treatment of diseases, conditions, and disorders mediated by the interaction of chemokine receptors and their ligands.

SUMMARY OF THE INVENTION

It has now been found that compounds of this invention, and pharmaceutical compositions thereof, are effective as inhibitors of the interaction between chemokine receptors and their ligands. In some embodiments, these compounds are effective as inhibitors of CCR1.

These compounds have general formula I:

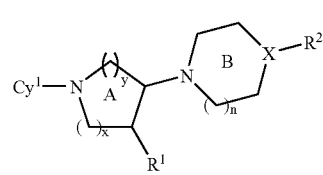

I or pharmaceutically acceptable salts thereof, wherein $R^1$, $R^2$, X, n, x, y, and $Cy^1$ are as defined generally and in subsets herein.

In general, these compounds, and pharmaceutical compositions thereof, are useful for treating or lessening the severity of a variety of acute or chronic inflammatory diseases, conditions, or disorders including, but not limited to, inflammatory arthritis, inflammatory demyelinating disease, chronic obstructive pulmonary disorder, atherosclerosis, arteriosclerosis, restenosis, ischemia/reperfusion injury, diabetes mellitus, psoriasis, inflammatory bowel diseases, rejection of a transplanted graft, graft versus host disease, allergy, or asthma. These compounds, and pharmaceutical compositions thereof, are also useful for treating cancer and osteolytic bone disorders.

In other embodiments, compounds of the invention are useful for treating diseases, conditions, or disorders characterized by pathogenic leukocyte recruitment, pathogenic leukocyte activation, or pathogenic leukocyte recruitment and activation.

DETAILED DESCRIPTION OF THE INVENTION

1. General Description of Compounds of the Invention

The present invention relates to a compound of formula I:

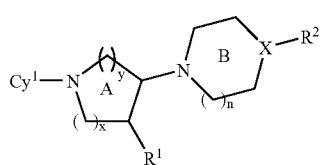

or a pharmaceutically acceptable salt thereof, wherein:

x and y are each independently 1 or 2, provided that x and y are not simultaneously 2;

$R^1$ is fluoro, —$R^3$, —$OR^4$, —$SR^4$, —$COOR^4$, —$COR^4$, —$CON(R^4)_2$, —$N(R^4)_2$, —$SO_2N(R^4)_2$, —$NR^4SO_2R^3$, —$NR^4COR^4$, $NR^4CON(R^4)_2$, —$CON(R^4)_2$, —$OCOR^4$, or —$OSO_2R^4$;

$R^3$ is an optionally substituted group selected from $C_1$-$C_6$aliphatic or a 3-7-membered saturated, partially unsaturated, or aromatic monocyclic ring having 0-3 heteroatoms independently selected from nitrogen, oxygen, or sulfur;

each occurrence of $R^4$ is independently hydrogen or an optionally substituted group selected from $C_1$-$C_6$aliphatic or a 3-7-membered saturated, partially unsaturated, or aromatic monocyclic ring having 0-3 heteroatoms independently selected from nitrogen, oxygen, or sulfur, or two $R^4$ on the same nitrogen atom, taken together with the nitrogen atom, form an optionally substituted 3-6-membered saturated, partially saturated, or aromatic ring having 0-2 additional heteroatoms independently selected from nitrogen, oxygen, or sulfur;

ring A is substituted with q occurrences of $R^A$, wherein q is 0-2 and each $R^A$ is independently halogen, —$SO_2N(R^C)_2$, —$OR^C$, —$SR^C$, —$SO_2R^C$, —$COR^C$, —$CO_2R^C$, —$N(R^C)_2$, —$CON(R^C)_2$, —$N(R^C)COR^C$, —$N(R^C)CO_2R^C$, —$N(R^C)CON(R^C)_2$, or an optionally substituted group selected from $C_1$-$C_6$aliphatic or a 3-7-membered saturated, partially unsaturated, or aromatic monocyclic ring having 0-3 heteroatoms independently selected from nitrogen, oxygen, or sulfur, or two occurrences of $R^A$, or $R^A$ and $R^1$, taken together with their intervening atom(s), form an optionally substituted spiro or fused 3-6-membered saturated or partially unsaturated ring having 0-3 heteroatoms independently selected from nitrogen, oxygen, or sulfur, wherein each $R^C$ is independently hydrogen or an optionally substituted group selected from $C_1$-$C_6$aliphatic or a 3-7-membered saturated, partially unsaturated, or aromatic monocyclic ring having 0-3 heteroatoms independently selected from nitrogen, oxygen, or sulfur, or two occurrences of $R^C$, taken together with the nitrogen atom to which they are bound, form an optionally substituted 3-6-membered saturated, partially unsaturated, or aromatic ring having 0-2 additional heteroatoms independently selected from nitrogen, oxygen, or sulfur;

ring B is substituted with r occurrences of —$R^B$ or -L-$R^B$, wherein r is 0-2, L is a straight or branched $C_{1-4}$ alkylene and each $R^B$ is independently halogen, —$OR^D$, —$SR^D$, $COR^D$, —$CO_2R^D$, —$N(R^D)_2$, —$CON(R^D)_2$, —$N(R^D)COR^D$, or an optionally substituted group selected from $C_1$-$C_6$aliphatic or a 3-7-membered saturated, partially unsaturated, or aromatic monocyclic ring having 0-3 heteroatoms independently selected from nitrogen, oxygen, or sulfur, or two occurrences of $R^B$, taken together with their intervening atom(s), form an optionally substituted spiro, fused or bridged 3-6-membered saturated, partially unsaturated, or aromatic ring having 0-3 heteroatoms independently selected from nitrogen, oxygen, or sulfur; wherein each $R^D$ is independently hydrogen or an optionally substituted group selected from $C_1$-$C_6$aliphatic or a 3-7-membered saturated, partially unsaturated, or aromatic monocyclic ring having 0-3 heteroatoms independently selected from nitrogen, oxygen, or sulfur, or two occurrences of $R^D$, taken together with the nitrogen atom to which they are bound, form an optionally substituted 3-6-membered saturated, partially unsaturated, or aromatic ring having 0-2 additional heteroatoms independently selected from nitrogen, oxygen, or sulfur;

n is 1 or 2;

$R^2$ is -T-$Cy^2$, or -$Cy^2$, wherein T, when present, is a $C_1$-$C_3$alkylene chain, wherein the alkylene chain is substituted with 0 or 1 occurrence of $R^{5a}$, and 0, 1, or 2 independent occurrences of $R^{5b}$, and wherein one or more methylene units in the $C_1$-$C_3$alkylene chain, as valency and stability permit, is optionally replaced by one or more independent occurrences of —$CR^{5c}$=$CR^{5c}$—, —CO—, —$SO_2$—, —O—, —S—, or —$NR^{5c}$—;

$R^{5a}$ is halogen, —CN, —$OR^{5c}$, —$N(R^{5c})_2$, —$SR^{5c}$, or an optionally substituted group selected from $C_1$-$C_6$aliphatic, or a 3-7-membered saturated, partially unsaturated, or aromatic monocyclic ring having 0-3 heteroatoms independently selected from nitrogen, oxygen, or sulfur;

$R^{5b}$ is an optionally substituted group selected from $C_1$-$C_6$aliphatic, or a 3-7-membered saturated, partially unsaturated, or aromatic monocyclic ring having 0-3 heteroatoms independently selected from nitrogen, oxygen, or sulfur;

$R^{5c}$ is hydrogen, or an optionally substituted group selected from $C_1$-$C_4$aliphatic, or a 3-7-membered saturated, partially unsaturated, or aromatic monocyclic ring having 0-3 heteroatoms independently selected from nitrogen, oxygen, or sulfur, or two occurrences of $R^{5c}$, taken together with the nitrogen atom to which they are bound, form an optionally substituted 3-6-membered saturated, partially unsaturated, or aromatic ring having 0-2 additional heteroatoms independently selected from nitrogen, oxygen, or sulfur;

$Cy^2$ is an optionally substituted group selected from a 3-7-membered saturated, partially unsaturated, or aromatic monocyclic ring having 0-3 heteroatoms independently selected from nitrogen, oxygen, or sulfur, or an 8-10-membered partially unsaturated, or aromatic bicyclic ring system having 0-5 heteroatoms independently selected from nitrogen, oxygen, or sulfur; wherein $Cy^2$ is substituted with m independent occurrences of —$R^{6a}$, -G-$R^{6a}$, or —V-G-$R^{6a}$, and k occurrences of =O, =S, =$NR^{7a}$, =$NR^{7b}$, —$R^{6b}$, -G-$R^{6b}$, or —V-G-$R^{6b}$, wherein:

m is 0-3;

k is 0-2;

V is —O—, —$N(R^{7a})$—, —S—, —SO—, —$SO_2$—, —$SO_2N(R^{7a})$—, —$N(R^{7a})SO_2$—, —CO—, —$CON(R^{7a})$—, —$N(R^{7a})CO$—, or —$CO_2$—;

G is an optionally substituted straight or branched $C_1$-$C_4$alkylene chain that is optionally replaced by —$CR^{7a}$=$CR^{7a}$—, —O—, —$N(R^{7a})$—, —S—, —SO—, —$SO_2$—, —$SO_2N(R^{7a})$—, —$N(R^{7a})SO_2$—, —CO—, —$CON(R^{7a})$—, —$N(R^{7a})CO$—, or —$CO_2$—, provided that the replacing moiety is not directly bonded to V, —$R^{6a}$, or —$R^{6b}$;

each —$R^{6a}$ is independently optionally substituted $C_1$-$C_6$ aliphatic, halogen, —$OR^{7a}$, —CN, —$NO_2$, —$SR^{7a}$, —$SO_2N(R^{7a})_2$, —$NR^{7a}SO_2R^{7a}$, —$SO_2R^{7a}$, —$COR^{7a}$, —$CO_2R^{7a}$, —N($R^{7a}$)$_2$, —CON($R^{7a}$)$_2$, —N($R^{7a}$)CO$R^{7a}$, —N($R^{7a}$)CO$_2R^{7a}$, or —N($R^{7a}$)CON($R^{7a}$)$_2$;

each —$R^{6b}$ is independently —O$R^{7b}$, —S$R^{7b}$, —SO$_2$N($R^{7b}$)($R^{7c}$), N$R^{7c}$SO$_2R^{7b}$, —SO$_2R^{7b}$, —CO$R^{7b}$, —CO$_2R^{7b}$, —N($R^{7b}$)($R^{7c}$), —CON($R^{7b}$)($R^{7c}$), —N($R^{7c}$)CO$R^{7b}$, —N($R^{7c}$)CO$_2R^{7b}$, —N($R^{7c}$)CON($R^{7b}$)($R^{7c}$), or an optionally substituted group selected from a 3-7-membered saturated, partially unsaturated, or aromatic monocyclic ring having 0-3 heteroatoms independently selected from nitrogen, oxygen, or sulfur, or an 8-10-membered saturated, partially unsaturated, or aromatic bicyclic ring system having 0-5 heteroatoms independently selected from nitrogen, oxygen, or sulfur; or two occurrences of $R^{6b}$, taken together with their intervening atom(s), form a spiro, fused, or bridged optionally substituted 5-7-membered saturated, partially unsaturated, or aromatic ring having 0-3 heteroatoms independently selected from nitrogen, oxygen, or sulfur;

each $R^{7a}$ is hydrogen or an optionally substituted $C_1$-$C_6$ aliphatic group;

each $R^{7b}$ is an optionally substituted group selected from a 3-7-membered saturated, partially unsaturated, or aromatic monocyclic ring having 0-3 heteroatoms independently selected from nitrogen, oxygen, or sulfur, or an 8-10-membered saturated, partially unsaturated, or aromatic bicyclic ring having 0-5 heteroatoms independently selected from nitrogen, oxygen, or sulfur; and each $R^{7c}$ is hydrogen or an optionally substituted group selected from a $C_1$-$C_6$ aliphatic group, a 3-7-membered saturated, partially unsaturated, or aromatic monocyclic ring having 0-3 heteroatoms independently selected from nitrogen, oxygen, or sulfur, or an 8-10-membered saturated, partially unsaturated, or aromatic bicyclic ring having 0-5 heteroatoms independently selected from nitrogen, oxygen, or sulfur; or $R^{7b}$ and $R^{7c}$, taken together with the nitrogen atom to which they are bound, form an optionally substituted 3-6-membered saturated, partially unsaturated, or aromatic ring having 0-2 additional heteroatoms independently selected from nitrogen, oxygen, or sulfur;

X is N or C$R^8$, wherein $R^8$ is halogen, —$R^9$, —O$R^9$, —N($R^9$)$_2$, —S$R^9$, —OCO$R^9$, —COO$R^9$, —CN, —CON($R^9$)$_2$, —CO$R^9$, —SO$_2R^9$, —SO$R^9$, —N$R^9$SO$_2R^9$, or —SO$_2$N($R^9$)$_2$, wherein each $R^9$ is independently hydrogen or an optionally substituted $C_1$-$C_6$ aliphatic group; or when X is C$R^8$, $R^8$ and $R^2$, taken together with the carbon atom to which they are bound, form an optionally substituted 3-6-membered spiro ring having 0-3 heteroatoms independently selected from nitrogen, oxygen, or sulfur;

Cy$^1$ is an optionally substituted group selected from a 5-8-membered partially unsaturated or aromatic unsaturated monocyclic ring having 0-3 heteroatoms independently selected from nitrogen, oxygen, or sulfur, or an 8-14-membered partially unsaturated or aromatic bicyclic or tricyclic ring system having 0-5 heteroatoms independently selected from nitrogen, oxygen, or sulfur; wherein Cy$^1$ is substituted with p independent occurrences of —$R^{10a}$, -J-$R^{10a}$, or W-J-$R^{10a}$, and j occurrences of =O, =S, =N$R^{11a}$, =N$R^{11b}$, —$R^{10b}$, -J-$R^{10b}$, or —W-J-$R^{10b}$, wherein:

p is 0-3;

j is 0-2;

W is —O—, —N($R^{11a}$)—, —S—, —SO—, —SO$_2$—, —SO$_2$N($R^{11a}$)—, —N($R^{11a}$)SO$_2$—, —CO—, —CON($R^{11a}$)—, —N($R^{11a}$)CO—, or —CO$_2$—;

J is an optionally substituted straight or branched $C_1$-$C_4$ alkylene chain that is optionally replaced by —C$R^{11a}$=C$R^{11a}$—, —O—, —N($R^{11a}$)—, —S—, —SO—, —SO$_2$—, —SO$_2$N($R^{11a}$)—, —N($R^{11a}$)SO$_2$—, —CO—, —CON($R^{11a}$)—, —N($R^{11a}$)CO—, or —CO$_2$—, provided that the replacing moiety is not directly bonded to W, —$R^{10a}$, or —$R^{10b}$;

each —$R^{10a}$ is independently optionally substituted $C_1$-$C_6$ aliphatic, halogen, —O$R^{11a}$, —CN, —NO$_2$, —S$R^{11a}$, —SO$_2$N($R^{11a}$)$_2$, —N$R^{11a}$SO$_2R^{11a}$, —SO$_2R^{11a}$, —CO$R^{11a}$, —CO$_2R^{11a}$, —N($R^{11a}$)$_2$, —CON($R^{11a}$)$_2$, —N($R^{11a}$)CO$R^{11a}$, —N($R^{11a}$)CO$_2R^{11a}$, or —N($R^{11a}$)CON($R^{11a}$)$_2$;

each —$R^{10b}$ is independently —O$R^{11b}$, —S$R^{11b}$, —SO$_2$N($R^{11b}$)($R^{11c}$), —N$R^{11c}$SO$_2R^{11b}$, —SO$_2R^{11b}$, —CO$R^{11b}$, —CO$_2R^{11b}$, —N($R^{11b}$)($R^{11c}$), —CON($R^{11b}$)($R^{11c}$), —N($R^{11c}$)CO$R^{11b}$, —N($R^{11c}$)CO$_2R^{11b}$, —N($R^{11c}$)CON($R^{11b}$)($R^{11c}$), or an optionally substituted group selected from a 3-7-membered saturated, partially unsaturated, or aromatic monocyclic ring having 0-3 heteroatoms independently selected from nitrogen, oxygen, or sulfur, or an 8-10-membered saturated, partially unsaturated, or aromatic bicyclic ring system having 0-5 heteroatoms independently selected from nitrogen, oxygen, or sulfur; or two occurrences of $R^{10b}$, taken together with their intervening atom(s), form a spiro, fused, or bridged optionally substituted 5-7-membered saturated, partially unsaturated, or aromatic ring having 0-3 heteroatoms independently selected from nitrogen, oxygen, or sulfur;

each $R^{11a}$ is hydrogen or an optionally substituted $C_1$-$C_6$ aliphatic group;

each $R^{11b}$ is an optionally substituted group selected from a 3-7-membered saturated, partially unsaturated, or aromatic monocyclic ring having 0-3 heteroatoms independently selected from nitrogen, oxygen, or sulfur, or an 8-10-membered saturated, partially unsaturated, or aromatic bicyclic ring having 0-5 heteroatoms independently selected from nitrogen, oxygen, or sulfur; and each $R^{11c}$ is hydrogen or an optionally substituted group selected from a $C_1$-$C_6$ aliphatic group, a 3-7-membered saturated, partially unsaturated, or aromatic monocyclic ring having 0-3 heteroatoms independently selected from nitrogen, oxygen, or sulfur, or an 8-10-membered saturated, partially unsaturated, or aromatic bicyclic ring having 0-5 heteroatoms independently selected from nitrogen, oxygen, or sulfur; or $R^{11b}$ and $R^{11c}$, taken together with the nitrogen atom to which they are bound, form an optionally substituted 3-6-membered saturated, partially unsaturated, or aromatic ring having 0-2 additional heteroatoms independently selected from nitrogen, oxygen, or sulfur.

In some embodiments of formula I one or both of the following conditions apply:

A) when ring A is

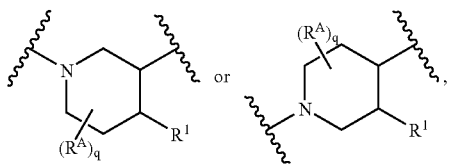

$R^1$ is OH, n is 1, q and r are 0, X is CH, and $R^2$ is unsubstituted phenyl, then Cy$^1$ is not unsubstituted phenyl or phenyl substituted with —Br, —I, —NO$_2$, or —NH$_2$; and B) when ring A is

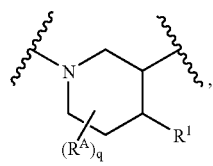

R¹ is OH, q and r are 0, X is N, and R² is (3-CF₃)phenyl-, then Cy¹ is not 6-(3-methyl-1,2,4-thiadiazol-5-yl)-3-pyridazinyl.

2. Compounds and Definitions

Compounds of this invention include those described generally above, and are further illustrated by the classes, subclasses, and species disclosed herein. As used herein, the following definitions shall apply unless otherwise indicated.

As described herein, compounds of the invention may be optionally substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which hydrogen atom can be replaced with the radical of a suitable substituent. Unless otherwise indicated, an "optionally substituted" group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

A stable compound or chemically feasible compound is one in which the chemical structure is not substantially altered when kept at a temperature from about −80° C. to about +40°, in the absence of moisture or other chemically reactive conditions, for at least a week, or a compound which maintains its integrity long enough to be useful for therapeutic or prophylactic administration to a patient. The phrase "one or more substituents", as used herein, refers to a number of substituents that equals from one to the maximum number of substituents possible based on the number of available bonding sites, provided that the above conditions of stability and chemical feasibility are met.

As used herein, the term "independently selected" means that the same or different values may be selected for multiple instances of a given variable in a single compound. By way of example, in a compound of formula (I), if Ring B is substituted with two substituents —R$^b$, each substituent is selected from the group of defined values for R$^b$, and the two values selected may be the same or different.

As used herein, "a 3-7-membered saturated, partially unsaturated, or aromatic monocyclic ring having 0-3 heteroatoms independently selected from nitrogen, oxygen, or sulfur, or an 8-10-membered partially unsaturated, or aromatic bicyclic ring system having 0-5 heteroatoms independently selected from nitrogen, oxygen, or sulfur" includes cycloaliphatic, heterocyclic, aryl and heteroaryl rings.

As used herein, the term "aromatic" includes aryl and heteroaryl groups as described generally below and herein.

The term "aliphatic" or "aliphatic group", as used herein, means an optionally substituted straight-chain or branched $C_{1-12}$ hydrocarbon, or a cyclic $C_{1-12}$ hydrocarbon which is completely saturated or which contains one or more units of unsaturation, but which is not aromatic (also referred to herein as "carbocycle", "cycloaliphatic", "cycloalkyl", or "cycloalkenyl"). For example, suitable aliphatic groups include optionally substituted linear, branched or cyclic alkyl, alkenyl, alkynyl groups and hybrids thereof, such as (cycloalkyl)alkyl, (cycloalkenyl)alkyl, or (cycloalkyl)alkenyl. Unless otherwise specified, in various embodiments, aliphatic groups have 1-12, 1-10, 1-8, 1-6, 1-4, 1-3, or 1-2 carbon atoms.

The term "alkyl", used alone or as part of a larger moiety, refers to an optionally substituted straight or branched chain hydrocarbon group having 1-12, 1-10, 1-8, 1-6, 1-4, 1-3, or 1-2 carbon atoms.

The term "alkenyl", used alone or as part of a larger moiety, refers to an optionally substituted straight or branched chain hydrocarbon group having at least one double bond and having 2-12, 2-10, 2-8, 2-6, 2-4, or 2-3 carbon atoms.

The term "alkynyl", used alone or as part of a larger moiety, refers to an optionally substituted straight or branched chain hydrocarbon group having at least one triple bond and having 2-12, 2-10, 2-8, 2-6, 2-4, or 2-3 carbon atoms.

The terms "cycloaliphatic", "carbocycle", "carbocyclyl", "carbocyclo", or "carbocyclic", used alone or as part of a larger moiety, refer to an optionally substituted saturated or partially unsaturated cyclic aliphatic ring system having from 3 to about 14 ring carbon atoms. In some embodiments, the cycloaliphatic group is an optionally substituted monocyclic hydrocarbon having 3-8 or 3-6 ring carbon atoms. Cycloaliphatic groups include, without limitation, optionally substituted cyclopropyl, cyclobutyl, cyclopentyl, cyclopentenyl, cyclohexyl, cyclohexenyl, cycloheptyl, cycloheptenyl, cyclooctyl, cyclooctenyl, or cyclooctadienyl. The terms terms "cycloaliphatic", "carbocycle", "carbocyclyl", "carbocyclo", or "carbocyclic" also include optionally substituted bridged or fused bicyclic rings having 6-12, 6-10, or 6-8 ring carbon atoms, wherein any individual ring in the bicyclic system has 3-8 ring carbon atoms.

The term "cycloalkyl" refers to an optionally substituted saturated ring system of about 3 to about 10 ring carbon atoms. Exemplary monocyclic cycloalkyl rings include cyclopropyl, cyclobutyl, cyclopentyl, cyclohexyl, and cycloheptyl.

The term "cycloalkenyl" refers to an optionally substituted non-aromatic monocyclic or multicyclic ring system containing at least one carbon-carbon double bond and having about 3 to about 10 carbon atoms. Exemplary monocyclic cycloalkenyl rings include cyclopentyl, cyclohexenyl, and cycloheptenyl.

The terms "haloaliphatic", "haloalkyl", "haloalkenyl" and "haloalkoxy" refer to an aliphatic, alkyl, alkenyl or alkoxy group, as the case may be, which is substituted with one or more halogen atoms. As used herein, the term "halogen" or "halo" means F, Cl, Br, or I. The term "fluoroaliphatic" refers to a haloaliphatic wherein the halogen is fluoro, including perfluorinated aliphatic groups. Examples of fluoroaliphatic groups include, without limitation, fluoromethyl, difluoromethyl, trifluoromethyl, 2-fluoroethyl, 2,2,2-trifluoroethyl, 1,1, 2-trifluoroethyl, 1,2,2-trifluoroethyl, and pentafluoroethyl.

The term "heteroatom" refers to one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The terms "aryl" and "ar-", used alone or as part of a larger moiety, e.g., "aralkyl", "aralkoxy", or "aryloxyalkyl", refer to an optionally substituted $C_{6-14}$ aromatic hydrocarbon moiety comprising one to three aromatic rings. Preferably, the aryl group is a $C_{6-10}$ aryl group. Aryl groups include, without limitation, optionally substituted phenyl, naphthyl, or anthracenyl. The terms "aryl" and "ar-", as used herein, also include groups in which an aryl ring is fused to one or more cycloaliphatic rings to form an optionally substituted cyclic structure such as a tetrahydronaphthyl, indenyl, or indanyl ring. The term "aryl" may be used interchangeably with the terms "aryl group", "aryl ring", and "aromatic ring".

An "aralkyl" or "arylalkyl" group comprises an aryl group covalently attached to an alkyl group, either of which independently is optionally substituted. Preferably, the aralkyl group is $C_{6-10}$ aryl $C_{1-6}$ alkyl, including, without limitation, benzyl, phenethyl, and naphthylmethyl.

The terms "heteroaryl" and "heteroar-", used alone or as part of a larger moiety, e.g., "heteroaralkyl", or "heteroaralkoxy", refer to groups having 5 to 14 ring atoms, preferably 5, 6, 9, or 10 ring atoms; having 6, 10, or 14 π electrons shared in a cyclic array; and having, in addition to carbon atoms, from one to five heteroatoms. A heteroaryl group may be mono-, bi-, tri-, or polycyclic, preferably mono-, bi-, or tricyclic, more preferably mono- or bicyclic. The term "heteroatom" refers to nitrogen, oxygen, or sulfur, and includes any oxidized form of nitrogen or sulfur, and any quaternized form of a basic nitrogen. For example, a nitrogen atom of a heteroaryl may be a basic nitrogen atom and may also be optionally oxidized to the corresponding N-oxide. When a heteroaryl is substituted by a hydroxy group, it also includes its corresponding tautomer. The terms "heteroaryl" and "heteroar-", as used herein, also include groups in which a heteroaromatic ring is fused to one or more aryl, cycloaliphatic, or heterocycloaliphatic rings. Nonlimiting examples of heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 3- to 8-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or NR$^+$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, piperidinyl, decahydroquinolinyl, oxazolidinyl, piperazinyl, dioxanyl, dioxolanyl, diazepinyl, oxazepinyl, thiazepinyl, morpholinyl, and thiamorpholinyl. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted. Additionally, a heterocyclic ring also includes groups in which the heterocyclic ring is fused to one or more aryl rings.

As used herein, the term "partially unsaturated" refers to a ring moiety that includes at least one double or triple bond between ring atoms. The term "partially unsaturated" is intended to encompass rings having multiple sites of unsaturation, but is not intended to include aromatic (e.g., aryl or heteroaryl) moieties, as herein defined.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. An optionally substituted alkylene chain is a polymethylene group in which one or more methylene hydrogen atoms is optionally replaced with a substituent. Suitable substituents include those described below for a substituted aliphatic group and also include those described in the specification herein.

An alkylene chain also can be optionally replaced by a functional group. An alkylene chain is "replaced" by a functional group when an internal methylene unit is replaced with the functional group. Examples of suitable "replacing functional groups" are described in the specification and claims herein.

For purposes of clarity, all bivalent groups described herein, including, e.g., the alkylene chain linkers described above, are intended to be read from left to right, with a corresponding left-to-right reading of the formula or structure in which the variable appears.

An aryl (including aralkyl, aralkoxy, aryloxyalkyl and the like) or heteroaryl (including heteroaralkyl and heteroaralkoxy and the like) group may contain one or more substituents and thus may be "optionally substituted". In addition to the substituents defined above and herein, suitable substituents on the unsaturated carbon atom of an aryl or heteroaryl group also include and are generally selected from -halo, —NO$_2$, —CN, —R$^+$, —C(R$^+$)=C(R$^+$)$_2$, —C≡C—R$^+$, —OR$^+$, —SR$^o$, —S(O)R$^o$, —SO$_2$R$^o$, —SO$_3$R$^+$, —SO$_2$N(R$^+$)$_2$, —N(R$^+$)$_2$, —NR$^+$C(O)R$^+$, —NR$^+$C(S)R$^+$, —NR$^+$C(O)N(R$^+$)$_2$, —NR$^+$C(S)N(R$^+$)$_2$, —N(R$^+$)C(=NR$^+$)—N(R$^+$)$_2$, —N(R$^+$)C(=NR$^+$)—R$^o$, —NR$^+$CO$_2$R$^+$, —NR$^+$SO$_2$R$^o$, —NR$^+$SO$_2$N(R$^+$)$_2$, —O—C(O)R$^+$, —O—CO$_2$R$^+$, —OC(O)N(R$^+$)$_2$, —C(O)R$^+$, —C(S)R$^o$, —CO$_2$R$^+$, —C(O)—C(O)R$^+$, —C(O)N(R$^+$)$_2$, —C(S)N(R$^+$)$_2$, —C(O)N(R$^+$)—OR$^+$, —C(O)N(R$^+$)C(=NR$^+$)—N(R$^+$)$_2$, —N(R$^+$)C(=NR$^+$)—N(R$^+$)—C(O)R$^+$, —C(=NR$^+$)—N(R$^+$)$_2$, —C(=NR$^+$)—OR$^+$, —N(R$^+$)—N(R$^+$)$_2$, —C(=NR$^+$)—N(R$^+$)—OR$^+$, —C(R$^o$)=N—OR$^+$, —P(O)(R$^+$)$_2$, —P(O)(OR$^+$)$_2$, —O—P(O)—OR$^+$, and —P(O)(NR$^+$)—N(R$^+$)$_2$, wherein R⁺, independently, is hydrogen or an optionally substituted aliphatic, aryl, heteroaryl, cycloaliphatic, or heterocyclyl group, or two independent occurrences of R⁺ are taken together with their intervening atom(s) to form an optionally substituted 5-7-membered aryl, heteroaryl, cycloaliphatic, or heterocyclyl ring. Each R° is an optionally substituted aliphatic, aryl, heteroaryl, cycloaliphatic, or heterocyclyl group.

An aliphatic or heteroaliphatic group, or a non-aromatic carbycyclic or heterocyclic ring may contain one or more substituents and thus may be "optionally substituted". Unless otherwise defined above and herein, suitable substituents on the saturated carbon of an aliphatic or heteroaliphatic group, or of a non-aromatic carbocyclic or heterocyclic ring are selected from those listed above for the unsaturated carbon of an aryl or heteroaryl group and additionally include the following: =O, =S, =C(R*)₂, =N—N(R*)₂, =N—OR*, =N—NHC(O)R*, =N—NHCO₂R°=N—NHSO₂R° or =N—R* where R° is defined above, and each R* is independently selected from hydrogen or an optionally substituted C₁₋₆ aliphatic group.

In addition to the substituents defined above and herein, optional substituents on the nitrogen of a non-aromatic heterocyclic ring also include and are generally selected from —R⁺, —N(R⁺)₂, —C(O)R⁺, —C(O)OR⁺, —C(O)C(O)R⁺, —C(O)CH₂C(O)R⁺, —S(O)₂R⁺, —S(O)₂N(R³⁰)₂, —C(S)N(R⁺)₂, —C(=NH)—N(R⁺)₂, or —N(R⁺)S(O)₂R⁺; wherein each R⁺ is defined above. A ring nitrogen atom of a heteroaryl or non-aromatic heterocyclic ring also may be oxidized to form the corresponding N-hydroxy or N-oxide compound. A nonlimiting example of such a heteroaryl having an oxidized ring nitrogen atom is N-oxidopyridyl.

As detailed above, in some embodiments, two independent occurrences of R⁺ (or any other variable similarly defined in the specification and claims herein), are taken together with their intervening atom(s) to form a monocyclic or bicyclic ring selected from 3-13-membered cycloaliphatic, 3-12-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

Exemplary rings that are formed when two independent occurrences of R⁺ (or any other variable similarly defined in the specification and claims herein), are taken together with their intervening atom(s) include, but are not limited to the following: a) two independent occurrences of R⁺ (or any other variable similarly defined in the specification or claims herein) that are bound to the same atom and are taken together with that atom to form a ring, for example, N(R⁺)₂, where both occurrences of R⁺ are taken together with the nitrogen atom to form a piperidin-1-yl, piperazin-1-yl, or morpholin-4-yl group; and b) two independent occurrences of R⁺ (or any other variable similarly defined in the specification or claims herein) that are bound to different atoms and are taken together with both of those atoms to form a ring, for example where a phenyl group is substituted with two occurrences of OR⁺

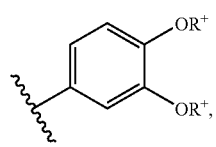

these two occurrences of R⁺ are taken together with the oxygen atoms to which they are bound to form a fused 6-membered oxygen containing ring:

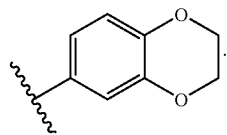

It will be appreciated that a variety of other rings (e.g., spiro and bridged rings) can be formed when two independent occurrences of R⁺ (or any other variable similarly defined in the specification and claims herein) are taken together with their intervening atom(s) and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a ¹³C- or ¹⁴C-enriched carbon are within the scope of this invention. Such compounds are useful, for example, as analytical tools or probes in biological assays.

It is to be understood that, when a disclosed compound has at least one chiral center, the present invention encompasses one enantiomer of inhibitor free from the corresponding optical isomer, racemic mixture of the inhibitor and mixtures enriched in one enantiomer relative to its corresponding optical isomer. When a mixture is enriched in one enantiomer relative to its optical isomers, the mixture contains, for example, an enantiomeric excess of at least 50%, 75%, 90%, 95% 99% or 99.5%.

The enantiomers of the present invention may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. Where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a disclosed compound has at least two chiral centers, the present invention encompasses a diastereomer free of other diastereomers, a pair of diastereomers free from other diastereomeric pairs, mixtures of diasteromers, mistures of diasteromeric pairs, mixtures of diasteromers in which one diastereomer is enriched relative to the other diastereomer(s) and mixtures of diasteromeric pairs in which one diastereomeric pair is enriched relative to the other diastereomeric pair(s). When a mixture is enriched in one diastereomer or diastereomeric pair(s) relative to the other diastereomers or diastereomeric pair(s), the mixture is enriched with the depicted or referenced diastereomer or diastereomeric pair(s) relative to other diastereomers or diastereomeric pair(s) for the compound, for example, by a molar excess of at least 50%, 75%, 90%, 95% 99% or 99.5%.

The diastereoisomeric pairs may be separated by methods known to those skilled in the art, for example chromatography or crystallization and the individual enantiomers within each pair may be separated as described above. Specific procedures for chromatographically separating diastereomeric pairs of precursors used in the preparation of compounds disclosed herein are provided the examples herein.

3. Description of Exemplary Compounds

This invention provides, inter alia, compounds of any one of formulae II, III, or IV:

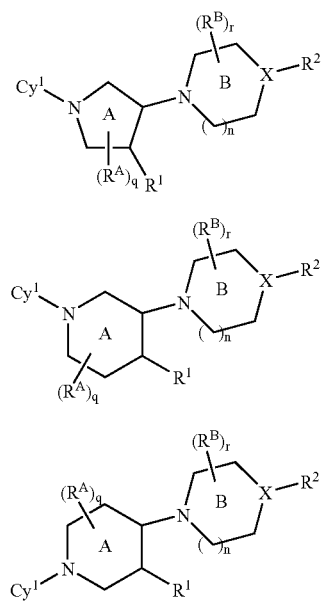

In certain embodiments of formulae II, III, and IV, n is 1 and compounds of any one of formulae II-A, III-A, or IV-A are provided:

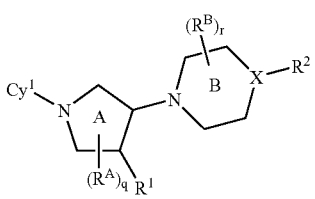

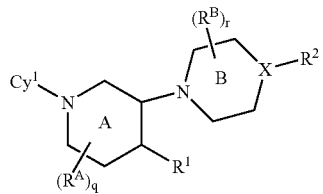

In still other embodiments of formulae II, III, and IV, n is 2 and compounds of any one of formulae II-B, III-B, or IV-B are provided:

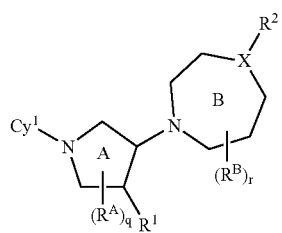

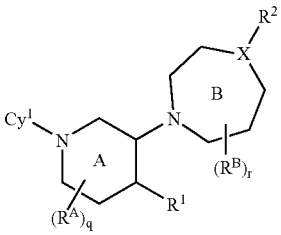

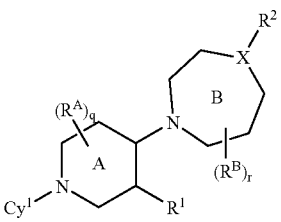

For each of the compounds described generally above (I, II, III, IV, II-A, II-B, III-A, III-B, IV-A, or IV-B), the substituents are defined independently of one another and any combination of substituent subsets (as described in more detail below) may be used to describe the present compounds.

In certain embodiments, for compounds described herein, $R^1$ is —$OR^4$, halogen, —$OCOR^4$, —$NR^4SO_2R^3$, or —$NR^4COR^4$. In other embodiments, $R^1$ is —$OR^4$, —OCO($C_1$-$C_6$alkyl), —$NHSO_2$($C_1$-$C_6$alkyl), —NHCO($C_1$-$C_6$alkyl), or —F. In yet other embodiments, $R^1$ is —OH, —O($C_1$-$C_6$alkyl), —OCO($C_1$-$C_6$alkyl), —$NHSO_2$($C_1$-$C_6$alkyl), —NHCO($C_1$-$C_6$alkyl), or —F. In still other embodiments, $R^1$ is —$OR^4$. In yet other embodiments, $R^1$ is —O($C_1$-$C_6$alkyl) or is —OH.

In other embodiments, for compounds described herein, q is 0, 1, or 2, and —$R^A$ is halogen, an optionally substituted linear or branched $C_1$-$C_6$alkyl, an optionally substituted $C_3$-$C_6$cycloalkyl ring, or two occurrences of $R^A$, taken together with the carbon atom(s) to which they are bound form an optionally substituted fused or spiro $C_3$-$C_6$cycloalkyl ring. In yet other embodiments, q is 0 or 1 and —$R^A$ is optionally substituted linear or branched $C_1$-$C_6$alkyl, or halogen. In still other embodiments, q is 0 or 1 and —$R^A$ is —$CH_3$, —$CH_2CH_3$, or F. In yet other embodiments, q is 0.

In still other embodiments for compounds described herein, $R^1$ and $R^{A'}$ taken together with the carbon atom(s) to which they are bound form an optionally substituted fused or spiro $C_3$-$C_6$cycloalkyl ring.

In yet other embodiments, for compounds of general formula II and subsets thereof, q is 1 and ring A has the structure:

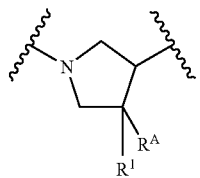

wherein $R^1$ is —OH, —O($C_1$-$C_6$alkyl), —OCO($C_1$-$C_6$alkyl), —$NHSO_2$($C_1$-$C_6$alkyl), —NHCO($C_1$-$C_6$alkyl), or F; and —$R^A$ is optionally substituted linear or branched $C_1$-$C_6$alkyl, or halogen. In still other embodiments, for compounds of general formula II and subsets thereof, q is 1 and ring A has the structure:

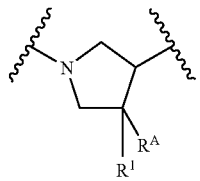

wherein $R^1$ is —$OR^4$, and —$R^A$ is —$CH_3$, $CH_2CH_3$, or F.

In some embodiments for compounds described generally herein, r is 0, 1, or 2, and —$R^B$ is halogen, or an optionally substituted group selected from $C_1$-$C_6$alkyl, $C_3$-$C_6$cycloalkyl, or a fused or bridged 5- or 6-membered saturated ring having 0 heteroatoms. In other embodiments, r is 0, 1, or 2, and —$R^B$ is $C_1$-$C_3$alkyl, or two occurrences of $R^B$, taken together with their intervening atom(s), form an optionally substituted fused or bridged 5 or 6-membered saturated, partially unsaturated, or aromatic ring having 0 heteroatoms. In yet other embodiments, r is 0, 1 or 2, and —$R^B$ is $C_1$-$C_3$alkyl. In still other embodiments, r is 1 or 2 and —$R^B$ is methyl.

In certain embodiments for compounds described herein $R^2$ is -$Cy^2$, or -T-$Cy^2$, and when X is N, T, when present, is a $C_1$-$C_3$alkylene chain substituted with 0 or 1 occurrence of $R^{5a}$, and 0, 1, or 2 independent occurrences of $R^{5b}$, and the $C_1$-$C_3$alkylene chain is optionally replaced by —CO— or —$SO_2$. In other embodiments, when X is $CR^8$, T, when present, is a $C_1$-$C_3$alkylene chain substituted with 0 or 1 occurrence of $R^{5a}$, and 0, 1, or 2 independent occurrences of $R^{5b}$, and the $C_1$-$C_3$alkylene chain is optionally replaced by —$CR^{5c}$=$CR^{5c}$—, —CO—, —O—, —S—, or —$NR^{5c}$—, and $R^8$ is hydrogen, —$C_1$-$C_3$alkyl, —OH, —O($C_1$-$C_3$alkyl), —$NH_2$, —N($C_1$-$C_3$alkyl)$_2$, —SH, —S($C_1$-$C_3$alkyl), —CO($C_1$-$C_3$alkyl), —COOH, or —COO($C_1$-$C_3$alkyl). In yet other embodiments, $R^2$ is -$Cy^2$, or -T-$Cy^2$, and X is N and T, when present, is —$CH_2$—, —CO—, —$CH_2CH$=CH—, or —$CH_2CH_2$—. In still other embodiments, X is $CR^8$, and T, when present, is —$NR^{5c}$—, or —O—, and $R^8$ is hydrogen, $C_1$-$C_3$alkyl, —OH, or —O($C_1$-$C_3$alkyl). In yet other embodiments, X is N, and T, when present, is —CO— or —$CH_2$—. In still other embodiments, X is $CR^8$, and T, when present, is —O— or —$NR^{5c}$—, and $R^8$ is hydrogen, $C_1$-$C_3$alkyl, —OH, or —O($C_1$-$C_3$alkyl).

In yet other embodiments, for compounds described herein $Cy^2$ is an optionally substituted group selected from phenyl, naphthyl, a 5-6-membered monocyclic heteroaryl ring having 1-3 heteroatoms selected from nitrogen, oxygen, or sulfur, or an 8-10-membered bicyclic heteroaryl ring having 1-3 heteroatoms selected from nitrogen, oxygen, or sulfur.

In still other embodiments for compounds described herein $Cy^2$ is an optionally substituted group selected from phenyl, pyridyl, pyrimidinyl, pyrazinyl, pyridazinyl, 1,2,4-triazinyl, 1,3,5-triazinyl, 1,2,3-triazolyl, 1,2,4-triazolyl, imidazolyl, pyrazolyl, pyrrolyl, thiazolyl, isothiazolyl, thienyl, 1,3,4-thiadiazolyl, 1,2,4-thiadiazolyl, isoxazolyl, oxazolyl, furanyl, 1,3,4-oxadiazolyl, 1,2,4-oxadiazolyl, 1,3-dihydroimidazol-2-onyl, quinolinyl, isoquinolinyl, quinazolinyl, quinoxalinyl, [1,8]naphthyridinyl, naphthyl, 1,3-dihydrobenzoimidazol-2-on-1-yl, indolyl, benzo[c]isoxazolyl, benzofuranyl, benzothienyl, benzo[c]isothiazolyl, benzooxazol-2-yl, 5H-pyrrolo[3,2-d]pyrimidinyl, furo[3,2-d]pyrimidinyl, thieno[3,2-d]pyrimidinyl, indanyl, benzo[d]isothiazolyl, benzo[d]isoxazolyl, benzo[1,3]dioxolyl, benzothiazolyl, benzimidazolyl, or indazolyl.

In yet other embodiments for compounds described herein $Cy^2$ is an optionally substituted group selected from:

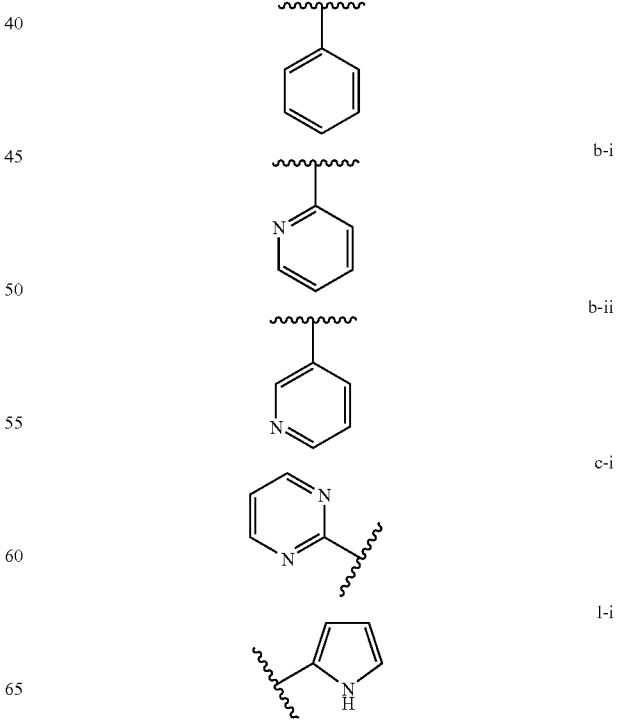

-continued l-ii 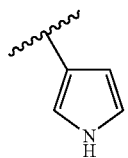

n-i 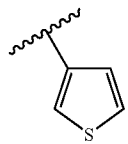

n-ii 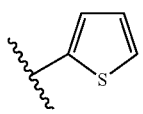

s-i 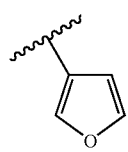

s-ii 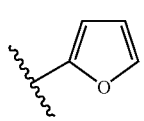

w-i 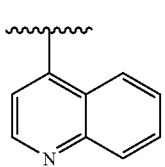

x-i 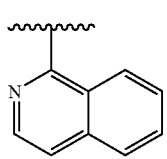

bb-i 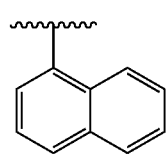

cc 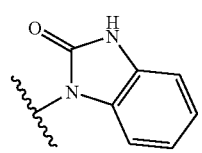

mm-i 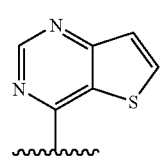

-continued nn-i 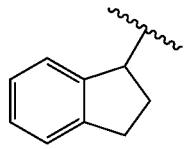

qq-i 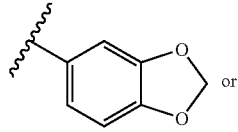 or rr 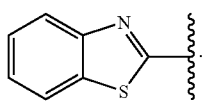

In other embodiments for compounds described herein $Cy^2$ is an optionally substituted group selected from rings a, b-i, w-i, x-i, nn-I, as referenced above.

As described generally above, $Cy^2$ is substituted with 0, 1, or 2 independent occurrences of —$R^{6a}$, -G-$R^{6a}$, or —V-G-$R^{6a}$, and 0 or 1 occurrence of =O, =S, =$NR^{7a}$, =$NR^{7b}$, —$R^{6b}$, -G-$R^{6b}$, or —V-G-$R^{6b}$, wherein:

each —$R^{6a}$, -G-$R^{6a}$, or —V-G-$R^{6a}$, when present, is independently —CN, —$NO_2$, —$OR^{7a}$, —$(CH_2)_{1-4}OR^{7a}$, —$SR^{7a}$, —$(CH_2)_{1-4}SR^{7a}$, halogen, —$COOR^{7a}$, —$(CH_2)_{1-4}COOR^{7a}$, —$COR^{7a}$, —$(CH_2)_{1-4}COR^{7a}$, —$CON(R^{7a})_2$, —$(CH_2)_{1-4}CON(R^{7a})_2$, —$N(R^{7a})_2$, —$(CH_2)_{1-4}N(R^{7a})_2$, —$SO_2N(R^{7a})_2$, —$(CH_2)_{1-4}SO_2N(R^{7a})_2$, —$NR^{7a}SO_2R^{7a}$, or —$(CH_2)_{1-4}NR^{7a}SO_2R^{7a}$, or an optionally substituted $C_1$-$C_6$aliphatic group; and each —$R^{6b}$, -G-$R^{6b}$, or —V-G-$R^{6b}$ is —$OR^{7b}$, —$(CH_2)_{1-4}OR^{7b}$, —$SR^{7b}$, —$(CH_2)_{1-4}SR^{7b}$, —$COOR^{7b}$, —$(CH_2)_{1-4}COOR^{7b}$, —$COR^{7b}$, —$(CH_2)_{1-4}COR^{7b}$, —$CON(R^{7b})(R^{7c})$, —$(CH_2)_{1-4}CON(R^{7b})(R^{7c})$, —$N(R^{7b})(R^{7c})$, —$(CH_2)_{1-4}N(R^{7b})(R^{7c})$, —$SO_2N(R^{7b})(R^{7c})$, —$(CH_2)_{1-4}SO_2N(R^{7b})(R^{7c})$, —$NR^{7c}SO_2R^{7b}$, —$(CH_2)_{1-4}NR^{7c}SO_2R^{7b}$, or an optionally substituted group selected from a 3-7-membered saturated, partially saturated, or aromatic monocyclic ring having 0-3 heteroatoms independently selected from nitrogen, oxygen, or sulfur, or an 8-10-membered saturated, partially unsaturated, or aromatic bicyclic ring having 0-5 heteroatoms independently selected from nitrogen, oxygen, or sulfur.

In other embodiments $Cy^2$ is substituted with:

0, 1, or 2 occurrences of —$R^{6a}$ and each —$R^{6a}$, when present, is independently —Cl, —Br, —F, —CN, —$NO_2$, —$OR^{7a}$, —$SR^{7a}$, —$N(R^{7a})_2$, —$COOR^{7a}$, —$COR^{7a}$, —$SO_2N(R^{7a})_2$, —$NR^{7a}SO_2R^{7a}$, —$CON(R^{7a})_2$, —$NR^{7a}COR^{7a}$, or optionally substituted $C_1$-$C_6$alkyl, wherein each $R^{7a}$ is independently hydrogen, or optionally substituted $C_1$-$C_6$alkyl; and 0 or 1 occurrence of —$R^{6b}$, wherein —$R^{6b}$, when present is —$OR^{7b}$, —$SR^{7b}$, —$N(R^{7b})(R^{7c})$, —$COOR^{7b}$, —$COR^{7b}$, —$SO_2N(R^{7b})(R^{7c})$, —$NR^{7c}SO_2R^{7b}$, —$CON(R^{7b})(R^{7c})$, —$NR^{7c}COR^{7b}$, or an optionally substituted 3-6-membered saturated, partially unsaturated, or aromatic ring having 0-3 heteroatoms independently selected from nitrogen, oxygen, or sulfur, wherein each $R^{7b}$ is independently an optionally substituted 3-6-membered saturated, partially unsaturated, or aromatic ring having 0-3 heteroatoms independently selected from nitrogen, oxygen, or sulfur, and each $R^{7c}$ is independently hydrogen or an optionally substituted group selected from $C_1$-$C_6$alkyl or an optionally substituted 3-6-membered saturated, partially unsaturated, or aromatic ring having 0-3 heteroatoms independently selected from nitrogen, oxygen, or sulfur.

In still other embodiments $Cy^2$ is substituted with 0, 1, or 2 occurrences of —$R^{6a}$ and each —$R^{6a}$, when present, is independently —Cl, —Br, —F, —CN, —$OCH_3$, —$OCH_2CH_3$, —$OCH_2CH_2CH_3$, —$CF_3$, —$CH_3$, —$CH_2CH_3$, —$CH_2CH_2CH_3$, —$CH(CH_3)_2$, —$C(CH_3)_3$, —COOH, —$COOCH_3$, —$COOCH_2CH_3$.

In yet other embodiments for compounds described herein $Cy^2$ is:

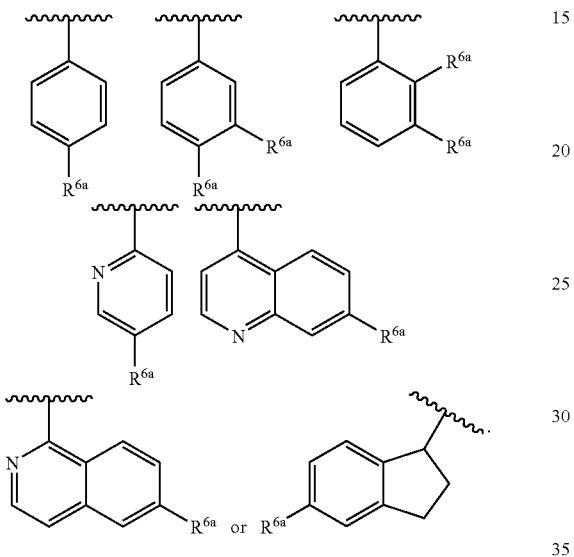

and each $R^{6a}$ is independently —Cl, —Br, —$CH_3$, —$CF_3$, or —F.

In still other embodiments $Cy^2$ is phenyl substituted with 1 or 2 occurrences of —$R^{6a}$, and each —$R^{6a}$ is independently —Cl, —F, —$CF_3$, —$CH_3$, or —Br. In other embodiments, $Cy^2$ is phenyl substituted with 1 occurrence of —$R^{6a}$, and —$R^{6a}$ is —Cl.

In yet other embodiments, for compounds described herein $Cy^1$ is an optionally substituted ring selected from phenyl, naphthyl, a 5-6-membered monocyclic heteroaryl ring having 1-3 heteroatoms selected from nitrogen, oxygen, or sulfur, or an 8-10-membered bicyclic heteroaryl ring having 1-3 heteroatoms selected from nitrogen, oxygen, or sulfur.

In still other embodiments for compounds described herein $Cy^1$ is an optionally substituted group selected from phenyl, pyridyl, pyrimidinyl, pyrazinyl, pyridazinyl, 1,2,4-triazinyl, 1,3,5-triazinyl, 1,2,3-triazolyl, 1,2,4-triazolyl, imidazolyl, pyrazolyl, pyrrolyl, thiazolyl, isothiazolyl, thienyl, 1,3,4-thiadiazolyl, 1,2,4-thiadiazolyl, isoxazolyl, oxazolyl, furanyl, 1,3,4-oxadiazolyl, 1,2,4-oxadiazolyl, 1,3-dihydroimidazol-2-onyl, quinolinyl, isoquinolinyl, quinazolinyl, quinoxalinyl, [1,8]naphthyridinyl, naphthyl, 1,3-dihydrobenzoimidazol-2-on-1-yl, indolyl, benzo[c]isoxazolyl, benzofuranyl, benzothienyl, benzo[c]isothiazolyl, benzooxazol-2-yl, 5H-pyrrolo[3,2-d]pyrimidinyl, furo[3,2-d]pyrimidinyl, thieno[3,2-d]pyrimidinyl, indanyl, benzo[d]isothiazolyl, benzo[d]isoxazolyl, benzo[1,3]dioxolyl, benzothiazolyl, benzimidazolyl, indazolyl, purinyl, pyrido[2,3-d]pyrimidine, or pyrido[3,4-d]pyrimidine.

In other embodiments for compounds described herein $Cy^1$ is an optionally substituted group selected from:

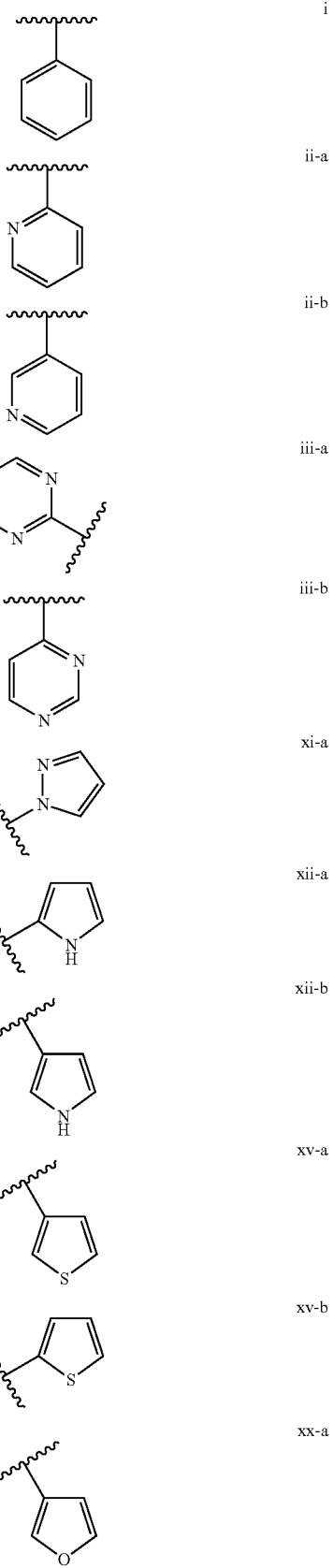

-continued

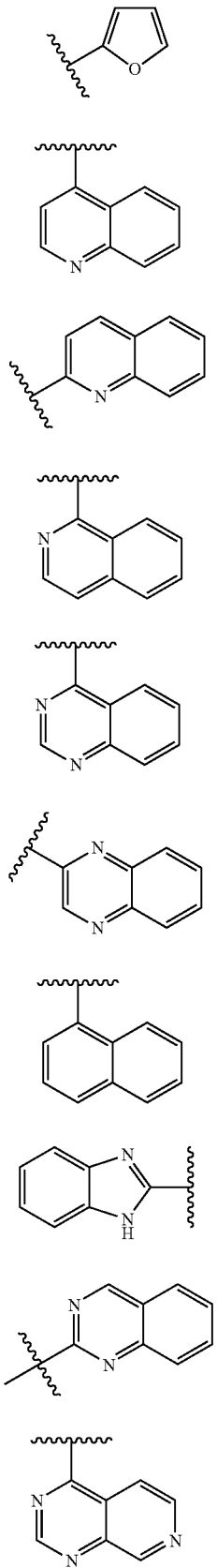

-continued

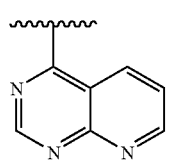

xLvii-a

In still other embodiments for compounds described herein Cy$^1$ is an optionally substituted group selected from i, ii-a, ii-b, iii-a, iii-b, xxiv-a, xxiv-b, xxv-a, xxvi-a, xLiv-a, xLv-a, xLvi-a, or xLvii-a as referenced above. In yet other embodiments, Cy$^1$ is an optionally substituted group selected from 2-pyridyl (ii-a), pyrimidin-2-yl (iii-a), pyrimidin-4-yl (iii-b), quinolinyl (xxiv-a), or 4-quinaozlinyl (xxvi-a) 2-quinazolinyl (xLv-a), pyrido[2,3-d]pyrimidinyl (xLvi-a) or pyrido[3,4-d]pyrimidinyl (xLvii-a).

In some embodiments, Cy$^1$ is substituted with 0, 1, 2, or 3 independent occurrences of —R$^{10a}$, -J-R$^{10a}$, or —W-J-R$^{10a}$, and 0 or 1 occurrence of =O, =S, =NR$^{11a}$, =NR$^{11b}$, —R$^{10b}$, -J-R$^{10b}$, or —W-J-R$^{10b}$, wherein:

each —R$^{10a}$, -J-R$^{10a}$, or —W-J-R$^{10a}$, when present, is independently —CN, —NO$_2$, —OR$^{11a}$, —(CH$_2$)$_{1-4}$OR$^{11a}$, —SR$^{11a}$, —(CH$_2$)$_{1-4}$SR$^{11a}$, halogen, —COOR$^{11a}$, —(CH$_2$)$_{1-4}$COOR$^{11a}$, —COR$^{11a}$, —(CH$_2$)$_{1-4}$COR$^{11a}$, —CON(R$^{11a}$)$_2$, —(CH$_2$)$_{1-4}$CON(R$^{11a}$)$_2$, —N(R$^{11a}$)$_2$, —(CH$_2$)$_{1-4}$N(R$^{11a}$)$_2$, —SO$_2$N(R$^{11a}$)$_2$, —(CH$_2$)$_{1-4}$SO$_2$N(R$^{11a}$)$_2$, —NR$^{11a}$SO$_2$R$^{11a}$, —(CH$_2$)$_{1-4}$NR$^{11a}$SO$_2$R$^{11a}$, —NR$^{11a}$CON(R$^{11a}$)$_2$, —(CH$_2$)$_{1-4}$NR$^{11a}$CON(R$^{11a}$)$_2$, —NR$^{11a}$COOR$^{11a}$, —(CH$_2$)$_{1-4}$NR$^{11a}$COOR$^{11a}$, or an optionally substituted C$_1$-C$_6$aliphatic group; and each —R$^{10b}$, -J-R$^{10b}$, or —W-J-R$^{10b}$ is —OR$^{11b}$, —(CH$_2$)$_{1-4}$OR$^{11b}$, —SR$^{11b}$, —(CH$_2$)$_{1-4}$SR$^{11b}$, —COOR$^{11b}$, —(CH$_2$)$_{1-4}$COOR$^{11b}$, —COR$^{11b}$, —(CH$_2$)$_{1-4}$COR$^{11b}$, —CON(R$^{11b}$)(R$^{11c}$), —(CH$_2$)$_{1-4}$CON(R$^{11b}$)(R$^{11c}$), —N(R$^{11b}$)(R$^{11c}$), —(CH$_2$)$_{1-4}$N(R$^{11b}$)(R$^{11c}$), —SO$_2$N(R$^{11b}$)(R$^{11c}$), —(CH$_2$)$_{1-4}$SO$_2$N(R$^{11b}$)(R$^{11c}$), —NR$^{11c}$SO$_2$R$^{11b}$, —(CH$_2$)$_{1-4}$NR$^{11c}$SO$_2$R$^{11b}$, —NR$^{11c}$CON(R$^{11b}$)(R$^{11c}$), —(CH$_2$)$_{1-4}$NR$^{11c}$CON(R$^{11b}$)(R$^{11c}$), —NR$^{11c}$COOR$^{11b}$, —(CH$_2$)$_{1-4}$NR$^{11c}$COOR$^{11b}$, or an optionally substituted group selected from a 3-7-membered saturated, partially saturated, or aromatic monocyclic ring having 0-3 heteroatoms independently selected from nitrogen, oxygen, or sulfur, or an 8-10-membered saturated, partially unsaturated, or aromatic bicyclic ring having 0-5 heteroatoms independently selected from nitrogen, oxygen, or sulfur.

In certain embodiments Cy$^1$ is substituted with:

0, 1, or 2 occurrences of —R$^{10a}$ and each —R$^{10a}$, when present, is independently —Cl, —Br, —F, —CN, —NO$_2$, —OR$^{11a}$, —SR$^{11a}$, —N(R$^{11a}$)$_2$, —NR$^{11a}$COR$^{11a}$, —CON(R$^{11a}$)$_2$, —SO$_2$N(R$^{11a}$)$_2$, —NR$^{11a}$SO$_2$R$^{11a}$, COOR$^{11a}$, COR$^{11a}$, —NR$^{11a}$CON(R$^{11a}$)$_2$, —NR$^{11a}$COOR$^{11a}$, or optionally substituted C$_1$-C$_6$alkyl, wherein each R$^{11a}$ is independently hydrogen, or optionally substituted C$_1$-C$_6$alkyl; and 0 or 1 occurrence of —R$^{10b}$, J-R$^{10b}$, or W-J-R$^{10b}$, wherein W is —N(R$^{11b}$) or —O—, J is a C$_1$-C$_2$alkyl chain, and —R$^{10b}$, when present is —OR$^{11b}$, —SR$^{11b}$, —N(R$^{11b}$)(R$^{11c}$), —NR$^{11c}$COR$^{11b}$, CON(R$^{11b}$)(R$^{11c}$), —SO$_2$N(R$^{11c}$)(R$^{11b}$), —NR$^{11c}$SO$_2$R$^{11b}$, —COOR$^{11b}$, COR$^{11b}$, —NR$^{11c}$CON(R$^{11b}$)(R$^{11c}$), —NR$^{11c}$COOR$^{11b}$, or an optionally substituted 3-6-membered saturated, partially unsaturated, or aromatic ring having 0-3 heteroatoms independently selected from nitrogen, oxygen, or sulfur, wherein each R$^{11b}$ is independently an optionally substituted 3-6-membered saturated, partially unsaturated, or aromatic ring having 0-3 heteroatoms independently selected from nitrogen, oxygen, or sulfur, and each $R^{11c}$ is independently hydrogen or an optionally substituted group selected from $C_1$-$C_6$alkyl or an optionally substituted 3-6-membered saturated, partially unsaturated, or aromatic ring having 0-3 heteroatoms independently selected from nitrogen, oxygen, or sulfur.

In other embodiments $Cy^1$ is substituted with:

0, 1, or 2 occurrences of $R^{10a}$, and each —$R^{10a}$ is independently —Cl, —Br, —F, —$NO_2$, —CN, —$OCH_3$, —$OCH_2CH_3$, —$OCH_2CH_2CH_3$, —$CF_3$, —$OCF_3$, —$CH_3$, —$CH_2CH_3$, —$CH_2CH_2CH_3$, —$C(CH_3)_3$, —$CH(CH_3)_2$, t-Bu, —$NHCOCH_3$, —$NHCONHCH_3$, —$SCH_3$, —$SCH_2CH_3$, —$SCH_2CH_2CH_3$, —$NH_2$, —$NHCH_3$, —$SO_2NH_2$, —COOH, —$COOCH_3$, —$COOCH_2CH_3$, —$NHCH_3$, —$N(CH_3)_2$, —$NH(CH_2CH_3)$, —$N(CH_2CH_3)_2$, —$OC(CH_3)_2CO_2H$, —$OCH_2CO_2H$, —$C(CH_3)_2OH$, —$CONH_2$, —$NHCONH_2$, —$NHCON(CH_3)_2$, or —NHCOOCH$_3$, and 0 or 1 occurrence of —$R^{10b}$, J-$R^{10b}$, or W-J-$R^{10b}$, and —$R^{10b}$, J-$R^{10b}$, or W-J-$R^{10b}$ is morpholinyl, tetrazolyl,

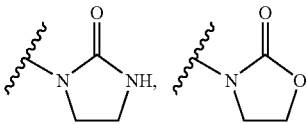

phenyl, benzyl, —NHCO(phenyl), —NHCO(benzyl), —NH(phenyl), —$NHCH_2$(phenyl), —NH(benzyl), —S(phenyl), —S(benzyl), —O(phenyl), or —O(benzyl), wherein the phenyl and benzyl groups are optionally substituted.

In yet other embodiments, $Cy^1$ is substituted with 1, 2, or 3 occurrences of $R^{10a}$, and each $R^{10a}$ is independently —Cl, —Br, —F, —$CH_3$, —$CF_3$, —$COOCH_3$, —$CONH_2$, —$NHCONH_2$, —$NHCOOCH_3$, —$NHCONHCH_3$, —$CONHCH_3$, —$C(CH_3)_2OH$, —$OCH_3$, —$OCH_2CH_3$, —CN, -tetrazole, —$NO_2$, —$N(CH_3)_2$, -or COOH.

In still other embodiments, $Cy^1$ is substituted with 1, 2, or 3 occurrences of $R^{10a}$, and each $R^{10a}$ is independently —Cl, —Br, —F, —$CH_3$, or —$CF_3$.

One embodiment relates to compounds where $Cy^1$ is a quinazolinyl ring as shown in formulae II-A-1 and II-A-2:

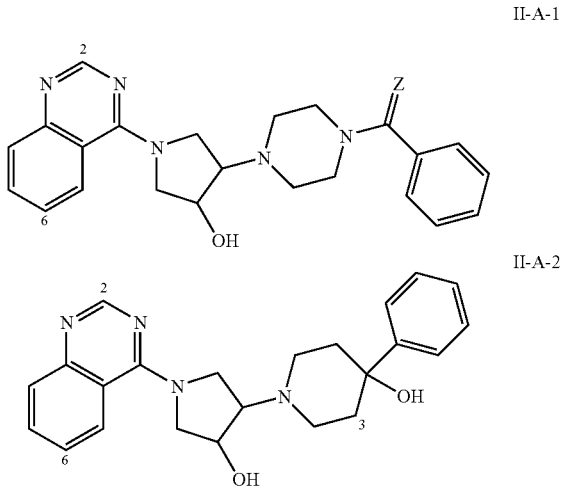

where Z is $H_2$ or oxygen. In the II-A-1 and II-A-2 compounds, the 2-position of the quinazoline ring is preferably occupied by a small group such as hydrogen or $CF_3$. The 6-position of the quinazoline ring may be substituted or unsubstituted. Examples of substituents at the 6-position of the quinazoline ring include F, Cl, Br, —$OCH_3$, —$C(CH_3)_2$—OH, —COOH, —$O(C_{1-3}$ alkyl) such as —OEt or —O-iPr, —$OCH_2COOH$, —$OC(CH_3)_2COOH$, —$OC(CH_3)_2CH_2OH$, —$OCH_2C(CH_3)_2OH$, —$OCH_2CONH_2$, —$OCH_2CH_2OH$, —OCONHCH(CH$_3$)$_2$, —OCONHCHCH$_3$, —$OCH_2CH_2$-morpholin-4-yl. The 7-position of the quinazoline ring may be substituted or unsubstituted. Example of substituents at the 7-position include Cl or $CF_3$. For compounds of formula II-A-2, the piperidine ring may be substituted or unsubstituted. In one embodiment the 3-position of the piperidine ring is substituted with two methyl groups. In the II-A-1 and II-A-2 compounds, on the opposite end of the quinazoline the phenyl ring may be substituted or unsubstituted. When the phenyl ring is substituted, small groups such as chloro are preferred, especially in the para position.

It will be appreciated that in still other embodiments, certain combinations of substituents are preferred. In some embodiments, certain variables for compounds of general formula I (and subsets thereof as depicted by general formulae II, III, and IV, and subsets thereof) are selected from a) $R^1$ is —$OR^4$, halogen, —$OCOR^4$, —$NR^4SO_2R^3$, or —$NR^4COR^4$; q is 0, 1, or 2, and —$R^A$ is halogen, an optionally substituted linear or branched $C_1$-$C_6$alkyl, an optionally substituted $C_3$-$C_6$cycloalkyl ring, or two occurrences of $R^A$, taken together with the carbon atom(s) to which they are bound form an optionally substituted fused or spiro $C_3$-$C_6$cycloalkyl ring; or $R^1$ and $R^{A'}$ taken together with the carbon atom(s) to which they are bound form an optionally substituted fused or spiro $C_3$-$C_6$cycloalkyl ring;

b) r is 0, 1, or 2, and —$R^B$ is halogen, or an optionally substituted group selected from $C_1$-$C_6$alkyl, $C_3$-$C_6$cycloalkyl, or a fused or bridged 5- or 6-membered saturated ring having 0 heteroatoms;

c) $R^2$ is -$Cy^2$, or -T-$Cy^2$, and when X is N, then T, when present, is a $C_1$-$C_3$alkylene chain substituted with 0 or 1 occurrence of $R^{5a}$, and 0, 1, or 2 independent occurrences of $R^{5b}$, and wherein one or more methylene units in the $C_1$-$C_3$alkylene chain is optionally replaced by —CO— or —$SO_2$, or when X is $CR^8$, then T, when present, is a $C_1$-$C_3$alkylene chain substituted with 0 or 1 occurrence of $R^{5a}$, and 0, 1, or 2 independent occurrences of $R^{5b}$, and wherein one or more methylene units in the $C_1$-$C_3$alkylene chain, as valency and stability permit, is optionally replaced by —$CR^{5c}$=$CR^{5c}$—, —CO—, —O—, —S—, or —$NR^{5c}$—, and $R^8$ is hydrogen, $C_1$-$C_3$alkyl, —OH, —O($C_1$-$C_3$alkyl), —$NH_2$, —N($C_1$-$C_3$alkyl)$_2$, —SH, —S($C_1$-$C_3$alkyl), —CO($C_1$-$C_3$alkyl), —COOH, or —COO($C_1$-$C_3$alkyl);

$Cy^2$ is an optionally substituted ring selected from phenyl, naphthyl, a 5-6-membered monocyclic heteroaryl ring having 1-3 heteroatoms selected from nitrogen, oxygen, or sulfur, or an 8-10-membered bicyclic heteroaryl ring having 1-3 heteroatoms selected from nitrogen, oxygen, or sulfur, wherein $Cy^2$ is substituted with 0, 1, or 2 independent occurrences of —$R^{6a}$, -G-$R^{6a}$, or —V-G-$R^{6a}$, and 0 or 1 occurrence of =O, =S, =$NR^{7a}$, =$NR^{7b}$, —$R^{6b}$, -G-$R^{6b}$, or —V-G-$R^{6b}$, wherein:

each —$R^{6a}$, -G-$R^{6a}$, or —V-G-$R^{6a}$, when present, is independently —CN, —$NO_2$, —$OR^{7a}$, —$(CH_2)_{1-4}OR^{7a}$, —$SR^{7a}$, —$(CH_2)_{1-4}SR^{7a}$, halogen, —$COOR^{7a}$, —$(CH_2)_{1-4}COOR^{7a}$, —$COR^{7a}$, —$(CH_2)_{1-4}COR^{7a}$, —$CON(R^{7a})_2$, —$(CH_2)_{1-4}CON(R^{7a})_2$, —$N(R^{7a})_2$, —$(CH_2)_{1-4}N(R^{7a})_2$, —$SO_2N(R^{7a})_2$, —(CH$_2$)$_{1-4}$SO$_2$N(R$^{7a}$)$_2$, —NR$^{7a}$SO$_2$R$^{7a}$, or —(CH$_2$)$_{1-4}$NR$^{7a}$SO$_2$R$^{7a}$, or an optionally substituted C$_1$-C$_6$aliphatic group; and each —R$^{6b}$, -G-R$^{6b}$, or —V-G-R$^{6b}$ is —OR$^{7b}$, —(CH$_2$)$_{1-4}$OR$^{7b}$, —SR$^{7b}$, —(CH$_2$)$_{1-4}$SR$^{7b}$, —COOR$^{7b}$, —(CH$_2$)$_{1-4}$COOR$^{7b}$, —COR$^{7b}$, —(CH$_2$)$_{1-4}$COR$^{7b}$, —CON(R$^{7b}$)(R$^{7c}$), —(CH$_2$)$_{1-4}$CON(R$^{7b}$)(R$^{7c}$), —N(R$^{7b}$)R$^{7c}$), —(CH$_2$)$_{1-4}$N(R$^{7b}$)(R$^{7c}$), —SO$_2$N(R$^{7b}$)(R$^{7c}$), —(CH$_2$)$_{1-4}$SO$_2$N(R$^{7b}$(R$^{7c}$), —NR$^{7c}$SO$_2$R$^{7b}$, —(CH$_2$)$_{1-4}$NR$^{7c}$SO$_2$R$^{7b}$, or an optionally substituted group selected from a 3-7-membered saturated, partially saturated, or aromatic monocyclic ring having 0-3 heteroatoms independently selected from nitrogen, oxygen, or sulfur, or an 8-10-membered saturated, partially unsaturated, or aromatic bicyclic ring having 0-5 heteroatoms independently selected from nitrogen, oxygen, or sulfur; and d) Cy$^1$ is selected from phenyl, naphthyl, a 5-6-membered monocyclic heteroaryl ring having 1-3 heteroatoms selected from nitrogen, oxygen, or sulfur, or an 8-10-membered bicyclic heteroaryl ring having 1-3 heteroatoms selected from nitrogen, oxygen, or sulfur, wherein Cy$^1$ is substituted with 0, 1, 2, or 3 independent occurrences of —R$^{10a}$, -J-R$^{10a}$, or —W-J-R$^{10a}$, and 0 or 1 occurrence of =O, =S, =NR$^{11a}$, =NR$^{11b}$, —R$^{10b}$, -J-R$^{10b}$, or —W-J-R$^{10b}$, wherein each —R$^{10a}$, -J-R$^{10a}$, or —W-J-R$^{10a}$, when present, is independently —CN, —NO$_2$, —OR$^{11a}$, —(CH$_2$)$_{1-4}$OR$^{11a}$, —SR$^{11a}$, —(CH$_2$)$_{1-4}$SR$^{11a}$, halogen, —COOR$^{11a}$, —(CH$_2$)$_{1-4}$COOR$^{11a}$, —COR$^{11a}$, —(CH$_2$)$_{1-4}$COR$^{11a}$, —CON(R$^{11a}$)$_2$, —(CH$_2$)$_{1-4}$CON(R$^{11a}$)$_2$, —N(R$^{11a}$)$_2$, —(CH$_2$)$_{1-4}$N(R$^{11a}$)$_2$, —SO$_2$N(R$^{11a}$)$_2$, —(CH$_2$)$_{1-4}$SO$_2$N(R$^{11a}$)$_2$, —NR$^{11a}$SO$_2$R$^{11a}$, —(CH$_2$)$_{1-4}$NR$^{11a}$SO$_2$R$^{11a}$, —NR$^{11a}$CON(R$^{11a}$)$_2$, —(CH$_2$)$_{1-4}$NR$^{11a}$CON(R$^{11a}$)$_2$, —NR$^{11a}$COOR$^{11a}$, —(CH$_2$)$_{1-4}$NR$^{11a}$COOR$^{11a}$, or an optionally substituted C$_1$-C$_6$aliphatic group; and each —R$^{10b}$, -J-R$^{10b}$, or —W-J-R$^{10b}$ is —OR$^{11b}$, —(CH$_2$)$_{1-4}$OR$^{11b}$, —SR$^{11b}$, —(CH$_2$)$_{1-4}$SR$^{11b}$, —COOR$^{11b}$, —(CH$_2$)$_{1-4}$COOR$^{11b}$, —COR$^{11b}$, —(CH$_2$)$_{1-4}$COR$^{11b}$, —CON(R$^{11b}$)(R$^{11c}$), —(CH$_2$)$_{1-4}$CON(R$^{11b}$)(R$^{11c}$), —N(R$^{11b}$)(R$^{11c}$), —(CH$_2$)$_{1-4}$N(R$^{11b}$)(R$^{11c}$), —SO$_2$N(R$^{11b}$)(R$^{11c}$), —(CH$_2$)$_{1-4}$SO$_2$N(R$^{11b}$)(R$^{11c}$), —NR$^{11c}$SO$_2$R$^{11b}$, —(CH$_2$)$_{1-4}$NR$^{11c}$SO$_2$R$^{11b}$, —NR$^{11c}$CON(R$^{11b}$)(R$^{11c}$), —(CH$_2$)$_{1-4}$NR$^{11c}$CON(R$^{11b}$)(R$^{11c}$), —NR$^{11c}$COOR$^{11b}$, —(CH$_2$)$_{1-4}$NR$^{11c}$COOR$^{11b}$, or an optionally substituted group selected from a 3-7-membered saturated, partially saturated, or aromatic monocyclic ring having 0-3 heteroatoms independently selected from nitrogen, oxygen, or sulfur, or an 8-10-membered saturated, partially unsaturated, or aromatic bicyclic ring having 0-5 heteroatoms independently selected from nitrogen, oxygen, or sulfur.

In other embodiments, certain variables for compounds of general formula I (and subsets thereof as depicted by general formulae II, III, and IV, and subsets thereof) are selected from a) R$^1$ is —OR$^4$, halogen, —OCOR$^4$, —NR$^4$SO$_2$R$^3$, or —NR$^4$COR$^4$; q is 0, 1, or 2, and —R$^A$ is halogen, an optionally substituted linear or branched C$_1$-C$_6$alkyl, an optionally substituted C$_3$-C$_6$cycloalkyl ring, or two occurrences of R$^A$, taken together with the carbon atom(s) to which they are bound form an optionally substituted fused or spiro C$_3$-C$_6$cycloalkyl ring; or R$^1$ and R$^A$, taken together with the carbon atom(s) to which they are bound form an optionally substituted fused or spiro C$_3$-C$_6$cycloalkyl ring;

b) r is 0, 1, or 2, and —R$^B$ is halogen, or an optionally substituted group selected from C$_1$-C$_6$alkyl, C$_3$-C$_6$cycloalkyl, or a fused or bridged 5- or 6-membered saturated ring having 0 heteroatoms;

c) R$^2$ is -Cy$^2$ or -T-Cy$^2$, and when X is N, then T, when present, is a C$_1$-C$_3$alkylene chain substituted with 0 or 1 occurrence of R$^{5a}$, and 0, 1, or 2 independent occurrences of R$^{5b}$, and wherein one or more methylene units in the C$_1$-C$_3$alkylene chain is optionally replaced by —CO— or —SO$_2$—, or when X is CR$^8$, then T, when present, is a C$_1$-C$_3$alkylene chain substituted with 0 or 1 occurrence of R$^{5a}$, and 0, 1, or 2 independent occurrences of R$^{5b}$, and wherein one or more methylene units in the C$_1$-C$_3$alkylene chain, as valency and stability permit, is optionally replaced by —CR$^{5c}$=CR$^{5c}$—, —CO—, —O—, —S—, or —NR$^{5c}$—, and R$^8$ is hydrogen, C$_1$-C$_3$alkyl, —OH, —O(C$_1$-C$_3$alkyl), —NH$_2$, —N(C$_1$-C$_3$alkyl)$_2$, —SH, —S(C$_1$-C$_3$alkyl), —CO(C$_1$-C$_3$alkyl), —COOH, or —COO(C$_1$-C$_3$alkyl);

Cy$^2$ is selected from phenyl, pyridyl, pyrimidinyl, pyrazinyl, pyridazinyl, 1,2,4-triazinyl, 1,3,5-triazinyl, 1,2,3-triazolyl, 1,2,4-triazolyl, imidazolyl, pyrazolyl, pyrrolyl, thiazolyl, isothiazolyl, thienyl, 1,3,4-thiadiazolyl, 1,2,4-thiadiazolyl, isoxazolyl, oxazolyl, furanyl, 1,3,4-oxadiazolyl, 1,2,4-oxadiazolyl, 1,3-dihydroimidazol-2-onyl, quinolinyl, isoquinolinyl, quinazolinyl, quinoxalinyl, [1,8]naphthyridinyl, naphthyl, 1,3-dihydro-benzoimidazol-2-on-1-yl, indolyl, benzo[c]isoxazolyl, benzofuranyl, benzothienyl, benzo[c]isothiazolyl, benzooxazol-2-yl, 5H-pyrrolo[3,2-d]pyrimidinyl, furo[3,2-d]pyrimidinyl, thieno[3,2-d]pyrimidinyl, indanyl, benzo[d]isothiazolyl, benzo[d]isoxazolyl, benzo[1,3]dioxolyl, benzothiazolyl, benzimidazolyl, or indazolyl.

wherein Cy$^2$ is substituted with 0, 1, or 2 independent occurrences of —R$^{6a}$, -G-R$^{6a}$, or —V-G-R$^{6a}$, and 0 or 1 occurrence of =O, =S, =NR$^{7a}$, =NR$^{7b}$, —R$^{6b}$, -G-R$^{6b}$, or —V-G-R$^{6b}$, wherein each —R$^{6a}$, -G-R$^{6a}$, or —V-G-R$^{6a}$, when present, is independently —CN, —NO$_2$, —OR$^{7a}$, —(CH$_2$)$_{1-4}$OR$^{7a}$, —SR$^{7a}$, —(CH$_2$)$_{1-4}$SR$^{7a}$, halogen, —COOR$^{7a}$, —(CH$_2$)$_{1-4}$COOR$^{7a}$, —COR$^{7a}$, —(CH$_2$)$_{1-4}$COR$^{7a}$, —CON(R$^{7a}$)$_2$, —(CH$_2$)$_{1-4}$CON(R$^{7a}$)$_2$, —N(R$^{7a}$)$_2$, —(CH$_2$)$_{1-4}$N(R$^{7a}$)$_2$, —SO$_2$N(R$^{7a}$)$_2$, —(CH$_2$)$_{1-4}$SO$_2$N(R$^{7a}$)$_2$, —NR$^{7a}$SO$_2$R$^{7a}$, or —(CH$_2$)$_{1-4}$NR$^{7a}$SO$_2$R$^{7a}$, or an optionally substituted C$_1$-C$_6$aliphatic group; and each —R$^{6b}$, -G-R$^{6b}$, or —V-G-R$^{6b}$ is —OR$^{7b}$, —(CH$_2$)$_{1-4}$OR$^{7b}$, —SR$^{7b}$, —(CH$_2$)$_{1-4}$SR$^{7b}$, —COOR$^{7b}$, —(CH$_2$)$_{1-4}$COOR$^{7b}$, —COR$^{7b}$, —(CH$_2$)$_{1-4}$COR$^{7b}$, —CON(R$^{7b}$)(R$^{7c}$), —(CH$_2$)$_{1-4}$CON(R$^{7b}$)(R$^{7c}$), —N(R$^{7b}$)(R$^{7c}$), —(CH$_2$)$_{1-4}$N(R$^{7b}$)(R$^{7c}$), —SO$_2$N(R$^{7b}$)(R$^{7c}$), —(CH$_2$)$_{1-4}$SO$_2$N(R$^{7b}$)(R$^{7c}$), —NR$^{7c}$SO$_2$R$^{7b}$, —(CH$_2$)$_{1-4}$NR$^{7c}$SO$_2$R$^{7b}$, or an optionally substituted group selected from a 3-7-membered saturated, partially saturated, or aromatic monocyclic ring having 0-3 heteroatoms independently selected from nitrogen, oxygen, or sulfur, or an 8-10-membered saturated, partially unsaturated, or aromatic bicyclic ring having 0-5 heteroatoms independently selected from nitrogen, oxygen, or sulfur; and d) Cy$^1$ is selected from phenyl, pyridyl, pyrimidinyl, pyrazinyl, pyridazinyl, 1,2,4-triazinyl, 1,3,5-triazinyl, 1,2,3-triazolyl, 1,2,4-triazolyl, imidazolyl, pyrazolyl, pyrrolyl, thiazolyl, isothiazolyl, thienyl, 1,3,4-thiadiazolyl, 1,2,4-thiadiazolyl, isoxazolyl, oxazolyl, furanyl, 1,3,4-oxadiazolyl, 1,2,4-oxadiazolyl, 1,3-dihydroimidazol-2-onyl, quinolinyl, isoquinolinyl, quinazolinyl, quinoxalinyl, [1,8]naphthyridinyl, naphthyl, 1,3-dihydro-benzoimidazol-2-on-1-yl, indolyl, benzo[c]isoxazolyl, benzofuranyl, benzothienyl, benzo[c]isothiazolyl, benzooxazol-2-yl, 5H-pyrrolo[3,2-d]pyrimidinyl, furo[3,2-d]pyrimidinyl, thieno[3,2-d]pyrimidinyl, indanyl, benzo[d]isothiazolyl, benzo[d]isoxazolyl, benzo[1,3]dioxolyl, benzothiazolyl, benzimidazolyl, indazolyl, purinyl, pyrido[2,3-d]pyrimidine, or pyrido[3,4-d]pyrimidine; wherein Cy$^1$ is substituted with 0, 1, 2, or 3 independent occurrences of —R$^{10a}$, -J-R$^{10a}$, or —W-J-R$^{10a}$, and 0 or 1 occurrence of =O, =S, =NR$^{11a}$, =NR$^{11b}$, —R$^{10b}$, -J-R$^{10b}$, or —W-J-R$^{10b}$, wherein:

each —R$^{10a}$, -J-R$^{10a}$, or —W-J-R$^{10a}$, when present, is independently —CN, —NO$_2$, —OR$^{11a}$, —(CH$_2$)$_{1-4}$OR$^{11a}$, —SR$^{11a}$, —(CH$_2$)$_{1-4}$SR$^{11a}$, halogen, —COOR$^{11a}$, —(CH$_2$)$_{1-4}$COOR$^{11a}$, —COR$^{11a}$, —(CH$_2$)$_{1-4}$COR$^{11a}$, —CON(R$^{11a}$)$_2$, —(CH$_2$)$_{1-4}$CON(R$^{11a}$)$_2$, —N(R$^{11a}$)$_2$, —(CH$_2$)$_{1-4}$N(R$^{11a}$)$_2$, —SO$_2$N(R$^{11a}$)$_2$, —(CH$_2$)$_{1-4}$SO$_2$N(R$^{11a}$)$_2$, —NR$^{11a}$SO$_2$R$^{11a}$, —(CH$_2$)$_{1-4}$NR$^{11a}$SO$_2$R$^{11a}$, —NR$^{11a}$CON(R$^{11a}$)$_2$, —(CH$_2$)$_{1-4}$NR$^{11a}$CON(R$^{11a}$)$_2$, —NR$^{11a}$COOR$^{11a}$, —(CH$_2$)$_{1-4}$NR$^{11a}$COOR$^{11a}$, or an optionally substituted C$_1$-C$_6$aliphatic group; and each —R$^{10b}$, -J-R$^{10b}$, or —W-J-R$^{10b}$ is —OR$^{11b}$, —(CH$_2$)$_{1-4}$OR$^{11b}$, —SR$^{11b}$, —(CH$_2$)$_{1-4}$SR$^{11b}$, —COOR$^{11b}$, —(CH$_2$)$_{1-4}$COOR$^{11b}$, —COR$^{11b}$, —(CH$_2$)$_{1-4}$COR$^{11b}$, —CON(R$^{11b}$)(R$^{11c}$), —(CH$_2$)$_{1-4}$CON(R$^{11b}$)(R$^{11c}$), —N(R$^{11b}$)(R$^{11c}$), —(CH$_2$)$_{1-4}$N(R$^{11b}$)(R$^{11c}$), —SO$_2$N(R$^{11b}$)(R$^{11c}$), —(CH$_2$)$_{1-4}$SO$_2$N(R$^{11b}$)(R$^{11c}$), —NR$^{11c}$SO$_2$R$^{11b}$, —(CH$_2$)$_{1-4}$NR$^{11c}$SO$_2$R$^{11b}$, —NR$^{11c}$CON(R$^{11b}$)(R$^{11c}$), —(CH$_2$)$_{1-4}$NR$^{11c}$CON(R$^{11b}$)(R$^{11c}$), —NR$^{11c}$COOR$^{11b}$, —(CH$_2$)$_{1-4}$NR$^{11c}$COOR$^{11b}$, or an optionally substituted group selected from a 3-7-membered saturated, partially saturated, or aromatic monocyclic ring having 0-3 heteroatoms independently selected from nitrogen, oxygen, or sulfur, or an 8-10-membered saturated, partially unsaturated, or aromatic bicyclic ring having 0-5 heteroatoms independently selected from nitrogen, oxygen, or sulfur.

In other embodiments, certain variables for compounds of general formula I (and subsets thereof as depicted by general formulae II, III, and IV, and subsets thereof) are selected from a) R$^1$ is —OH, —O(C$_1$-C$_6$alkyl), —OCO(C$_1$-C$_6$alkyl), —NHSO$_2$(C$_1$-C$_6$alkyl), —NHCO(C$_1$-C$_6$alkyl), or —F;

b) q is 0 or 1 and —R$^A$ is optionally substituted linear or branched C$_1$-C$_6$alkyl, or halogen;

c) r is 0, 1, or 2, and —R$^B$ is C$_1$-C$_3$alkyl, or two occurrences of R$^B$, taken together with their intervening atom(s), form an optionally substituted fused or bridged 5 or 6-membered saturated, partially unsaturated, or aromatic ring having 0 heteroatoms;

d) R$^2$ is -Cy$^2$ or -T-Cy$^2$, and

X is N and T, when present, is —CH$_2$—, —CO—, —CH$_2$CH=CH—, or —CH$_2$CH$_2$—, or X is CR$^8$, and T, when present, is —NR$^{5c}$—, or —O—, and R$^8$ is hydrogen, C$_1$-C$_3$alkyl, —OH, or —O(C$_1$-C$_3$alkyl); and Cy$^2$ is:

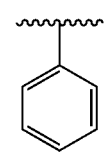

a

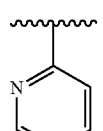

b-i

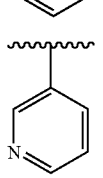

b-ii

-continued

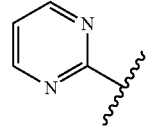

c-i

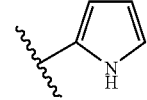

l-i

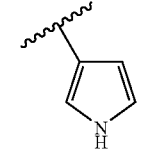

l-ii

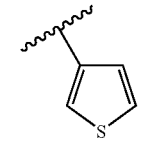

n-i

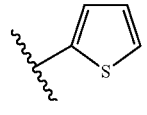

n-ii

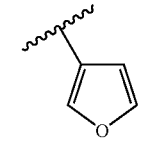

s-i

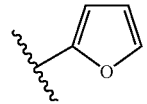

s-ii

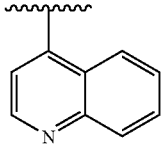

w-i

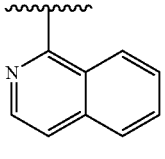

x-i

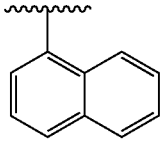

bb-i

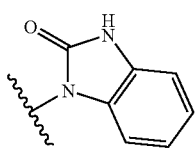

cc

-continued

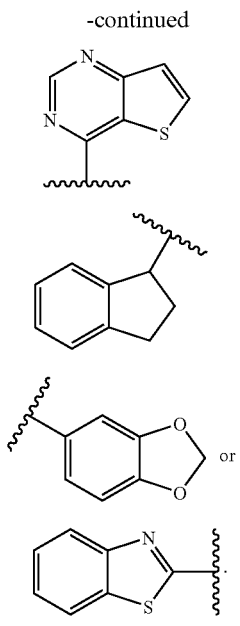

mm-i nn-i qq-I or rr

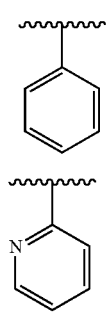

wherein Cy² is substituted with:

0, 1, or 2 occurrences of —R$^{6a}$ and each —R$^{6a}$, when present, is independently —Cl, —Br, —F, —CN, —NO$_2$, —OR$^{7a}$, —SR$^{7a}$, —N(R$^{7a}$)$_2$, —COOR$^{7a}$, —COR$^{7a}$, —SO$_2$N(R$^{7a}$)$_2$, —NR$^{7a}$SO$_2$R$^{7a}$, —CON(R$^{7a}$)$_2$, —NR$^{7a}$COR$^{7a}$, or optionally substituted C$_1$-C$_6$alkyl, wherein each R$^{7a}$ is independently hydrogen, or optionally substituted C$_1$-C$_6$alkyl; and 0 or 1 occurrence of —R$^{6b}$, wherein —R$^{6b}$, when present is —OR$^{7b}$, —SR$^{7b}$, —N(R$^{7b}$)(R$^{7c}$), —COOR$^{7b}$, —COR$^{7b}$, —SO$_2$N(R$^{7b}$)(R$^{7c}$), —NR$^{7c}$SO$_2$R$^{7b}$, —CON(R$^{7b}$)(R$^{7c}$), —NR$^{7c}$COR$^{7b}$, or an optionally substituted 3-6-membered saturated, partially unsaturated, or aromatic ring having 0-3 heteroatoms independently selected from nitrogen, oxygen, or sulfur, wherein each R$^{7b}$ is independently an optionally substituted 3-6-membered saturated, partially unsaturated, or aromatic ring having 0-3 heteroatoms independently selected from nitrogen, oxygen, or sulfur, and each R$^{7c}$ is independently hydrogen or an optionally substituted group selected from C$_1$-C$_6$alkyl or an optionally substituted 3-6-membered saturated, partially unsaturated, or aromatic ring having 0-3 heteroatoms independently selected from nitrogen, oxygen, or sulfur;

e) Cy$^1$ is:

i

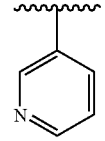

ii-a

-continued

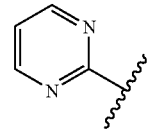

ii-b

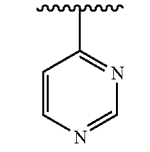

iii-a

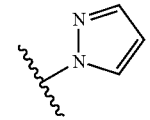

iii-b

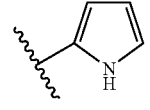

xi-a

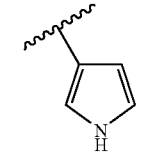

xii-a

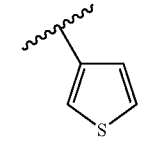

xii-b

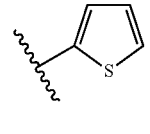

xv-a

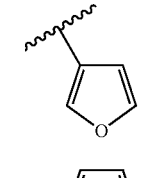

xv-b xx-a xx-b

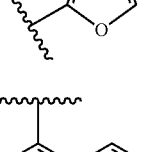

xxiv-a

-continued

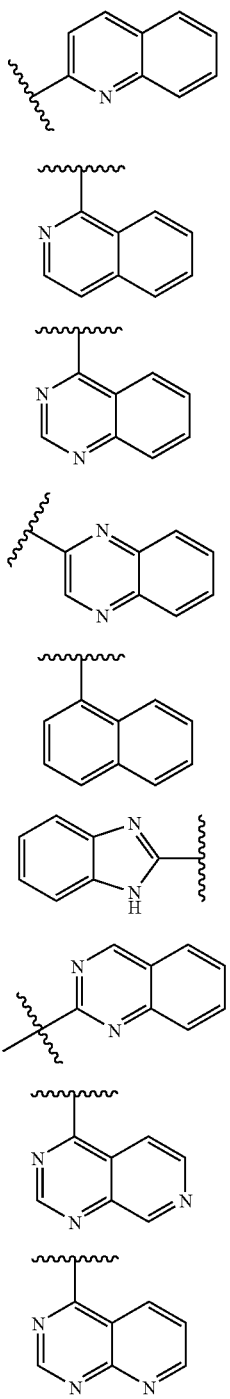

xxiv-b xxv-a xxvi-a xxvii-a xxxix xLiv-a xLv-a xLvi-a xLvii-a wherein $Cy^1$ is substituted with:

0, 1, or 2 occurrences of —$R^{10a}$ and each —$R^{10a}$, when present, is independently —Cl, —Br, —F, —CN, —$NO_2$, —$OR^{11a}$, —$SR^{11a}$, —$N(R^{11a})_2$, —$NR^{11a}COR^{11a}$, —$CON(R^{11a})_2$, —$SO_2N(R^{11a})_2$, —$NR^{11a}SO_2R^{11a}$, $COOR^{11a}$, $COR^{11a}$, —$NR^{11a}CON(R^{11a})_2$, —$NR^{11a}COOR^{11a}$, or optionally substituted $C_1$-$C_6$alkyl, wherein each $R^{11a}$ is independently hydrogen, or optionally substituted $C_1$-$C_6$alkyl; and 0 or 1 occurrence of —$R^{10b}$, -J-$R^{10b}$, or —W-J-$R^{10b}$, wherein W is —$N(R^{11b})$ or —O—, J is a $C_1$-$C_2$alkyl chain, and —$R^{10b}$, when present is —$OR^{11b}$, —$SR^{11b}$, —$N(R^{11b})(R^{11c})$, —$NR^{11c}COR^{11b}$, $CON(R^{11b})(R^{11c})$, —$SO_2N(R^{11c})(R^{11b})$, —$NR^{11c}SO_2R^{11b}$, —$COOR^{11b}$, $COR^{11b}$, —$NR^{11c}CON(R^{11b})(R^{11c})$, —$NR^{11c}COOR^{11b}$, or an optionally substituted 3-6-membered saturated, partially unsaturated, or aromatic ring having 0-3 heteroatoms independently selected from nitrogen, oxygen, or sulfur, wherein each $R^{11b}$ is independently an optionally substituted 3-6-membered saturated, partially unsaturated, or aromatic ring having 0-3 heteroatoms independently selected from nitrogen, oxygen, or sulfur, and each $R^{11c}$ is independently hydrogen or an optionally substituted group selected from $C_1$-$C_6$alkyl or an optionally substituted 3-6-membered saturated, partially unsaturated, or aromatic ring having 0-3 heteroatoms independently selected from nitrogen, oxygen, or sulfur.

In yet other embodiments, certain variables for compounds of general formula I (and subsets thereof as depicted by general formulae II, III, and IV, and subsets thereof) are further selected from a) $R^1$ is —OH, or —$O(C_1$-$C_6$alkyl);
b) q is 0 or 1 and —$R^4$ is —$CH_3$, —$CH_2CH_3$, or —F;
c) r is 0, 1 or 2, and —$R^B$ is $C_1$-$C_3$alkyl;
d) X is N, $R^2$ is -T-$Cy^2$, T is —$CH_2$— or —CO—; and $Cy^2$ is:

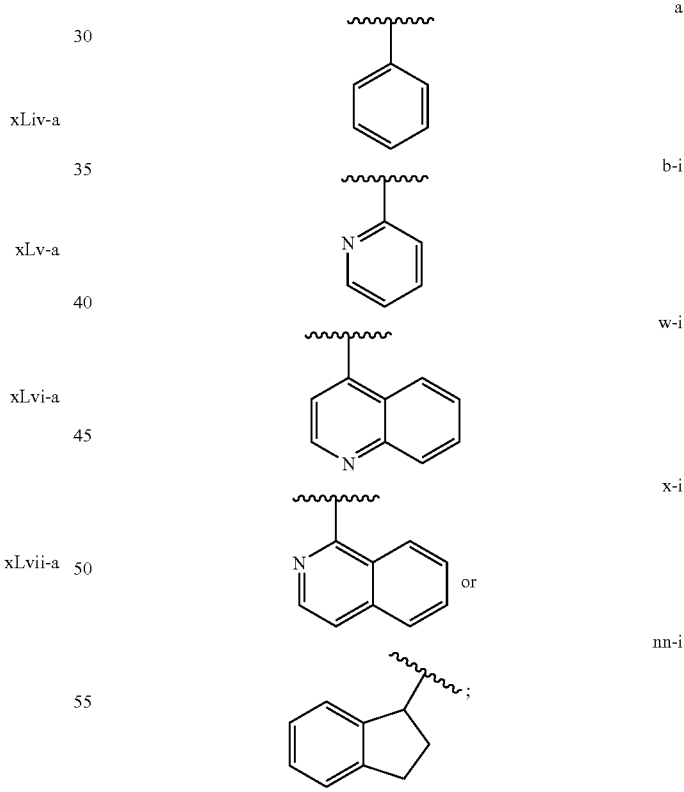

a b-i w-i x-i or nn-i wherein $Cy^2$ is substituted with 0, 1, or 2 occurrences of —$R^{6a}$ and each —$R^{6a}$, when present, is independently —Cl, —Br, —F, —CN, —$OCH_3$, —$OCH_2CH_3$, —$OCH_2CH_2CH_3$, —$CF_3$, —$CH_3$, —$CH_2CH_3$, —$CH_2CH_2CH_3$, —$CH(CH_3)_2$, —$C(CH_3)_3$, —COOH, —$COOCH_3$, —$COOCH_2CH_3$;

e) $Cy^1$ is selected from i, ii-a, ii-b, iii-a, iii-b, xxiv-a, xxiv-b, xxv-a, xxvi-a, xLiv-a, xLv-a, xLvi-a, or xLvii-a wherein Cy¹ is substituted with:

0, 1, or 2 occurrences of $R^{10a}$, and each —$R^{10a}$ is independently —Cl, —Br, —F, —$NO_2$, —CN, —$OCH_3$, —$OCH_2CH_3$, —$OCH_2CH_2CH_3$, —$CF_3$, —$OCF_3$, —$CH_3$, —$CH_2CH_3$, —$CH_2CH_2CH_3$, —$C(CH_3)_3$, —$CH(CH_3)_2$, t-Bu, —$NHCOCH_3$, —$NHCONHCH_3$, —$SCH_3$, —$SCH_2CH_3$, —$SCH_2CH_2CH_3$, —$NH_2$, —$NHCH_3$, —$SO_2NH_2$, —COOH, —$COOCH_3$, —$COOCH_2CH_3$, —$NHCH_3$, —$N(CH_3)_2$, —$NH(CH_2CH_3)$, —$N(CH_2CH_3)_2$, —$OC(CH_3)_2CO_2H$, —$OCH_2CO_2H$, —$C(CH_3)_2OH$, —$CONH_2$, —$NHCONH_2$, —$NHCON(CH_3)_2$, or —$NHCOOCH_3$, and 0 or 1 occurrence of —$R^{10b}$, J-$R^{10b}$, or W-J-$R^{10b}$, and —$R^{10b}$, J-$R^{10b}$, or W-J-$R^{10b}$ is morpholinyl, tetrazolyl,

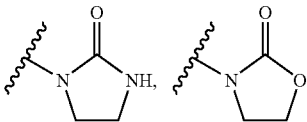

phenyl, benzyl, —NHCO(phenyl), —NHCO(benzyl), —NH(phenyl), —$NHCH_2$(phenyl), —NH(benzyl), —S(phenyl), —S(benzyl), —O(phenyl), or —O(benzyl), wherein the phenyl and benzyl groups are optionally substituted.

In still other embodiments, compounds of general formula II-A are provided

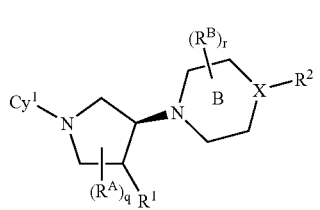

II-A wherein the substituents are selected from a) $R^1$ is —OH, —O($C_1$-$C_6$alkyl), halogen, —$OCOR^4$, —$NR^4SO_2R^3$, or —$NR^4COR^4$; q is 0, 1, or 2, and —$R^A$ is halogen, an optionally substituted linear or branched $C_1$-$C_6$alkyl, or an optionally substituted $C_3$-$C_6$cycloalkyl ring;

b) r is 0, 1, or 2, and —$R^B$ is halogen, or an optionally substituted group selected from $C_1$-$C_6$alkyl, $C_3$-$C_6$cycloalkyl, or a fused or bridged 5- or 6-membered saturated ring having 0 heteroatoms;

c) $R^2$ is -$Cy^2$ or -T-$Cy^2$, and when X is N, then T, when present, is —CO—, —$CH_2$—, —$CH_2CH=CH$—, or —$CH_2CH_2$—, or when X is $CR^8$, and T, when present, is —O— or —$NR^{5c}$—, and $R^8$ is hydrogen, $C_1$-$C_3$alkyl, —OH, —O($C_1$-$C_3$alkyl), —$NH_2$, —$N(C_1$-$C_3$alkyl)$_2$, —SH, —S($C_1$-$C_3$alkyl), —CO($C_1$-$C_3$alkyl), —COOH, or —COO($C_1$-$C_3$alkyl), $Cy^2$ is selected from phenyl, pyridyl, pyrimidinyl, pyrazinyl, pyridazinyl, 1,2,4-triazinyl, 1,3,5-triazinyl, 1,2,3-triazolyl, 1,2,4-triazolyl, imidazolyl, pyrazolyl, pyrrolyl, thiazolyl, isothiazolyl, thienyl, 1,3,4-thiadiazolyl, 1,2,4-thiadiazolyl, isoxazolyl, oxazolyl, furanyl, 1,3,4-oxadiazolyl, 1,2,4-oxadiazolyl, 1,3-dihydroimidazol-2-onyl, quinolinyl, isoquinolinyl, quinazolinyl, quinoxalinyl, [1,8]naphthyridinyl, naphthyl, 1,3-dihydro-benzoimidazol-2-on-1-yl, indolyl, benzo[c]isoxazolyl, benzofuranyl, benzothienyl, benzo[c]isothiazolyl, benzooxazol-2-yl, 5H-pyrrolo[3,2-d]pyrimidinyl, furo[3,2-d]pyrimidinyl, thieno[3,2-d]pyrimidinyl, indanyl, benzo[d]isothiazolyl, benzo[d]isoxazolyl, benzo[1,3]dioxolyl, benzothiazolyl, benzimidazolyl, or indazolyl; wherein $Cy^2$ is substituted with 0, 1, or 2 independent occurrences of —$R^{6a}$, -G-$R^{6a}$, or —V-G-$R^{6a}$, and 0 or 1 occurrence of =O, =S, =$NR^{7a}$, =$NR^{7b}$, —$R^{6b}$, -G-$R^{6b}$, or —V-G-$R^{6b}$, wherein:

each —$R^{6a}$, -G-$R^{6a}$, or —V-G-$R^{6a}$, when present, is independently —CN, —$NO_2$, —$OR^{7a}$, —$(CH_2)_{1-4}OR^{7a}$, —$SR^{7a}$, —$(CH_2)_{1-4}SR^{7a}$, halogen, —$COOR^{7a}$, —$(CH_2)_{1-4}COOR^{7a}$, —$COR^{7a}$, —$(CH_2)_{1-4}COR^{7a}$, —$CON(R^{7a})_2$, —$(CH_2)_{1-4}CON(R^{7a})_2$, —$N(R^{7a})_2$, —$(CH_2)_{1-4}N(R^{7a})_2$, —$SO_2N(R^{7a})_2$, —$(CH_2)_{1-4}SO_2N(R^{7a})_2$, —$NR^{7a}SO_2R^{7a}$, or —$(CH_2)_{1-4}NR^{7a}SO_2R^{7a}$, or an optionally substituted $C_1$-$C_6$aliphatic group; and each —$R^{6b}$, -G-$R^{6b}$, or —V-G-$R^{6b}$ is —$OR^{7b}$, —$(CH_2)_{1-4}OR^{7b}$, —$SR^{7b}$, —$(CH_2)_{1-4}SR^{7b}$, —$COOR^{7b}$, —$(CH_2)_{1-4}COOR^{7b}$, —$COR^{7b}$, —$(CH_2)_{1-4}COR^{7b}$, —$CON(R^{7b})(R^{7c})$, —$(CH_2)_{1-4}CON(R^{7b})(R^{7c})$, —$N(R^{7b})(R^{7c})$, —$(CH_2)_{1-4}N(R^{7b})(R^{7c})$, —$SO_2N(R^{7b})(R^{7c})$, —$(CH_2)_{1-4}SO_2N(R^{7b})(R^{7c})$, —$NR^{7c}SO_2R^{7b}$, —$(CH_2)_{1-4}NR^{7c}SO_2R^{7b}$, or an optionally substituted group selected from a 3-7-membered saturated, partially saturated, or aromatic monocyclic ring having 0-3 heteroatoms independently selected from nitrogen, oxygen, or sulfur, or an 8-10-membered saturated, partially unsaturated, or aromatic bicyclic ring having 0-5 heteroatoms independently selected from nitrogen, oxygen, or sulfur; and d) $Cy^1$ is selected from phenyl, pyridyl, pyrimidinyl, pyrazinyl, pyridazinyl, 1,2,4-triazinyl, 1,3,5-triazinyl, 1,2,3-triazolyl, 1,2,4-triazolyl, imidazolyl, pyrazolyl, pyrrolyl, thiazolyl, isothiazolyl, thienyl, 1,3,4-thiadiazolyl, 1,2,4-thiadiazolyl, isoxazolyl, oxazolyl, furanyl, 1,3,4-oxadiazolyl, 1,2,4-oxadiazolyl, 1,3-dihydroimidazol-2-onyl, quinolinyl, isoquinolinyl, quinazolinyl, quinoxalinyl, [1,8]naphthyridinyl, naphthyl, 1,3-dihydro-benzoimidazol-2-on-1-yl, indolyl, benzo[c]isoxazolyl, benzofuranyl, benzothienyl, benzo[c]isothiazolyl, benzooxazol-2-yl, 5H-pyrrolo[3,2-d]pyrimidinyl, furo[3,2-d]pyrimidinyl, thieno[3,2-d]pyrimidinyl, indanyl, benzo[d]isothiazolyl, benzo[d]isoxazolyl, benzo[1,3]dioxolyl, benzothiazolyl, benzimidazolyl, indazolyl, purinyl, pyrido[2,3-d]pyrimidine, or pyrido[3,4-d]pyrimidine; wherein $Cy^1$ is substituted with 0, 1, 2, or 3 independent occurrences of —$R^{10a}$, -J-$R^{10a}$, or —W-J-$R^{10a}$, and 0 or 1 occurrence of =O, =S, =$NR^{11a}$, =$NR^{11b}$, —$R^{10b}$, -J-$R^{10b}$, or —W-J-$R^{10b}$, wherein:

each —$R^{10a}$, -J-$R^{10a}$, or —W-J-$R^{10a}$, when present, is independently —CN, —$NO_2$, —$OR^{11a}$, —$(CH_2)_{1-4}OR^{11a}$, —$SR^{11a}$, —$(CH_2)_{1-4}SR^{11a}$, halogen, —$COOR^{11a}$, —$(CH_2)_{1-4}COOR^{11a}$, —$COR^{11a}$, —$(CH_2)_{1-4}COR^{11a}$, —$CON(R^{11a})_2$, —$(CH_2)_{1-4}CON(R^{11a})_2$, —$N(R^{11a})_2$, —$(CH_2)_{1-4}N(R^{11a})_2$, —$SO_2N(R^{11a})_2$, —$(CH_2)_{1-4}SO_2N(R^{11a})_2$, —$NR^{11a}SO_2R^{11a}$, —$(CH_2)_{1-4}NR^{11a}SO_2R^{11a}$, —$NR^{11a}CON(R^{11a})_2$, —$(CH_2)_{1-4}NR^{11a}CON(R^{11a})_2$, —$NR^{11a}COOR^{11a}$, —$(CH_2)_{1-4}NR^{11a}COOR^{11a}$, or an optionally substituted $C_1$-$C_6$aliphatic group; and each —$R^{10b}$, -J-$R^{10b}$, or —W-J-$R^{10b}$ is —$OR^{11b}$, —$(CH_2)_{1-4}OR^{11b}$, —$SR^{11b}$, —$(CH_2)_{1-4}SR^{11b}$, —$COOR^{11b}$, —$(CH_2)_{1-4}COOR^{11b}$, —$COR^{11b}$, —$(CH_2)_{1-4}COR^{11b}$, —$CON(R^{11b})(R^{11c})$, —$(CH_2)_{1-4}CON(R^{11b})(R^{11c})$, —$N(R^{11b})(R^{11c})$, —$(CH_2)_{1-4}N(R^{11b})(R^{11c})$, —$SO_2N(R^{11b})(R^{11c})$, —$(CH_2)_{1-4}SO_2N(R^{11b})(R^{11c})$, —$NR^{11c}SO_2R^{11b}$, —$(CH_2)_{1-4}NR^{11c}SO_2R^{11b}$, —$NR^{11c}CON(R^{11b})(R^{11c})$, —$(CH_2)_{1-4}NR^{11c}CON(R^{11b})(R^{11c})$, —$NR^{11c}COOR^{11b}$, —$(CH_2)_{1-4}NR^{11c}COOR^{11b}$, or an optionally substituted group selected from a 3-7-membered saturated, partially saturated, or aromatic monocyclic ring having 0-3 heteroatoms independently selected from nitrogen, oxygen, or sulfur, or an 8-10-membered saturated, partially unsaturated, or aromatic bicyclic ring having 0-5 heteroatoms independently selected from nitrogen, oxygen, or sulfur.

In yet other embodiments, compounds of formula II-A-i are provided

II-A-i

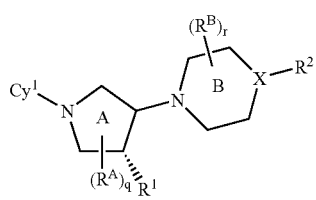

and substituents are further selected from a) $R^1$ is —OH, —O($C_1$-$C_6$alkyl), halogen, —OCOR$^4$, —NR$^4$SO$_2$R$^3$, or —NR$^4$COR$^4$; q is 0, 1, or 2, and —R$^A$ is halogen, an optionally substituted linear or branched $C_1$-$C_6$alkyl, or an optionally substituted $C_3$-$C_6$cycloalkyl ring;

b) r is 0, 1, or 2, and —R$^B$ is —R$^B$ is $C_1$-$C_3$alkyl, or two occurrences of R$^B$, taken together with their intervening atom(s), form an optionally substituted fused or bridged 5 or 6-membered saturated, partially unsaturated, or aromatic ring having 0 heteroatoms;

c) $Cy^2$ is:

a

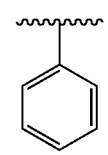

b-i

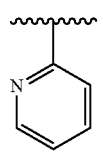

b-ii

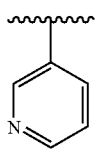

c-i

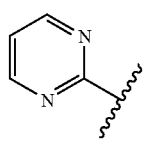

l-i

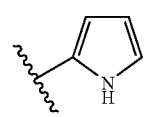

-continued l-ii

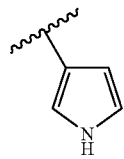

n-i

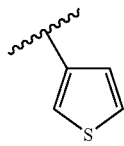

n-ii

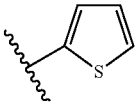

s-i

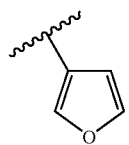

s-ii

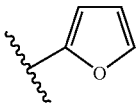

w-i

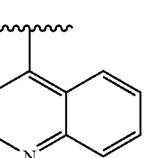

x-i

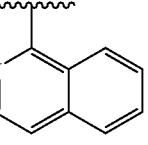

bb-i

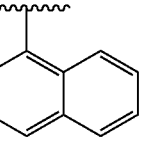

cc

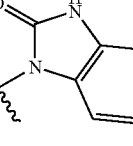

mm-i

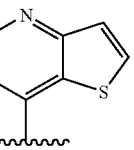

-continued

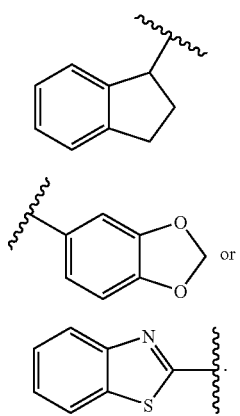
nn-i

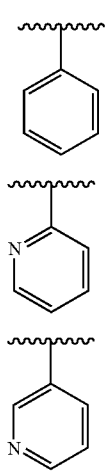 or
qq-i

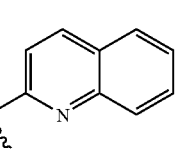
rr wherein Cy² is substituted with:

0, 1, or 2 occurrences of —R⁶ᵃ and each —R⁶ᵃ, when present, is independently —Cl, —Br, —F, —CN, —NO₂, —OR⁷ᵃ, —SR⁷ᵃ, —N(R⁷ᵃ)₂, —COOR⁷ᵃ, —COR⁷ᵃ, —SO₂N(R⁷ᵃ)₂, —NR⁷ᵃSO₂R⁷ᵃ, —CON(R⁷ᵃ)₂, —NR⁷ᵃCOR⁷ᵃ, or optionally substituted C₁-C₆alkyl, wherein each R⁷ᵃ is independently hydrogen, or optionally substituted C₁-C₆alkyl; and 0 or 1 occurrence of —R⁶ᵇ, wherein —R⁶ᵇ, when present is —OR⁷ᵇ, —SR⁷ᵇ, —N(R⁷ᵇ)(R⁷ᶜ), —COOR⁷ᵇ, —COR⁷ᵇ, —SO₂N(R⁷ᵇ)(R⁷ᶜ), —NR⁷ᶜSO₂R⁷ᵇ, —CON(R⁷ᵇ)(R⁷ᶜ), —NR⁷ᶜCOR⁷ᵇ, or an optionally substituted 3-6-membered saturated, partially unsaturated, or aromatic ring having 0-3 heteroatoms independently selected from nitrogen, oxygen, or sulfur, wherein each R⁷ᵇ is independently an optionally substituted 3-6-membered saturated, partially unsaturated, or aromatic ring having 0-3 heteroatoms independently selected from nitrogen, oxygen, or sulfur, and each R⁷ᶜ is independently hydrogen or an optionally substituted group selected from C₁-C₆alkyl or an optionally substituted 3-6-membered saturated, partially unsaturated, or aromatic ring having 0-3 heteroatoms independently selected from nitrogen, oxygen, or sulfur; and d) Cy¹ is:

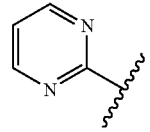
i

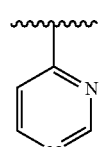
ii-a

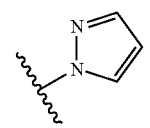
ii-b

-continued

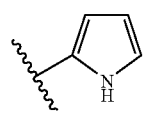
iii-a

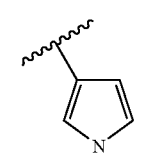
iii-b

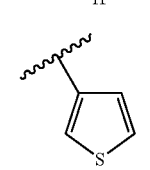
xi-a

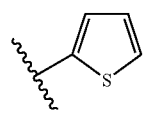
xii-a

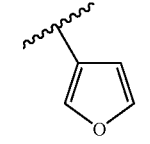
xii-b

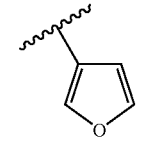
xv-a

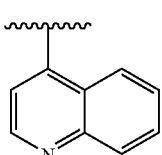
xv-b

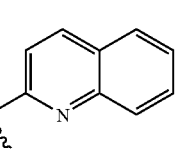
xx-a xx-b xxiv-a xxiv-b

-continued

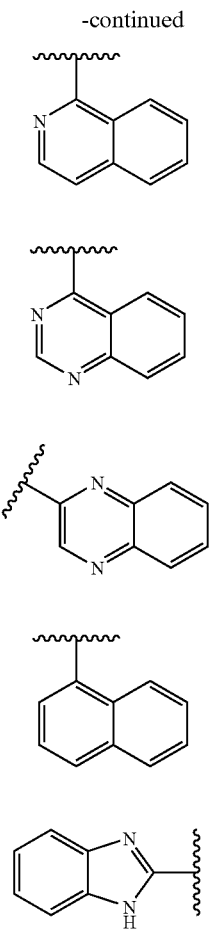

xxv-a xxvi-a xxvii-a xxxix xLiv-a xLv-a xLvi-a xLvii-a

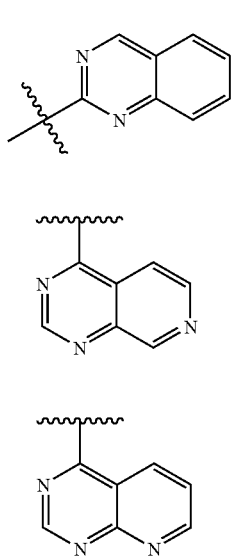

wherein Cy$^1$ is substituted with:

0, 1, or 2 occurrences of —R$^{10a}$ and each —R$^{10a}$, when present, is independently —Cl, —Br, —F, —CN, —NO$_2$, —OR$^{11a}$, —SR$^{11a}$, —N(R$^{11a}$)$_2$, —NR$^{11a}$COR$^{11a}$, —CON(R$^{11a}$)$_2$, —SO$_2$N(R$^{11a}$)$_2$, —NR$^{11a}$SO$_2$R$^{11a}$, COOR$^{11a}$, COR$^{11a}$, —NR$^{11a}$CON(R$^{11a}$)$_2$, —NR$^{11a}$COOR$^{11a}$, or optionally substituted C$_1$-C$_6$alkyl, wherein each R$^{11a}$ is independently hydrogen, or optionally substituted C$_1$-C$_6$alkyl; and 0 or 1 occurrence of —R$^{10b}$, J-R$^{10b}$, or W-J-R$^{10b}$, wherein W is —N(R$^{11b}$) or —O—, J is a C$_1$-C$_2$alkyl chain, and —R$^{10b}$, when present is —OR$^{11b}$, —SR$^{11b}$, —N(R$^{11b}$)(R$^{11c}$), —NR$^{11c}$COR$^{11b}$, CON(R$^{11b}$)(R$^{11c}$), —SO$_2$N(R$^{11c}$)(R$^{11b}$), —NR$^{11c}$SO$_2$R$^{11b}$, —COOR$^{11b}$, COR$^{11b}$, —NR$^{11c}$CON(R$^{11b}$)(R$^{11c}$), —NR$^{11c}$COOR$^{11b}$, or an optionally substituted 3-6-membered saturated, partially unsaturated, or aromatic ring having 0-3 heteroatoms independently selected from nitrogen, oxygen, or sulfur, wherein each R$^{11b}$ is independently an optionally substituted 3-6-membered saturated, partially unsaturated, or aromatic ring having 0-3 heteroatoms independently selected from nitrogen, oxygen, or sulfur, and each R$^{11c}$ is independently hydrogen or an optionally substituted group selected from C$_1$-C$_6$alkyl or an optionally substituted 3-6-membered saturated, partially unsaturated, or aromatic ring having 0-3 heteroatoms independently selected from nitrogen, oxygen, or sulfur.

In still other embodiments, for the subsets of compounds of formulae II-A and II-A-i described directly above, each of the substituents are further selected from:

a) q is 0 or 1 and ring A has the structure:

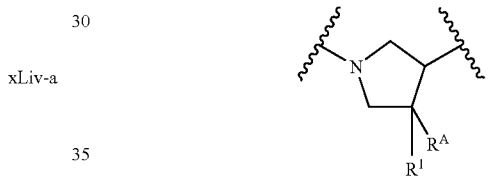

wherein R$^1$ is —OR$^4$, and —R$^A$ is —CH$_3$, CH$_2$CH$_3$, or F;

b) r is 0, 1, or 2, and —R$^B$ is methyl;

c) R$^2$ is -Cy$^2$, or -T-Cy$^2$, and when X is N, then T, when present, is —CO— or —CH$_2$—, or when X is CR$^8$, then T, when present, is —O— or —NR$^{5c}$—, and R$^8$ is hydrogen, C$_1$-C$_3$alkyl, —OH, or —O(C$_1$-C$_3$alkyl);

d) Cy$^2$ is:

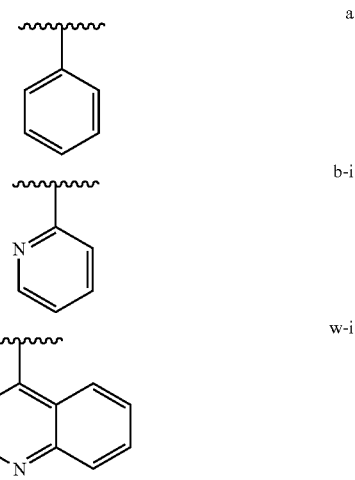

a b-i w-i

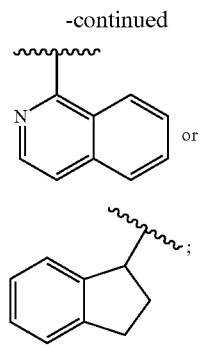

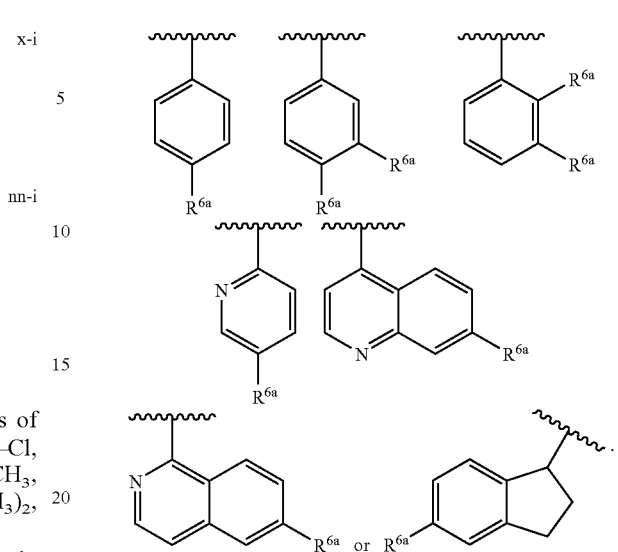

wherein Cy² is substituted with 0, 1, or 2 occurrences of —R⁶ᵃ and each —R⁶ᵃ, when present, is independently —Cl, —Br, —F, —CN, —OCH₃, —OCH₂CH₃, —OCH₂CH₂CH₃, —CF₃, —CH₃, —CH₂CH₃, —CH₂CH₂CH₃, —CH(CH₃)₂, —C(CH₃)₃, —COOH, —COOCH₃, —COOCH₂CH₃;

e) Cy¹ is selected from i, ii-a, ii-b, iii-a, iii-b, xxiv-a, xxiv-b, xxv-a, xxvi-a, xLiv-a, xLv-a, xLvi-a, or xLvii-a wherein Cy¹ is substituted with:

0, 1, or 2 occurrences of R¹⁰ᵃ, and each —R¹⁰ᵃ is independently —Cl, —Br, —F, —NO₂, —CN, —OCH₃, —OCH₂CH₃, —OCH₂CH₂CH₃, —CF₃, —OCF₃, —CH₃, —CH₂CH₃, —CH₂CH₂CH₃, —C(CH₃)₃, —CH(CH₃)₂, t-Bu —NHCOCH₃, —NHCONHCH₃, —SCH₃, —SCH₂CH₃, —SCH₂CH₂CH₃, —NH₂, —NHCH₃, —SO₂NH₂, —COOH, —COOCH₃, —COOCH₂CH₃, —NHCH₃, —N(CH₃)₂, —NH(CH₂CH₃), —N(CH₂CH₃)₂, —OC(CH₃)₂CO₂H, —OCH₂CO₂H, —C(CH₃)₂OH, —CONH₂, —NH-CONH₂, —NHCON(CH₃)₂, or —NHCOOCH₃, and 0 or 1 occurrence of —R¹⁰ᵇ, J-R¹⁰ᵇ, or W-J-R¹⁰ᵇ, and —R¹⁰ᵇ, J-R¹⁰ᵇ, or W-J-R¹⁰ᵇ is morpholinyl, tetrazolyl,

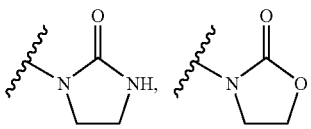

phenyl, benzyl, —NHCO(phenyl), —NHCO(benzyl), —NH(phenyl), —NHCH₂(phenyl), —NH(benzyl), —S(phenyl), —S(benzyl), —O(phenyl), or —O(benzyl), wherein the phenyl and benzyl groups are optionally substituted.

In yet other embodiments, for the subsets of compounds of formulae II-A and II-A-i described directly above, R¹ is —OH.

In still other embodiments, for the subsets of compounds of formulae II-A and II-A-i described directly above, q is 0.

In other embodiments, for the subsets of compounds of formulae II-A and II-A-i described directly above, r is 0.

In still other embodiments, for the subsets of compounds of formulae II-A and II-A-i described directly above, Cy² is substituted with 1 or 2 occurrences of —R⁶ᵃ, and each —R⁶ᵃ, is independently —Cl, —F, —CF₃, —CH₃, or —Br.

In yet other embodiments, for the subsets of compounds of formulae II-A and II-A-i described directly above, Cy² is substituted with 1 occurrence of —R⁶ᵃ, and —R⁶ᵃ is —Cl.

In other embodiments, for the subsets of compounds of formulae II-A and II-A-i described directly above, Cy² is:

and each R⁶ᵃ is independently —Cl, —Br, —CH₃, —CF₃, or —F.

In other embodiments, for the subsets of compounds of formulae II-A and II II-A-i described directly above, Cy² is phenyl substituted with 1 or 2 occurrences of —R⁶ᵃ, and each —R⁶ᵃ is independently —Cl, —F, —CF₃, —CH₃, or —Br.

In still other embodiments, for the subsets of compounds of formulae II-A and II-A-i described directly above, Cy² is phenyl substituted with 1 occurrence of —R⁶ᵃ, and —R⁶ᵃ is —Cl.

In other embodiments, for the subsets of compounds of formulae II-A and II-A-i described directly above, Cy¹ is an optionally substituted group selected from 2-pyridyl (ii-a), pyrimidin-2-yl (iii-a), pyrimidin-4-yl (iii-b), quinolinyl (xxiv-a), or 4-quinaozlinyl (xxvi-a) 2-quinazolinyl (xLv-a), pyrido[2,3-d]pyrimidinyl (xLvi-a) or pyrido[3,4-d]pyrimidinyl (xLvii-a).

In other embodiments, Cy¹ is an optionally substituted group selected from 2-pyridyl (ii-a), pyrimidin-2-yl (iii-a), or 4-quinazolinyl (xxvi-a) or 2-quinazolinyl (xLv-a).

In still other embodiments, Cy¹ is an optionally substituted group selected from pyrido[2,3-d]pyrimidinyl (xLvi-a) or pyrido[3,4-d]pyrimidinyl (xLvii-a).

In other embodiments, Cy¹ is substituted with 1, 2, or 3 occurrences of R¹⁰ᵃ, and each R¹⁰ᵃ is independently —Cl, —Br, —F, —CH₃, —CF₃, —COOCH₃, —CONH₂, —NHCONH₂, —NHCOOCH₃, —NHCONHCH₃, —CONHCH₃, —C(CH₃)₂OH, —OCH₃, —OCH₂CH₃, —CN, -tetrazole, —NO₂, —N(CH₃)₂, -or COOH.

In yet other embodiments, j is 0 or 1, and p is 0, 1, 2, or 3, and each —R¹⁰ᵃ is independently —COOCH₃, —CONH₂, —OCH₃, —Cl, —Br, —F, or —CF₃, and —R¹⁰ᵇ is optionally substituted phenyl.

Representative examples of compounds are set forth below in Table 1. Compounds can be prepared as an enantiomeric mixture of the (3R,4R and 3S,4S)-trans-4-piperazinylpyrrolidin-3-ol, or can be separated to provide both the (3R, 4R) and (3S, 4S) compounds. For certain compounds in Table 1, the (3R, 4R) and (3S, 4S) enantiomers are specifically designated.

TABLE 1

Examples of Compounds of Formula I-A

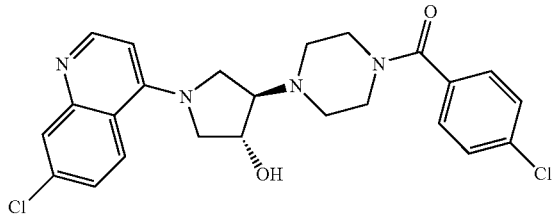

1
4-[4-(4-chlorobenzoyl)piperazin-1-yl]-1-(7-chloroquinolin-4-yl)pyrrolidin-3-ol

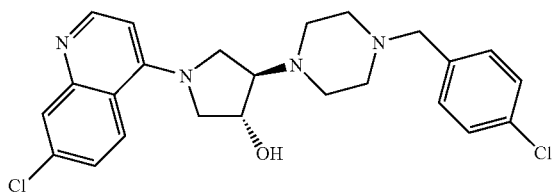

2
4-[4-(4-chlorobenzyl)piperazin-1-yl]-1-(7-chloroquinolin-4-yl)pyrrolidin-3-ol

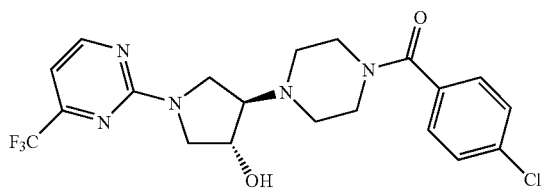

3
4-[4-(4-chlorobenzoyl)piperazin-1-yl]-1-[4-(trifluoromethyl)pyrimidin-2-yl]pyrrolidin-3-ol

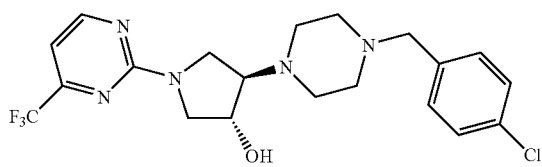

4
4-[4-(4-chlorobenzyl)piperazin-1-yl]-1-[4-(trifluoromethyl)pyrimidin-2-yl]pyrrolidin-3-ol

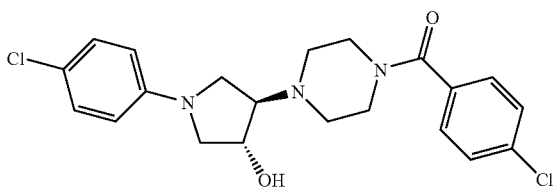

5
4-[4-(4-chlorobenzoyl)piperazin-1-yl]-1-(4-chlorophenyl)pyrrolidin-3-ol

TABLE 1-continued

Examples of Compounds of Formula I-A

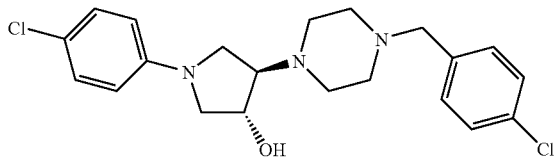

6
4-[4-(4-chlorobenzyl)piperazin-1-yl]-1-(4-chlorophenyl)pyrrolidin-3-ol

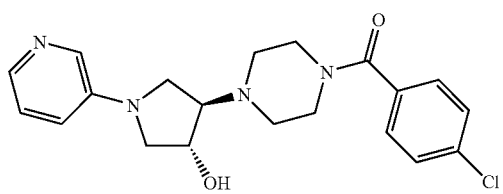

7
4-[4-(4-chlorobenzoyl)piperazin-1-yl]-1-pyridin-3-ylpyrrolidin-3-ol

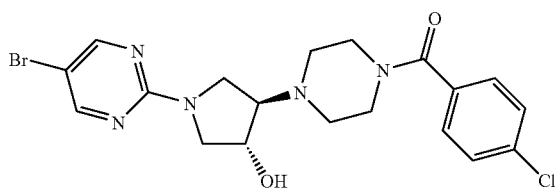

8
1-(5-bromopyrimidin-2-yl)-4-[4-(4-chlorobenzoyl)piperazin-1-yl]pyrrolidin-3-ol

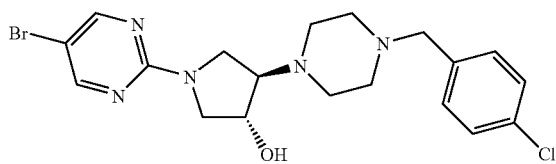

9
1-(5-bromopyrimidin-2-yl)-4-[4-(4-chlorobenzyl)piperazin-1-yl]pyrrolidin-3-ol

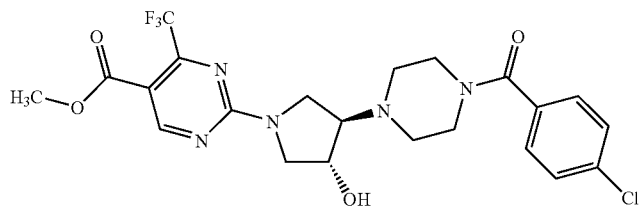

10
methyl 2-{3-[4-(4-chlorobenzoyl)piperazin-1-yl]4-hydroxypyrrolidin-1-yl}-4-(trifluoromethyl)pyrimidine-5-carboxylate TABLE 1-continued Examples of Compounds of Formula I-A

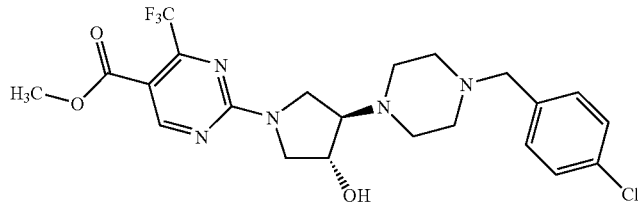

11
methyl 2-{3-[4-(4-chlorobenzyl)piperazin-1-
yl]-4-hydroxypyrrolidin-1-yl}-4-
(trifluoromethyl)pyrimidine-5-carboxylate

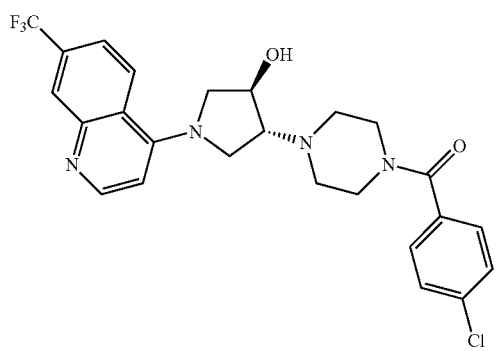

12
4-[4-(4-chlorobenzoyl)piperazin-1-yl]-1-[7-
(trifluoromethyl)quinolin-4-yl]pyrrolidin-3-
ol

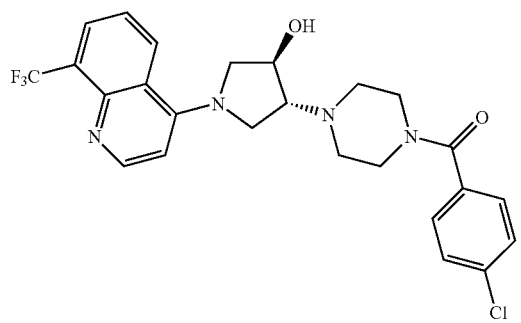

13
4-[4-(4-chlorobenzoyl)piperazin-1-yl]-1-[8-
(trifluoromethyl)quinolin-4-yl]pyrrolidin-3-
ol

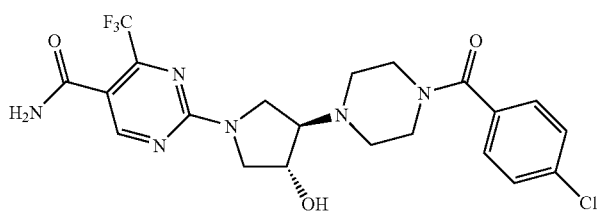

14
2-{3-[4-(4-chlorobenzoyl)piperazin-1-yl]-4-
hydroxypyrrolidin-1-yl}-4-
(trifluoromethyl)pyrimidine-5-carboxamide TABLE 1-continued Examples of Compounds of Formula I-A

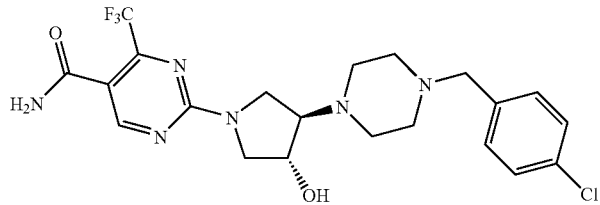

15
2-{3-[4-(4-chlorobenzyl)piperazin-1-yl]-4-
hydroxypyrrolidin-1-yl}-4-
(trifluoromethyl)pyrimidine-5-carboxamide

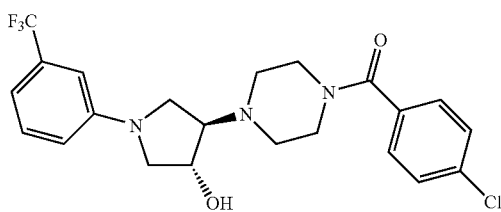

16
4-[4-(4-chlorobenzoyl)piperazin-1-yl]-1-[3-
(trifluoromethyl)phenyl]pyrrolidin-3-ol

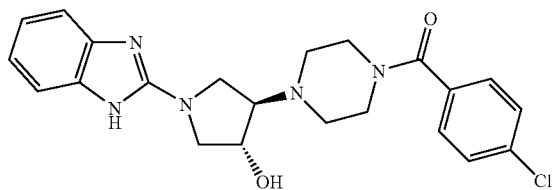

17
1-(1H-benzimidazol-2-yl)-4-[4-(4-
chlorobenzoyl)piperazin-1-yl]pyrrolidm-3-ol

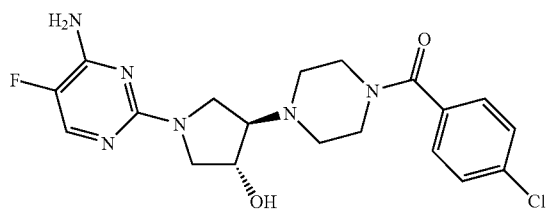

18
1-(4-amino-5-fluoropyrimidin-2-yl)-4-[4-(4-
chlorobenzoyl)piperazin-1-yl]pyrrolidin-3-ol

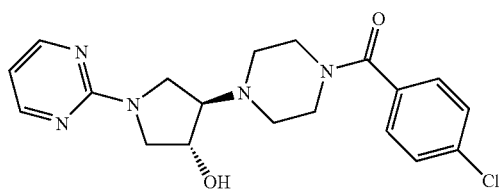

19
4-[4-(4-chlorobenzoyl)piperazin-1-yl]-1-
pyrimidin-2-ylpyrrolidin-3-ol

TABLE 1-continued
Examples of Compounds of Formula I-A
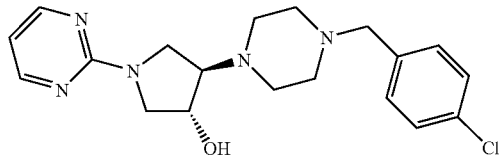
20
4-[4-(4-chlorobenzyl)piperazin-1-yl]-1-
pyrimidin-2-ylpyrrolidin-3-ol
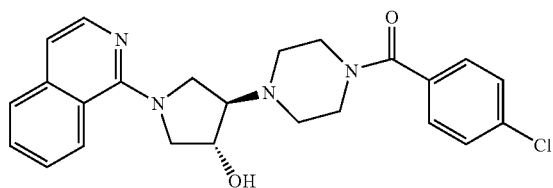
21
4-[4-(4-chlorobenzoyl)piperazin-1-yl]-1-
isoquinolin-1-ylpyrrolidin-3-ol
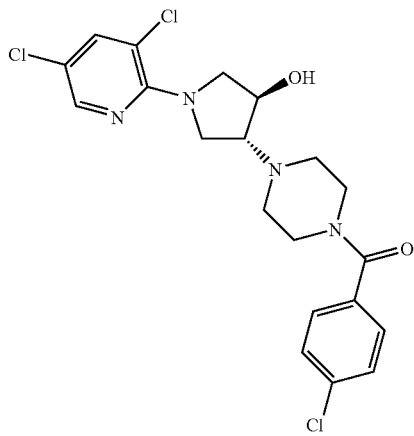
22
4-[4-(4-chlorobenzoyl)piperazin-1-yl]-1-(3,5-
dichloropyridin-2-yl)pyrrolidin-3-ol
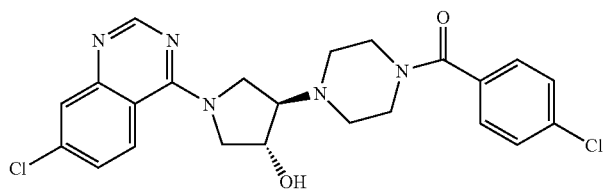
23
4-[4-(4-chlorobenzoyl)piperazin-1-yl]-1-(7-
chloroquinazolin-4-yl)pyrrolidin-3-ol TABLE 1-continued
Examples of Compounds of Formula I-A
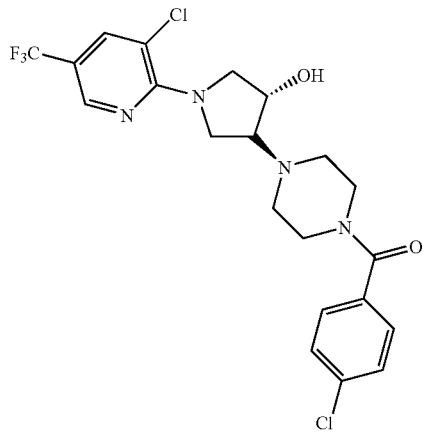
24
4-[4-(4-chlorobenzoyl)piperazin-1-yl]-1-[3-
chloro-5-(trifluoromethyl)pyridin-2-
yl]pyrrolidin-3-ol
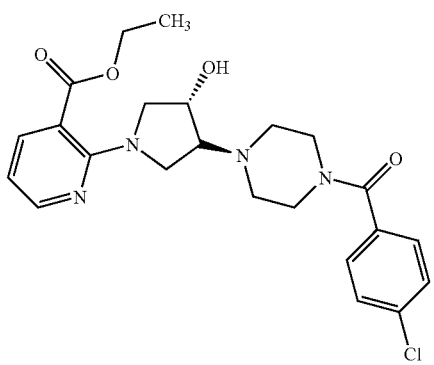
25
ethyl 2-{3-[4-(4-chlorobenzoyl)piperazin-1-
yl]-4-hydroxypyrrolidin-1-yl}nicotinate
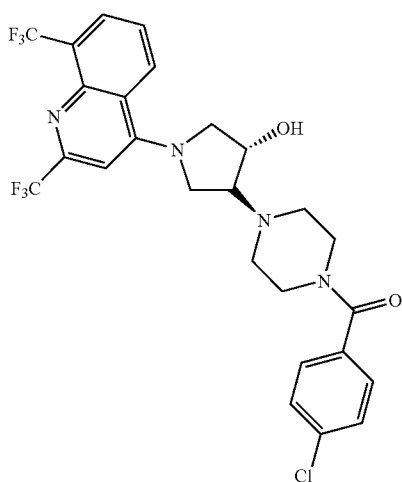
26
1-[2,8-bis(trifluoromethyl)quinolin-4-yl]-4-
[4-(4-chlorobenzoyl)piperazin-1-
yl]pyrrolidin-3-ol TABLE 1-continued Examples of Compounds of Formula I-A

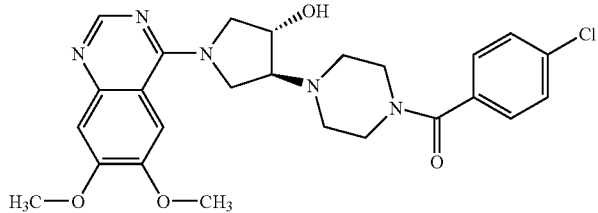

27
4-[4-(4-chlorobenzoyl)piperazin-1-yl]-1-(6,7-
dimethoxyquinazolin-4-yl)pyrrolidin-3-ol

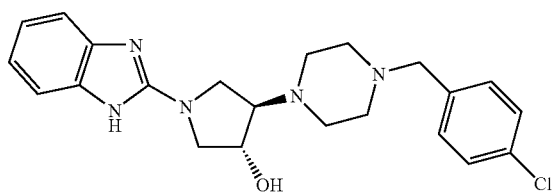

28
1-(1H-benzimidazol-2-yl)-4-[4-(4-
chlorobenzyl)piperazin-1-yl]pyrrolidin-3-ol

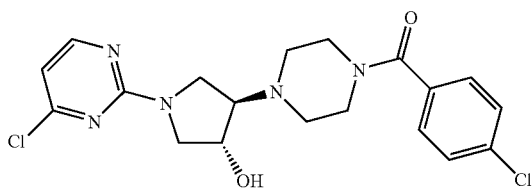

29
4-[4-(4-chlorobenzoyl)piperazin-1-yl]-1-(4-
chloropyrimidin-2-yl)pyrrolidin-3-ol

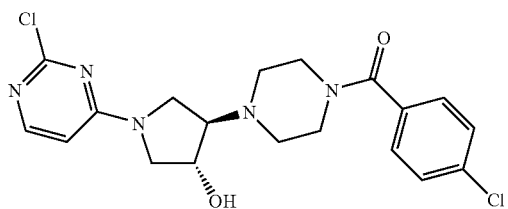

30
4-[4-(4-chlorobenzoyl)piperazin-1-yl]-1-(2-
chloropyrimidin-4-yl)pyrrolidin-3-ol

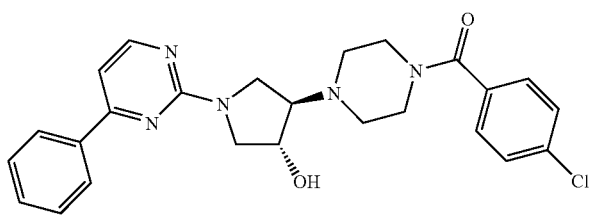

31
4-[4-(4-chlorobenzoyl)piperazin-1-yl]-1-(4-
phenylpyrimidin-2-yl)pyrrolidin-3-ol TABLE 1-continued
Examples of Compounds of Formula I-A
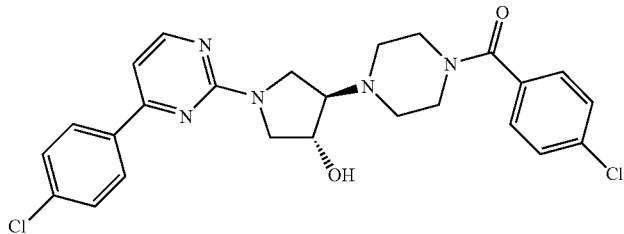
32
4-[4-(4-chlorobenzoyl)piperazin-1-yl]-1-[4-
(4-chlorophenyl)pyrimidin-2-yl]pyrrolidin-3-
ol
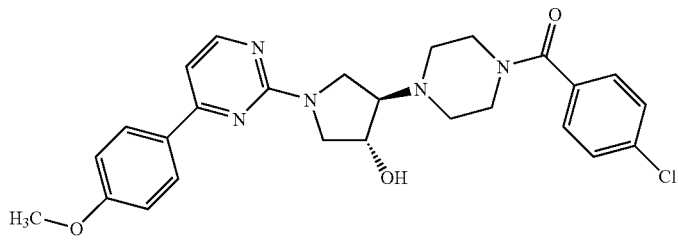
33
4-[4-(4-chlorobenzoyl)piperazin-1-yl]-1-[4-
(4-methoxyphenyl)pyrimidin-2-yl]pyrrolidin-
3-ol
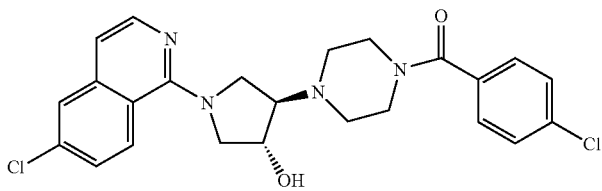
34
4-[4-(4-chlorobenzoyl)piperazin-1-yl]-1-(6-
chloroisoquinolin-1-yl)pyrrolidin-3-ol
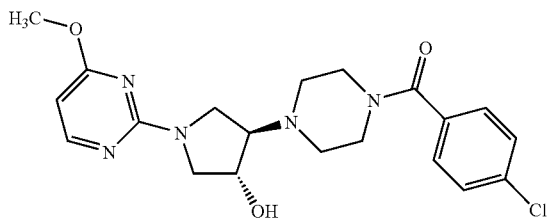
35
4-[4-(4-chlorobenzoyl)piperazin-1-yl]-1-(4-
methoxypyrimidin-2-yl)pyrrolidin-3-ol TABLE 1-continued
Examples of Compounds of Formula I-A
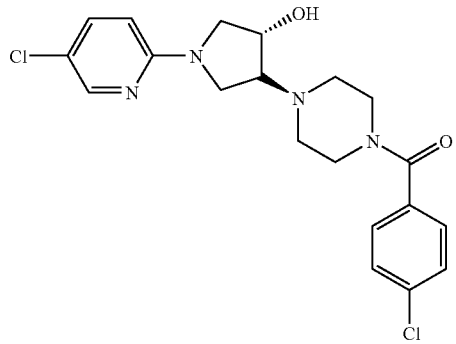
36
4-[4-(4-chlorobenzoyl)piperazin-1-yl]-1-(5-chloropyridin-2-yl)pyrrolidin-3-ol
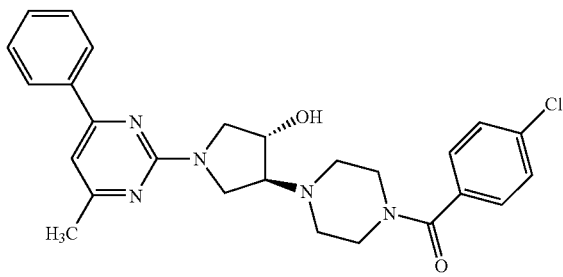
37
4-[4-(4-chlorobenzoyl)piperazin-1-yl]-1-(4-methyl-6-phenylpyrimidin-2-yl)pyrrolidin-3-ol
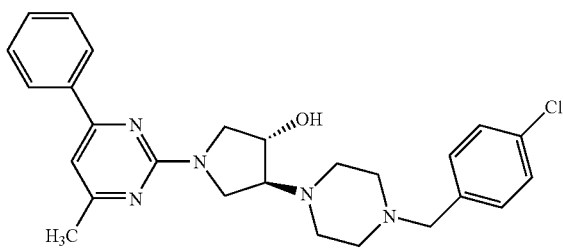
38
4-[4-(4-chlorobenzyl)piperazin-1-yl]-1-(4-methyl-6-phenylpyrimidin-2-yl)pyrrolidin-3-ol
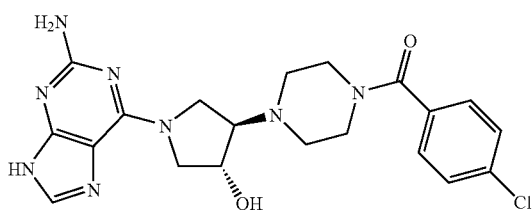
39
1-(2-amino-9H-purin-6-yl)-4-[4-(4-chlorobenzoyl)piperazin-1-yl]pyrrolidin-3-ol TABLE 1-continued Examples of Compounds of Formula I-A

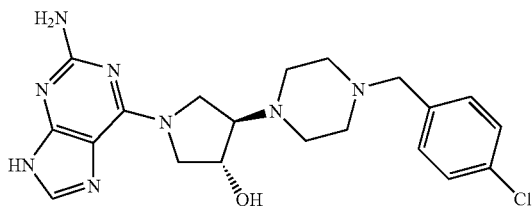

40
1-(2-amino-9H-purin-6-yl)-4-[4-(4-chlorobenzyl)piperazin-1-yl]pyrrolidin-3-ol

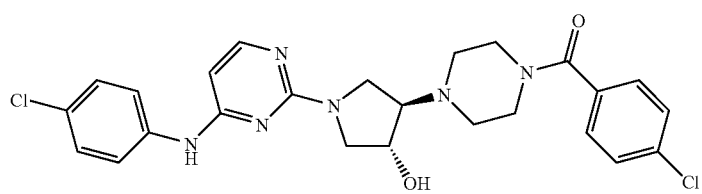

41
4-[4-(4-chlorobenzoyl)piperazin-1-yl]-1-{4-[(4-chlorophenyl)amino]pyrimidin-2-yl}pyrrolidin-3-ol

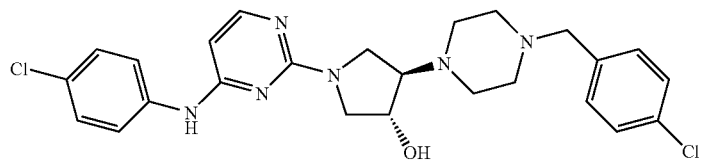

42
4-[4-(4-chlorobenzyl)piperazin-1-yl]-1-{4-[(4-chlorophenyl)amino]pyrimidin-2-yl}pyrrolidin-3-ol

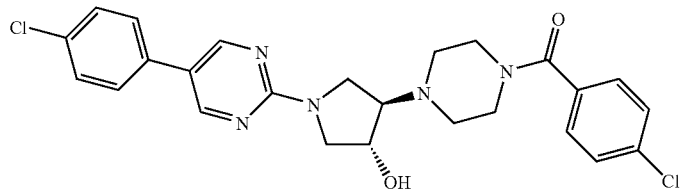

43
4-[4-(4-chlorobenzoyl)piperazin-1-yl]-1-[5-(4-chlorophenyl)pyrimidin-2-yl]pyrrolidin-3-ol

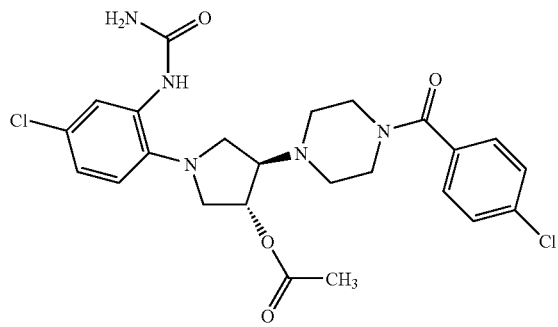

44
4-[4-(4-chlorobenzoyl)piperazin-1-yl]-1-[5-(4-chlorophenyl)pyrimidin-2-yl]pyrrolidin-3-ol TABLE 1-continued
Examples of Compounds of Formula I-A
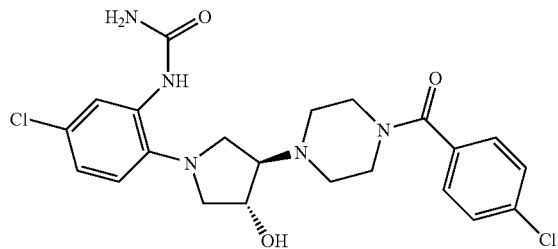
45
N-(5-chloro-2-{3-[4-(4-
chlorobenzoyl)piperazin-1-yl]-4-
hydroxypyrrolidin-1-yl}phenyl)urea
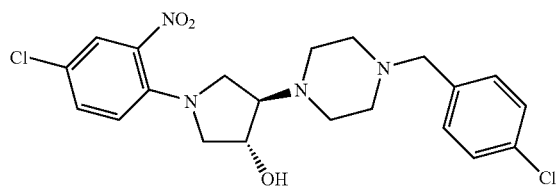
46
4-[4-(4-chlorobenzyl)piperazin-1-yl]-1-(4-
chloro-2-nitrophenyl)pyrrolidin-3-ol
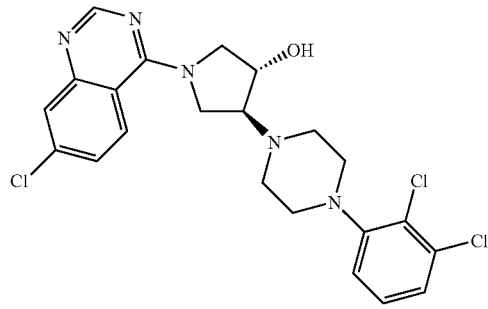
47
1-(7-chloroquinazolin-4-yl)-4-[4-(2,3-
dichlorophenyl)piperazin-1-yl]pyrrolidin-3-
ol
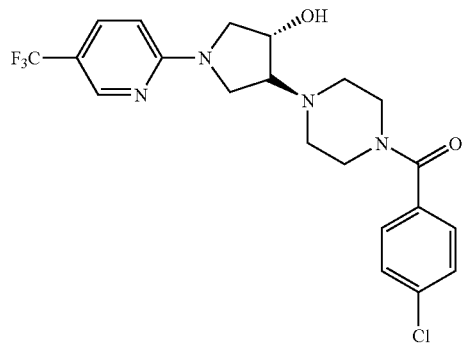
48
4-[4-(4-chlorobenzoyl)piperazin-1-yl]-1-[5-
(trifluoromethyl)pyridin-2-yl]pyrrolidin-3-ol TABLE 1-continued Examples of Compounds of Formula I-A

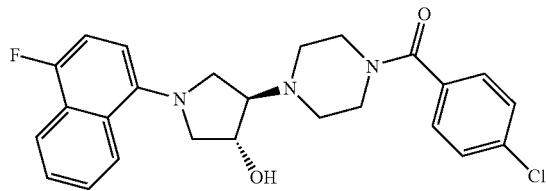

49
4-[4-(4-chlorobenzoyl)piperazin-1-yl]-1-(4-fluoro-1-naphthyl)pyrrolidin-3-ol

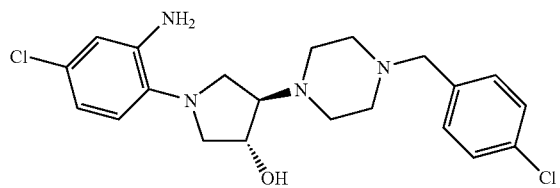

50
1-(2-aimno-4-chlorophenyl)-4-[4-(4-chlorobenzyl)piperazin-1-yl]pyrrolidin-3-ol

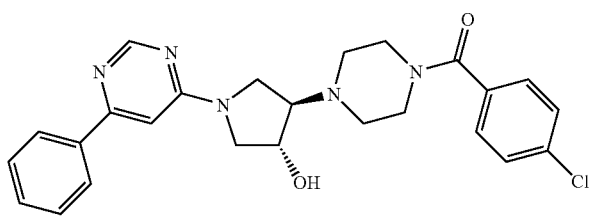

51
4-[4-(4-chlorobenzoyl)piperazin-1-yl]-1-(6-phenylpyrimidin-4-yl)pyrrolidin-3-ol

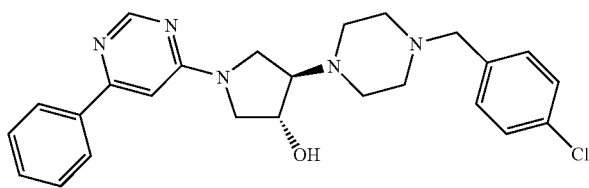

52
4-[4-(4-chlorobenzyl)piperazin-1-yl]-1-(6-phenylpyrimidin-4-yl)pyrrolidin-3-ol

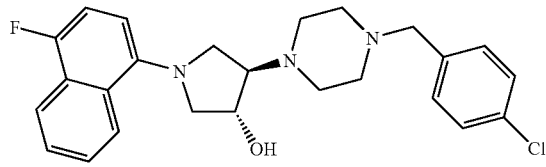

53
4-[4-(4-chlorobenzyl)piperazin-1-yl]-1-(4-fluoro-1-naphthyl)pyrrolidin-3-ol

TABLE 1-continued

Examples of Compounds of Formula I-A

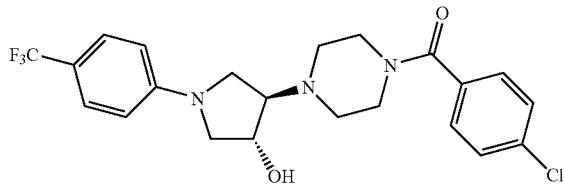

54
4-[4-(4-chlorobenzoyl)piperazin-1-yl]-1-[4-
(trifluoromethyl)phenyl]pyrrolidin-3-ol

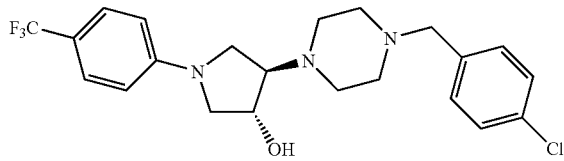

55
4-[4-(4-chlorobenzyl)piperazin-1-yl]-1-[4-
(trifluoromethyl)phenyl]pyrrolidin-3-ol

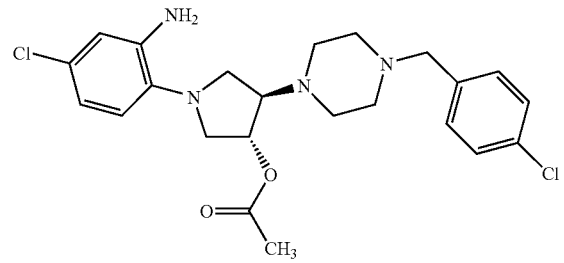

56
1-(2-amino-4-chlorophenyl)-4-[4-(4-
chlorobenzyl)piperazin-1-yl]pyrrolidin-3-yl
acetate

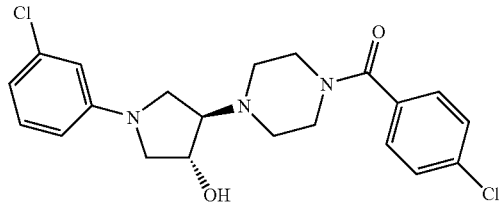

57
4-[4-(4-chlorobenzoyl)piperazin-1-yl]-1-(3-
chlorophenyl)pyrrolidin-3-ol

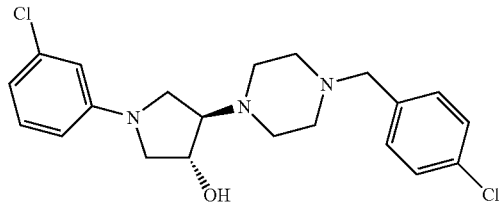

58
4-[4-(4-chlorobenzyl)piperazin-1-yl]-1-(3-
chlorophenyl)pyrrolidin-3-ol

TABLE 1-continued
Examples of Compounds of Formula I-A
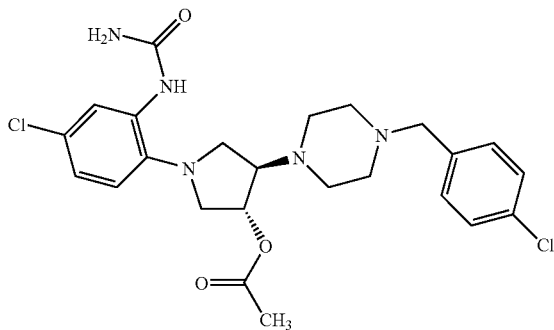
59
1-{2-[(aminocarbonyl)amino]-4-
chlorophenyl}-4-[4-(4-
chlorobenzyl)piperazin-1-yl]pyrrolidin-3-yl
acetate
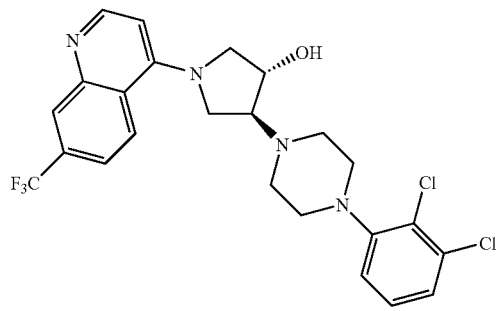
60
4-[4-(2,3-dichlorophenyl)piperazin-1-yl]-1-
[7-(trifluoromethyl)quinolin-4-yl]pyrrolidin-
3-ol
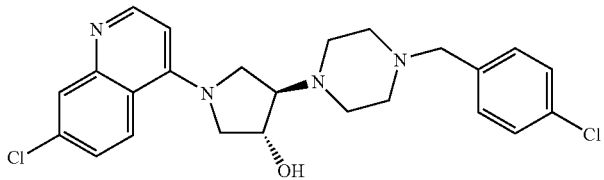
61
(3R,4R)-4-[4-(4-chlorobenzyl)piperazin-1-
yl]-1-(7-chloroquinolin-4-yl)pyrrolidin-3-ol
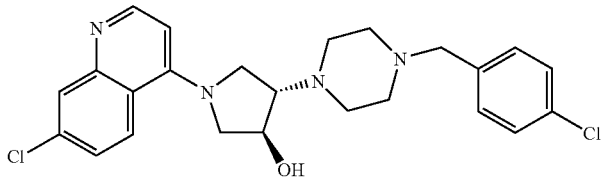
62
(3S,4S)-4-[4-(4-chlorobenzyl)piperazin-1-yl]
1-(7-chloroquinolin-4-yl)pyrrolidin-3-ol TABLE 1-continued
Examples of Compounds of Formula I-A
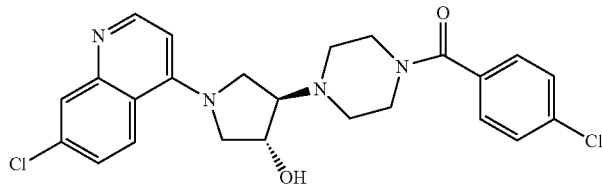
63
(3R,4R)-4-[4-(4-chlorobenzoyl)piperazin-1-
yl]-1-(7-chloroquinolin-4-yl)pyrrolidin-3-ol
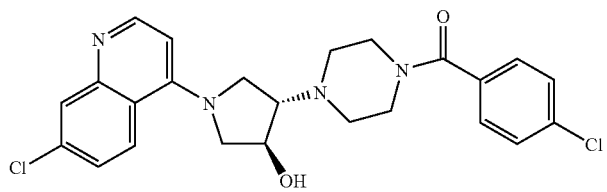
64
(3S,4S)-4-114-(4-chlorobenzoyl)piperazin-1-
yl]-1-(7-chloroquinolin-4-yl)pyrrolidin-3-ol
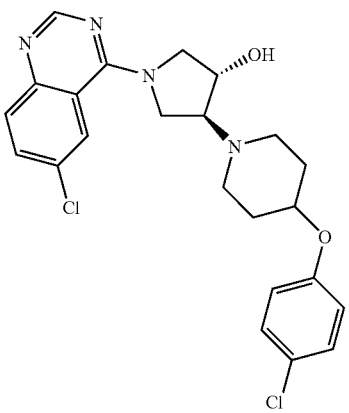
65
4-[4-(4-chlorophenoxy)piperidin-1-yl]-1-(6-
chloroquinazolin-4-yl)pyrrolidin-3-ol
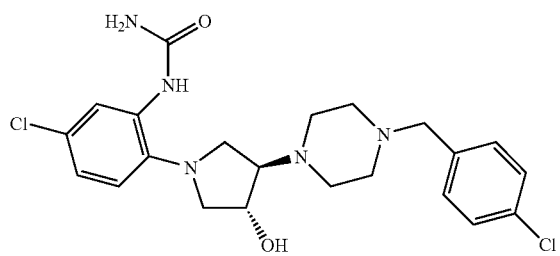
66
N-(5-chloro-2-{3-[4-(4-
chlorobenzyl)piperazin-1-yl]-4-
hydroxypyrrolidin-1-yl}phenyl)urea TABLE 1-continued Examples of Compounds of Formula I-A

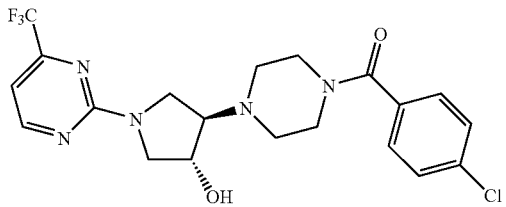

67
(3R,4R)-4-[4-(4-chlorobenzoyl)piperazin-1-
yl]-1-[4-(trifluoromethyl)pyrimidin-2-
yl]pyrrolidin-3-ol

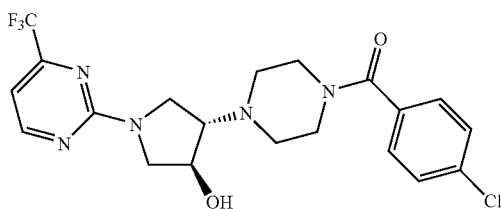

68
(3S,4S)-4-[4-(4-chlorobenzoyl)piperazin-1-
yl]-1-[4-(trifluoromethyl)pyrimidin-2-
yl]pyrrolidin-3-ol

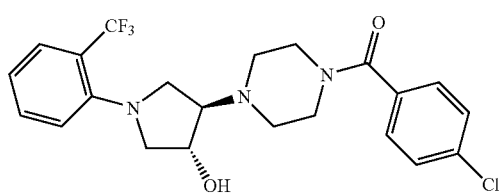

69
4-[4-(4-chlorobenzoyl)piperazin-1-yl]-1-[2-
(trifluoromethyl)phenyl]pyrrolidin-3-ol

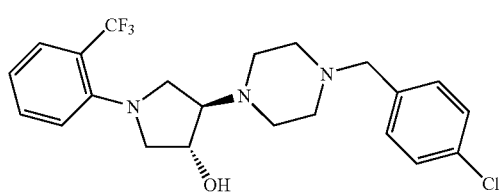

70
4-[4-(4-chlorobenzyl)piperazin-1-yl]-1-[2-
(trifluoromethyl)phenyl]pyrrolidin-3-ol

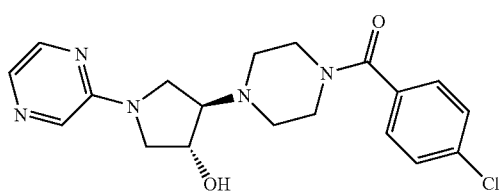

71
4-[4-(4-chlorobenzoyl)piperazin-1-yl]-1-
pyrazin-2-ylpyrrolidin-3-ol

TABLE 1-continued

Examples of Compounds of Formula I-A

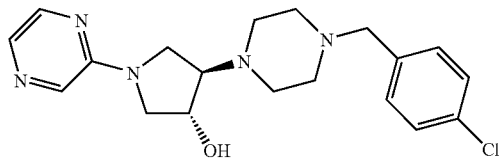

72
4-[4-(4-chlorobenzyl)piperazin-1-yl]-1-
pyrazin-2-ylpyrrolidin-3-ol

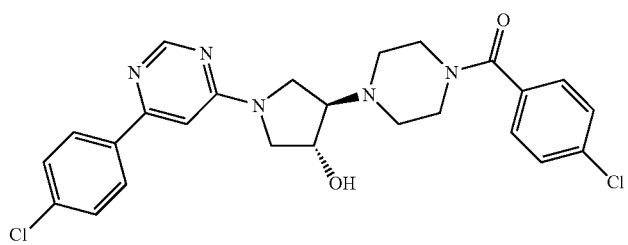

73
4-[4-(4-chlorobenzoyl)piperazin-1-yl]-1-[6-
(4-chlorophenyl)pyrimidin-4-yl]pyrrolidin-3-
ol

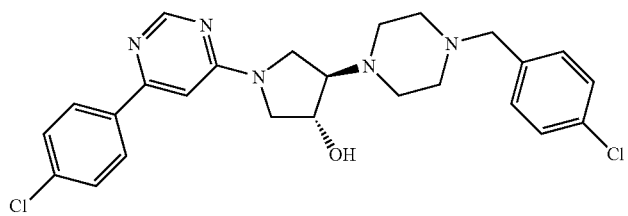

74
4-[4-(4-chlorobenzyl)piperazin-1-yl]-1-[6-(4-
chlorophenyl)pyrimidin-4-yl]pyrrolidin-3-ol

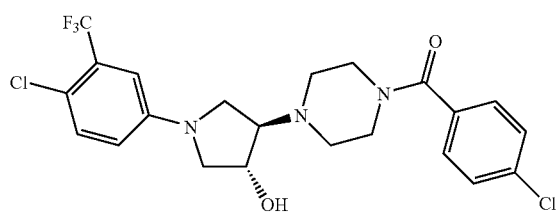

75
4-[4-(4-chlorobenzoyl)piperazin-1-yl]-1-[4-
chloro-3-(trifluoromethyl)phenyl]pyrrolidin-
3-ol

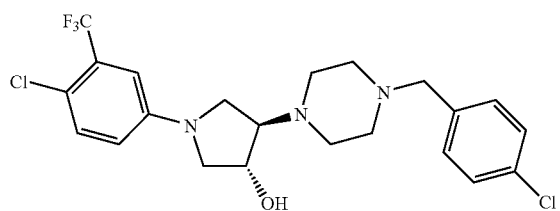

76
4-[4-(4-chlorobenzyl)piperazin-1-yl]-1-[4-
chloro-3-(trifluoromethyl)phenyl]pyrrolidin-
3-ol TABLE 1-continued
Examples of Compounds of Formula I-A
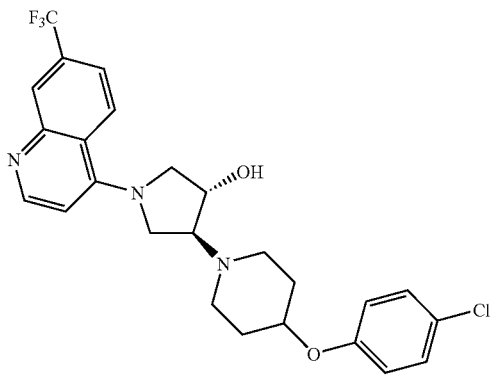
77
4-[4-(4-chlorophenoxy)piperidin-1-yl]-1-[7-
(trifluoromethyl)quinolin-4-yl]pyrrolidin-3-
ol
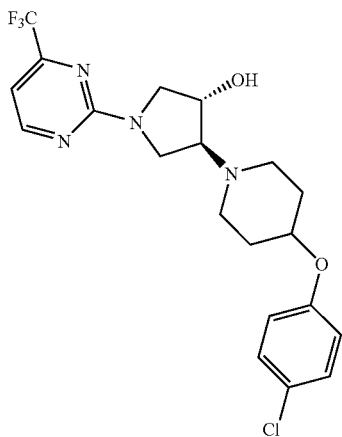
78
4-[4-(4-chlorophenoxy)piperidin-1-yl]-1-[4-
(trifluoromethyl)pyrimidin-2-yl]pyrrolidin-3-
ol
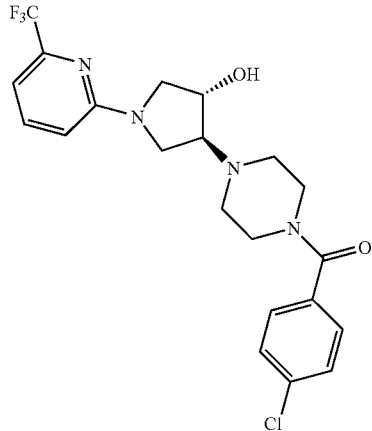
79
4-1 14-(4-chlorobenzoyl)piperazin-1-yl]-1-[6-
(trifluoromethyl)pyridin-2-yl]pyrrolidin-3-ol TABLE 1-continued
Examples of Compounds of Formula I-A
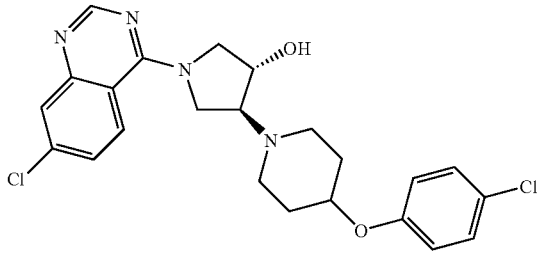
80
4-[4-(4-chlorophenoxy)piperidin-1-yl]-1-(7-chloroquinazolin-4-yl)pyrrolidin-3-ol
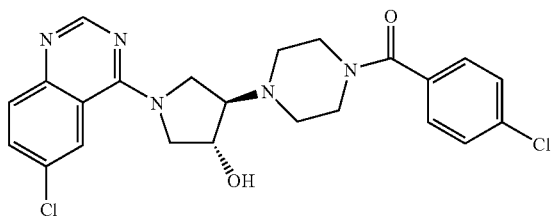
81
4-[4-(4-chlorobenzoyl)piperazin-1-yl]-1-(6-chloroquinazolin-4-yl)pyrrolidin-3-ol
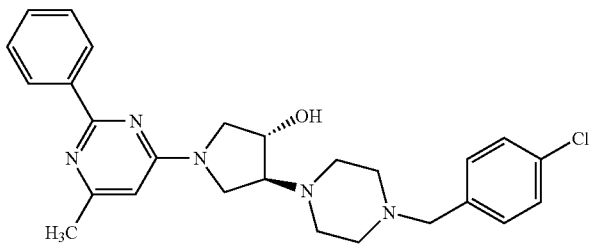
82
4-[4-(4-chlorobenzyl)piperazin-1-yl]-1-(6-methyl-2-phenylpyrimidin-4-yl)pyrrolidin-3-ol
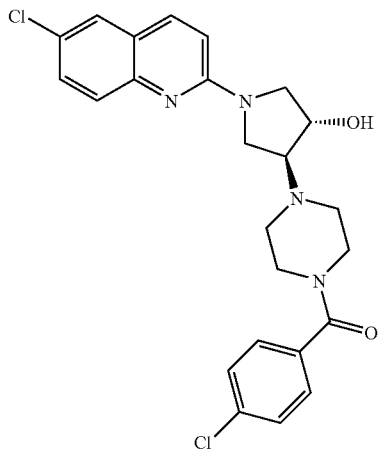
83
4-[4-(4-chlorobenzoyl)piperazin-1-yl]-1-(6-chloroquinolin-2-yl)pyrrolidin-3-ol TABLE 1-continued
Examples of Compounds of Formula I-A
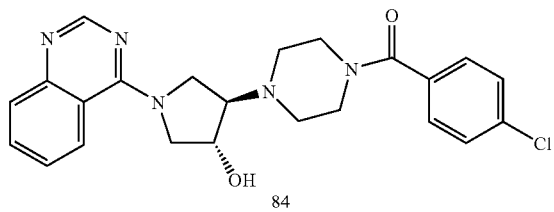
84
4-[4-(4-chlorobenzoyl)piperazin-1-yl]-1-
quinazolin-4-ylpyrrolidin-3-ol
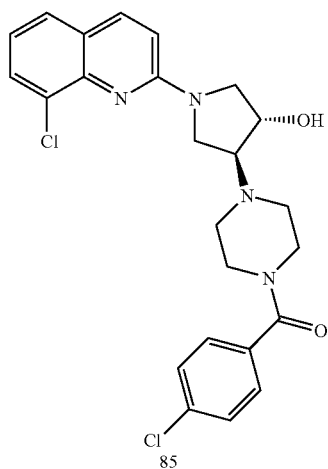
85
4-[4-(4-chlorobenzoyl)piperazin-1-yl]-1-(8-
chloroquinolin-2-yl)pyrrolidin-3-ol
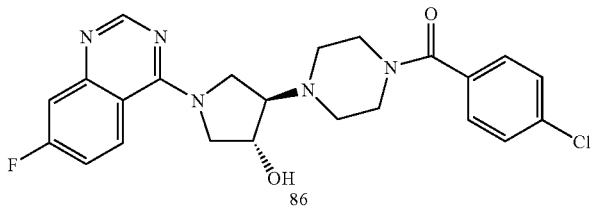
86
4-[4-(4-chlorobenzoyl)piperazin-1-yl]-1-(7-
fluoroquinazolin-4-yl)pyrrolidin-3-ol
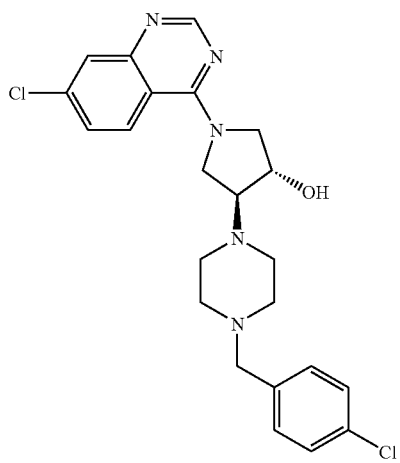
87
4-[4-(4-chlorobenzyl)piperazin-1-yl]-1-(7-
chloroquinazolin-4-yl)pyrrolidin-3-ol TABLE 1-continued Examples of Compounds of Formula I-A

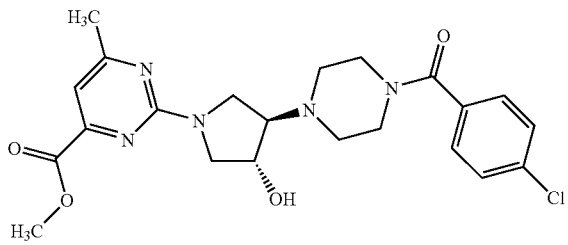

88
methyl 2-{3-[4-(4-chlorobenzoyl)piperazin-
1-yl]-4-hydroxypyrrolidin-1-yl}-6-
methylpyrimidine-4-carboxylate

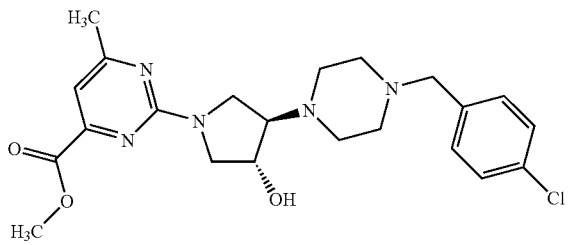

89
methyl 2-{3-[4-(4-chlorobenzyl)piperazin-1-
yl]-4-hydroxypyrrolidin-1-yl}-6-
methylpyrimidine-4-carboxylate

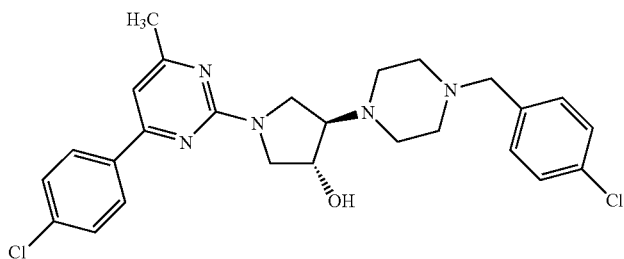

90
4-[4-(4-chlorobenzyl)piperazin-1-yl]-1-[4-(4-
chlorophenyl)-6-methylpyrimidin-2-
yl]pyrrolidin-3-ol

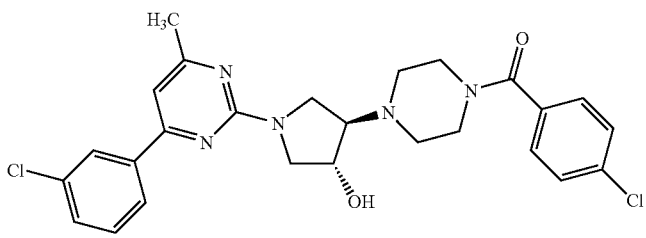

91
4-[4-(4-chlorobenzoyl)piperazin-1-yl]-1-[4-
(3-chlorophenyl)-6-methylpyrimidin-2-
yl]pyrrolidin-3-ol TABLE 1-continued
Examples of Compounds of Formula I-A
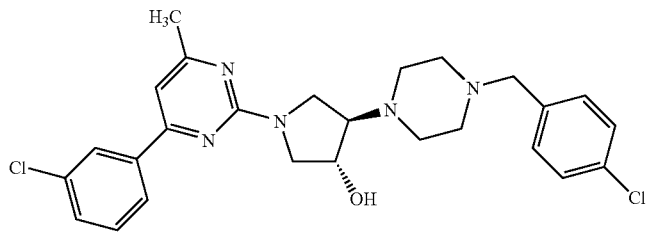
92
4-[4-(4-chlorobenzyl)piperazin-1-yl]-1-[4-(3-
chlorophenyl)-6-methylpyrimidin-2-
yl]pyrrolidin-3-ol
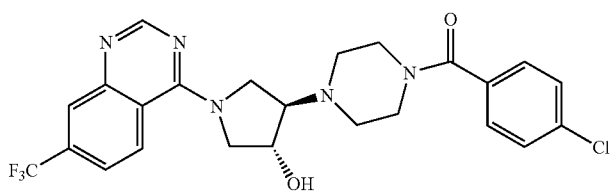
93
4-[4-(4-chlorobenzoyl)piperazin-1-yl]-1-[7-
(trifluoromethyl)quinazolin-4-yl]pyrrolidin-
3-ol
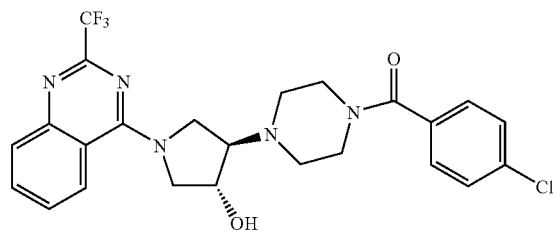
94
4-[4-(4-chlorobenzoyl)piperazin-1-yl]-1-[2-
(trifluoromethyl)quinazolin-4-yl]pyrrolidin-
3-ol
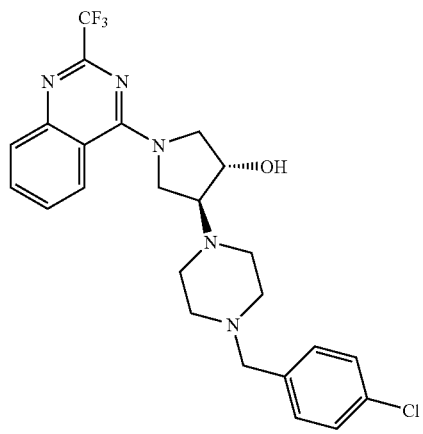
95
4-[4-(4-chlorobenzyl)piperazin-1-yl]-1-[2-
(trifluoromethyl)quinazolin-4-yl]pyrrolidin-
3-ol TABLE 1-continued
Examples of Compounds of Formula I-A
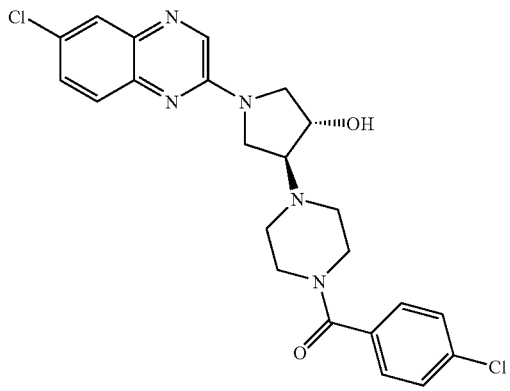
96
4-[4-(4-chlorobenzoyl)piperazin-1-yl]-1-(6-
chloroquinoxalin-2-yl)pyrrolidin-3-ol
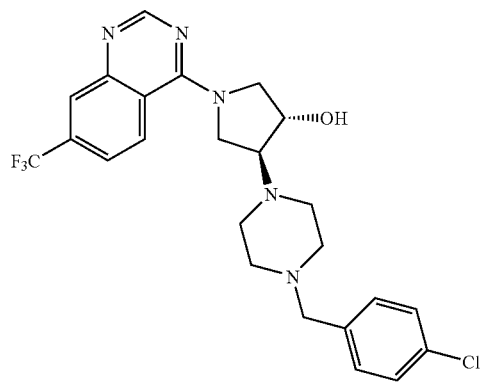
97
4-[4-(4-chlorobenzyl)piperazin-1-yl]-1-[7-
(trifluoromethyl)quinazolin-4-yl]pyrrolidin-
3-ol
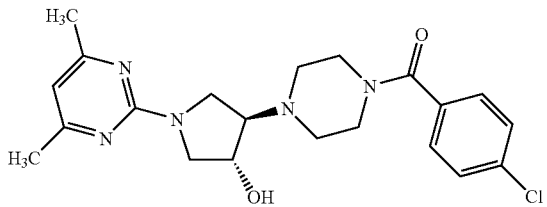
98
4-[4-(4-chlorobenzoyl)piperazin-1-yl]-1-(4,6-
dimethylpyrimidin-2-yl)pyrrolidin-3-ol
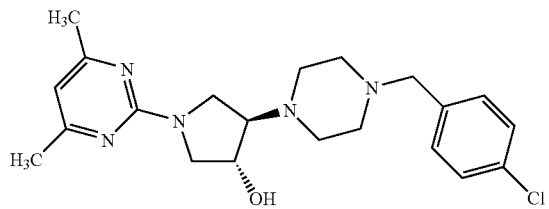
99
4-[4-(4-chlorobenzyl)piperazin-1-yl]-1-(4,6-
dimethylpyrimidin-2-yl)pyrrolidin-3-ol TABLE 1-continued Examples of Compounds of Formula I-A

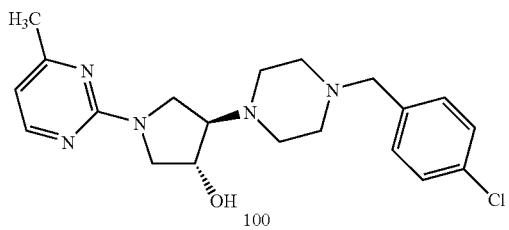

100
4-[4-(4-chlorobenzyl)piperazin-1-yl]-1-(4-
methylpyrimidin-2-yl)pyrrolidin-3-ol

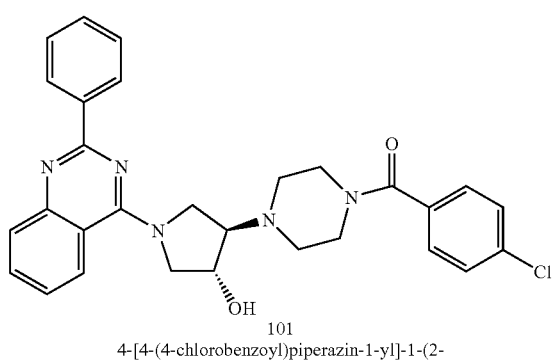

101
4-[4-(4-chlorobenzoyl)piperazin-1-yl]-1-(2-
phenylquinazolin-4-yl)pyrrolidin-3-ol

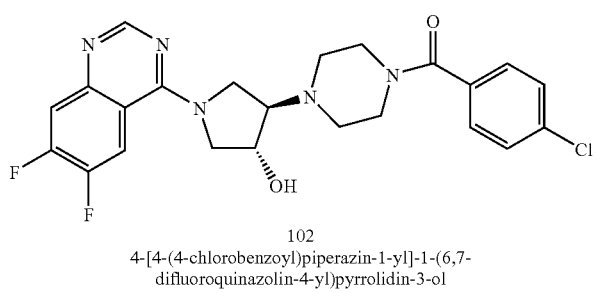

102
4-[4-(4-chlorobenzoyl)piperazin-1-yl]-1-(6,7-
difluoroquinazolin-4-yl)pyrrolidin-3-ol

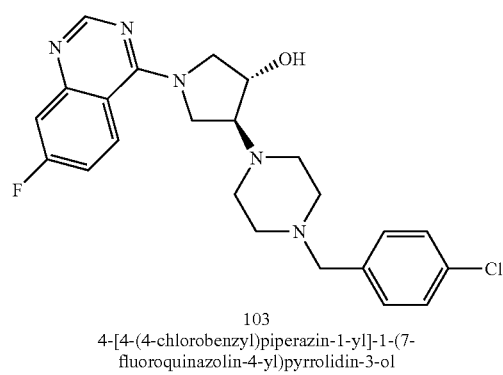

103
4-[4-(4-chlorobenzyl)piperazin-1-yl]-1-(7-
fluoroquinazolin-4-yl)pyrrolidin-3-ol

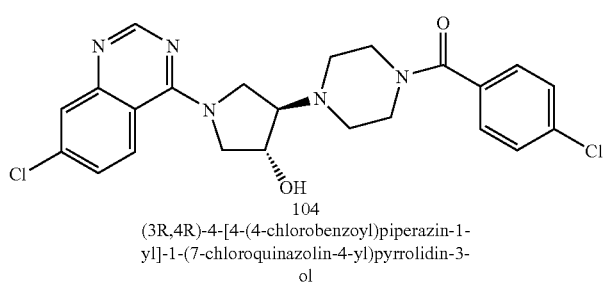

104
(3R,4R)-4-[4-(4-chlorobenzoyl)piperazin-1-
yl]-1-(7-chloroquinazolin-4-yl)pyrrolidin-3-
ol TABLE 1-continued Examples of Compounds of Formula I-A

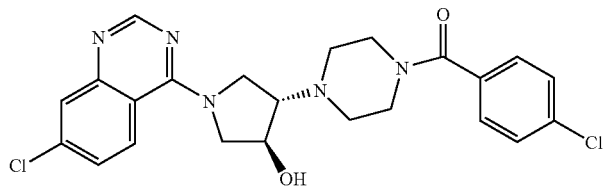

105
(3S,4S)-4-[4-(4-chlorobenzoyl)piperazin-1-
yl]-1-(7-chloroquinazolin-4-yl)pyrrolidin-3-
ol

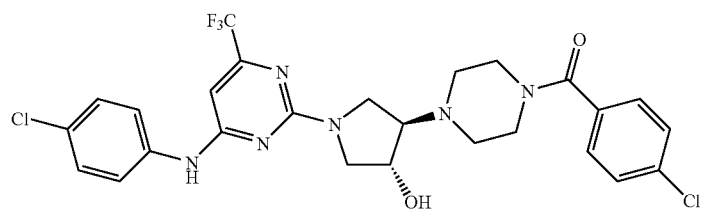

106
4-[4-(4-chlorobenzoyl)piperazin-1-yl]-1-[4-
[(4-chlorophenyl)amino]-6-
(trifluoromethyl)pyrimidin-2-yl]pyrrolidin-3-
ol

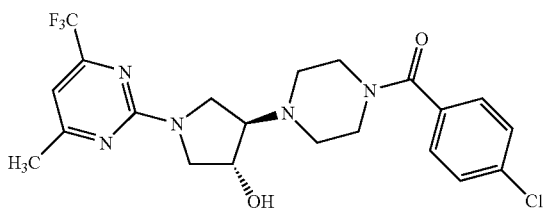

107
4-[4-(4-chlorobenzoyl)piperazin-1-yl]-1-[4-
methyl-6-(trifluoromethyl)pyrimidin-2-
yl]pyrrolidin-3-ol

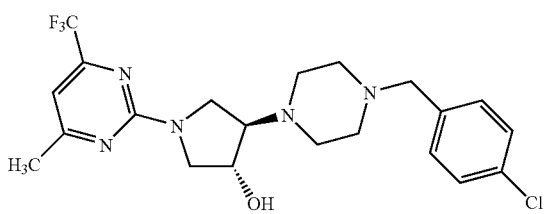

108
4-[4-(4-chlorobenzyl)piperazin-1-yl]-1-[4-
methyl-6-(trifluoromethyl)pyrimidin-2-
yl]pyrrolidin-3-ol

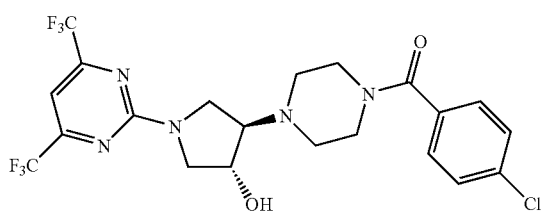

109
1-[4,6-bis(trifluoromethyl)pyrimidin-2-yl]-4-
[4-(4-chlorobenzoyl)piperazin-1-
yl]pyrrolidin-3-ol TABLE 1-continued Examples of Compounds of Formula I-A

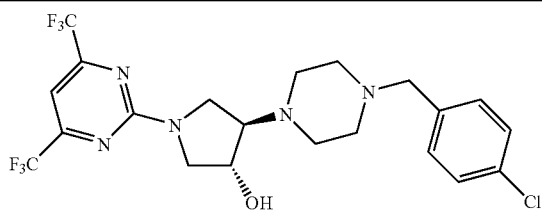

110
1-[4,6-bis(trifluoromethyl)pyrimidin-2-yl]-4-
[4-(4-chlorobenzyl)piperazin-1-yl]pyrrolidin
3-ol

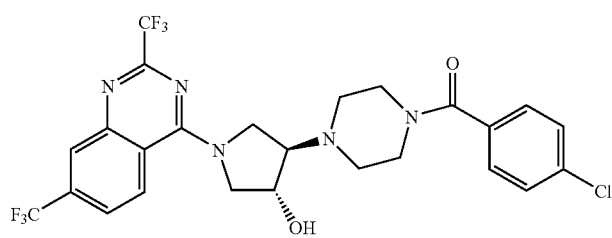

111
1-[2,7-bis(trifluoromethyl)quinazolin-4-yl]-
4-[4-(4-chlorobenzoyl)piperazin-1-
yl]pyrrolidin-3-ol

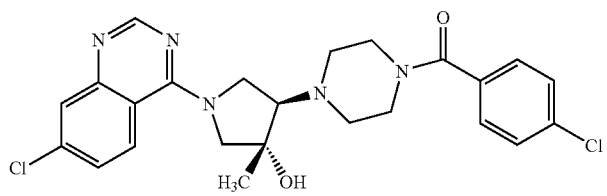

112
4-[4-(4-chlorobenzoyl)piperazin-1-yl]-1-(7-
chloroquinazolin-4-yl)-3-methylpyrrolidin-3-
ol

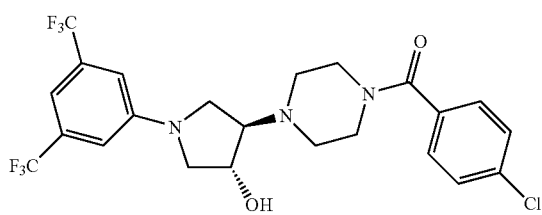

113
1-[3,5-bis(trifluoromethyl)phenyl]-4-[4-(4-
chlorobenzoyl)piperazin-1-yl]pyrrolidin-3-ol

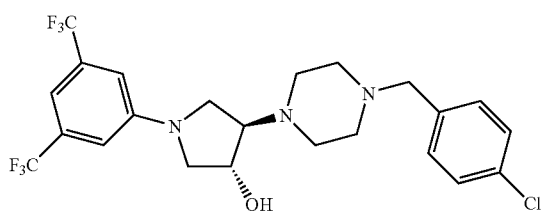

114
1-[3,5-bis(trifluoromethyl)phenyl]-4-[4-(4-
chlorobenzyl)piperazin-1-yl]pyrrolidin-3-ol TABLE 1-continued
Examples of Compounds of Formula I-A
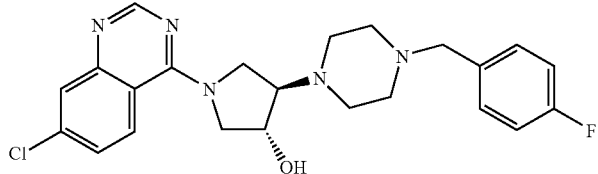
115
1-(7-chloroquinazolin-4-yl)-4-[4-(4-fluorobenzyl)piperazin-1-yl]pyrrolidin-3-ol
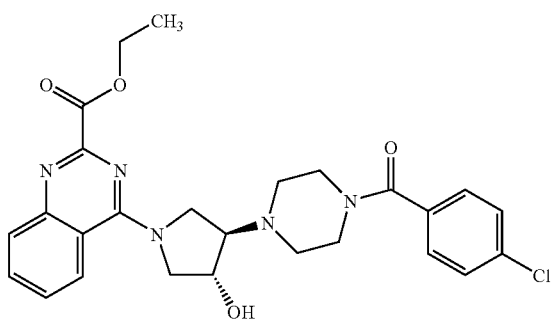
116
ethyl 4-{3-[4-(4-chlorobenzoyl)piperazin-1-yl]-4-hydroxypyrrolidin-1-yl}quinazoline-2-carboxylate
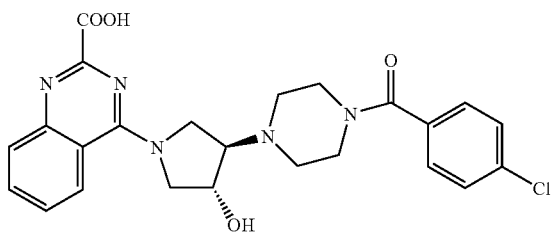
117
4-}3-[4-(4-chlorobenzoyl)piperazin-1-yl]-4-hydroxypyrrolidin-1-yl}quinazoline-2-carboxylic acid
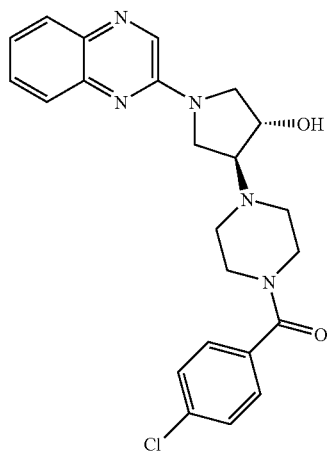
118
4-[4-(4-chlorobenzoyl)piperazin-1-yl]-1-quinoxalin-2-ylpyrrolidin-3-ol TABLE 1-continued Examples of Compounds of Formula I-A

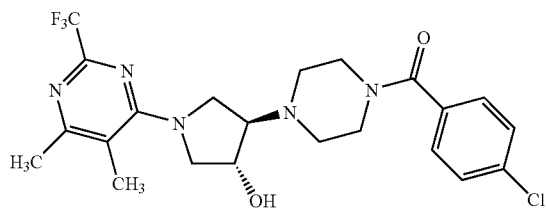

119
4-[4-(4-chlorobenzoyl)piperazin-1-yl]-1-[5,6-
dimethyl-2-(trifluoromethyl)pyrimidin-4-
yl]pyrrolidin-3-ol

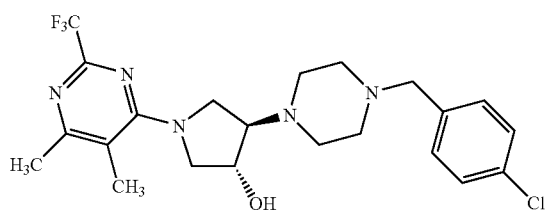

120
4-[4-(4-chlorobenzyl)piperazin-1-yl]-1-[5,6-
dimethyl-2-(trifluoromethyl)pyrimidin-4-
yl]pyrrolidin-3-ol

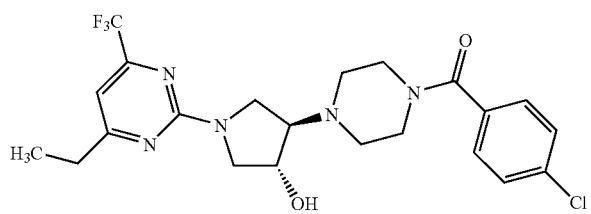

121
4-[4-(4-chlorobenzoyl)piperazin-1-yl]-1-[4-
ethyl-6-(trifluoromethyl)pyrimidin-2-
yl]pyrrolidin-3-ol

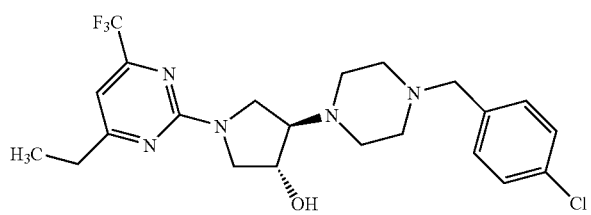

122
4-[4-(4-chlorobenzyl)piperazin-1-yl]-1-[4-
ethyl-6-(trifluoromethyl)pyrimidin-2-
yl]pyrrolidin-3-ol

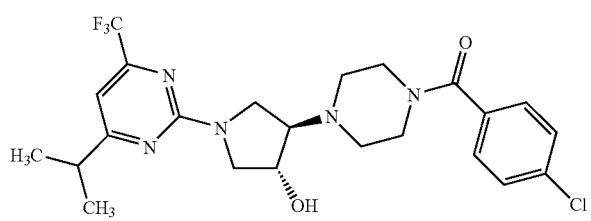

123
4-[4-(4-chlorobenzoyl)piperazin-1-yl]-1-[4-
isopropyl-6-(trifluoromethyl)pyrimidin-2-
yl]pyrrolidin-3-ol TABLE 1-continued
Examples of Compounds of Formula I-A
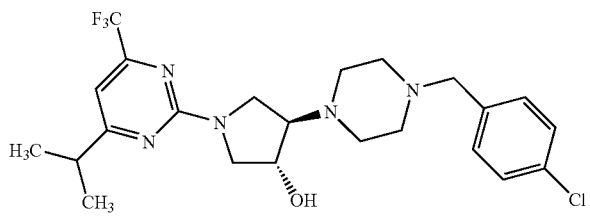
124
4-[4-(4-chlorobenzyl)piperazin-1-yl]-1-[4-
isopropyl-6-(trifluoromethyl)pyrimidin-2-
yl]pyrrolidin-3-ol
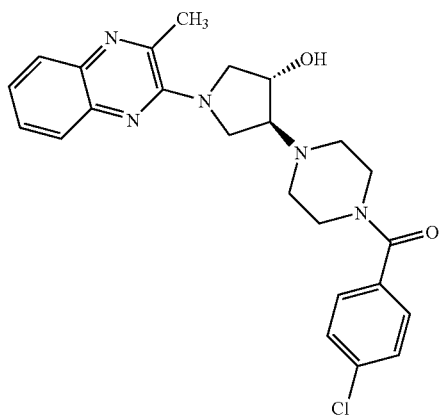
125
4-[4-(4-chlorobenzoyl)piperazin-1-yl]-1-(3-
methylquinoxalin-2-yl)pyrrolidin-3-ol
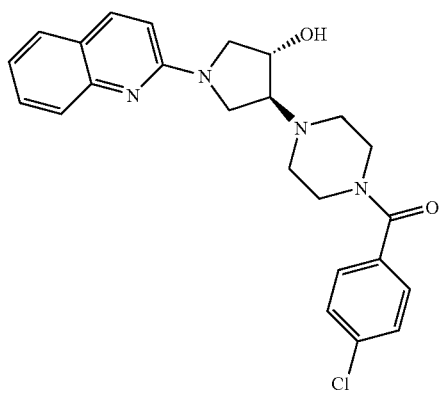
126
4-[4-(4-chlorobenzoyl)piperazin-1-yl]-1-
quinolin-2-ylpyrrolidin-3-ol TABLE 1-continued
Examples of Compounds of Formula I-A
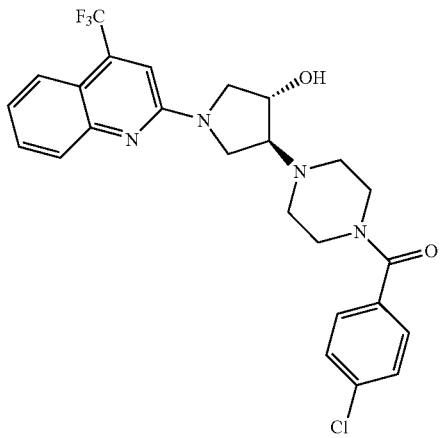
127
4-[4-(4-chlorobenzoyl)piperazin-1-yl]-1-[4-
(trifluoromethyl)quinolin-2-yl]pyrrolidin-3-
ol
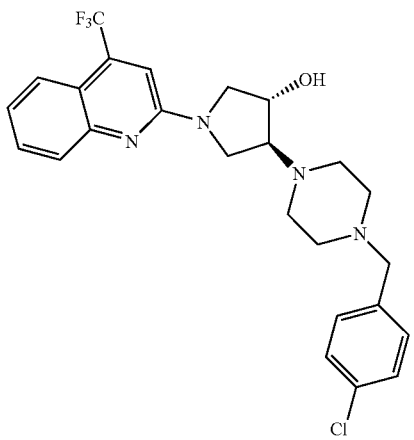
128
4-[4-(4-chlorobenzyl)piperazin-1-yl]-1-[4-
(trifluoromethyl)quinolin-2-yl]pyrrolidin-3-
ol
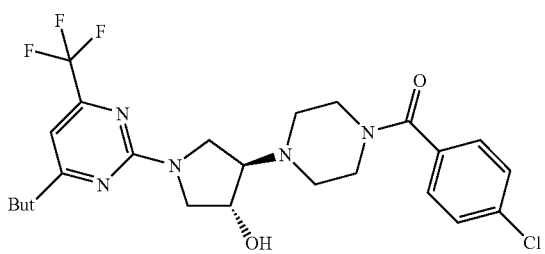
129
1-[4-tert-butyl-6-(trifluoromethyl)pyrimidin-
2-yl]-4-[4-(4-chlorobenzoyl)piperazin-1-
yl]pyrrolidin-3-ol TABLE 1-continued
Examples of Compounds of Formula I-A
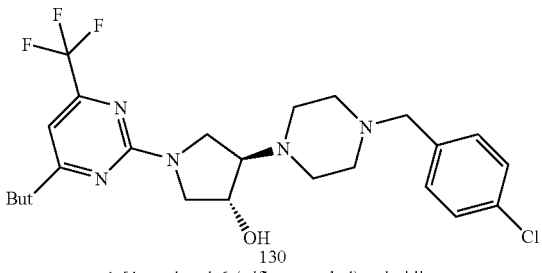
130
1-[4-tert-butyl-6-(trifluoromethyl)pyrimidin-
2-yl]-4-[4-(4-chlorobenzyl)piperazin-1-
yl]pyrrolidin-3-ol
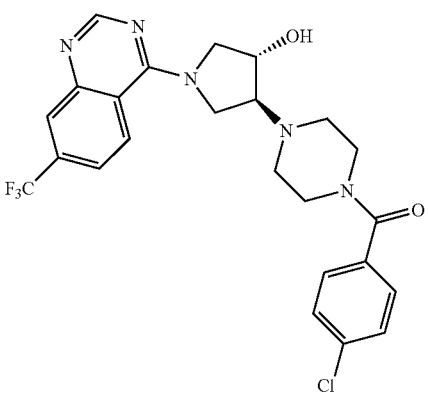
131
4-[4-(4-chlorobenzoyl)piperazil-1-yl]-1-[7-
(trifluoromethyl)quinazolin-4-yl]pyrrolidin-
3-ol
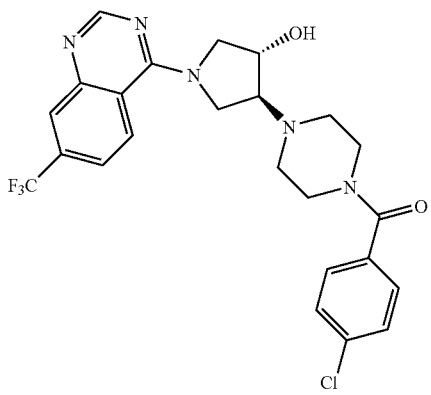
132
4-[4-(4-chlorobenzoyl)piperazin-1-yl]-1-[7-
(trifluoromethyl)quinazolin-4-yl]pyrrolidin-
3-ol
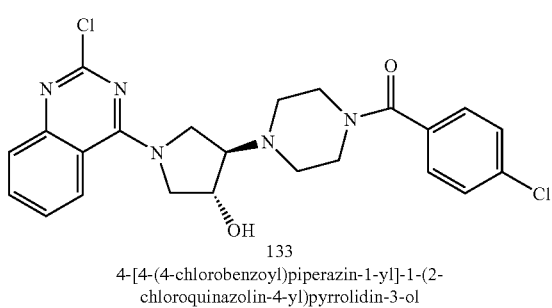
133
4-[4-(4-chlorobenzoyl)piperazin-1-yl]-1-(2-
chloroquinazolin-4-yl)pyrrolidin-3-ol TABLE 1-continued Examples of Compounds of Formula I-A

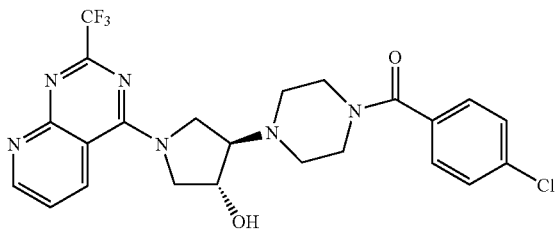

134
4-[4-(4-chlorobenzoyl)piperazin-1-yl]-1-[2-
(trifluoromethyl)pyrido[2,3-d]pyrimidin-4-
yl]pyrrolidin-3-ol

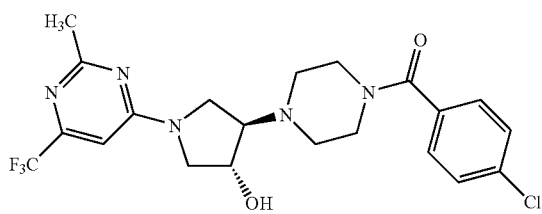

135
4-[4-(4-chlorobenzoyl)piperazin-1-yl]-1-[2-
methyl-6-(trifluoromethyl)pyrimidin-4-
yl]pyrrolidin-3-ol

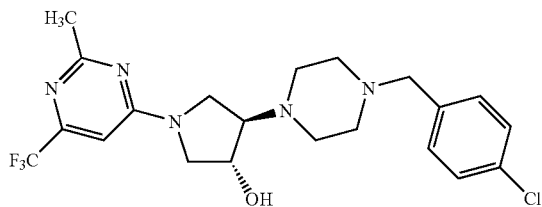

136
4-[4-(4-chlorobenzyl)piperazin-1-yl]-1-[2-
methyl-6-(trifluoromethyl)pyrimidin-4-
yl]pyrrolidin-3-ol

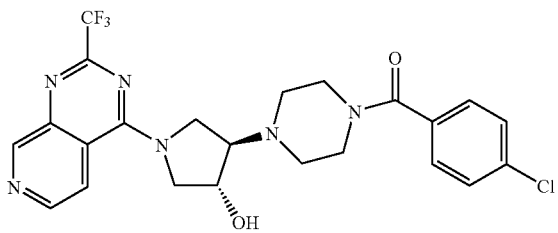

137
4-[4-(4-chlorobenzoyl)piperazin-1-yl]-1-[2-
(trifluoromethyl)pyrido[3,4-d]pyrimidin-4-
yl]pyrrolidin-3-ol TABLE 1-continued
Examples of Compounds of Formula I-A
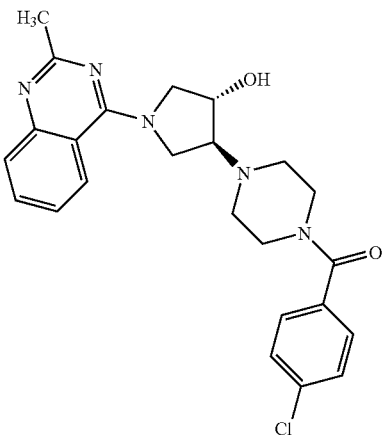
138
4-[4-(4-chlorobenzoyl)piperazin-1-yl]-1-(2-
methylquinazolin-4-yl)pyrrolidin-3-ol
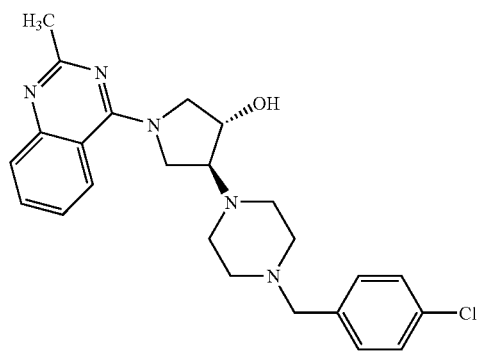
139
4-[4-(4-chlorobenzyl)piperazin-1-yl]-1-(2-
methylquinazolin-4-yl)pyrrolidin-3-ol
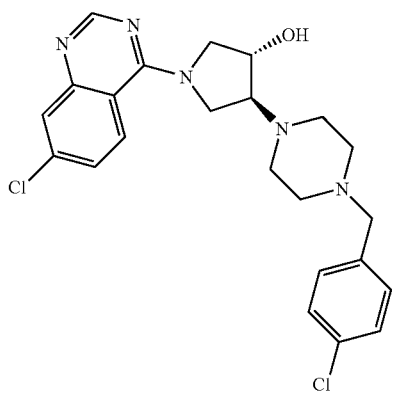
140
(3S,4S)-4-[4-(4-chlorobenzyl)piperazin-1-yl]-
1-(7-chloroquinazolin-4-yl)pyrrolidin-3-ol TABLE 1-continued Examples of Compounds of Formula I-A

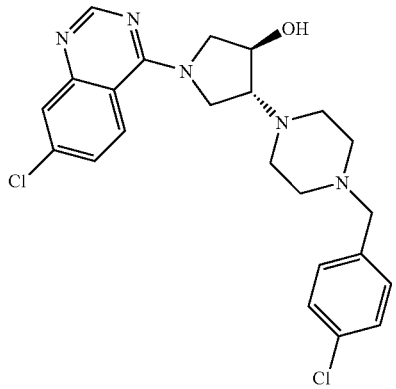

141
(3R,4R)-4-[4-(4-chlorobenzyl)piperazin-1-
yl]-1-(7-chloroquinazolin-4-yl)pyrrolidin-3-
ol

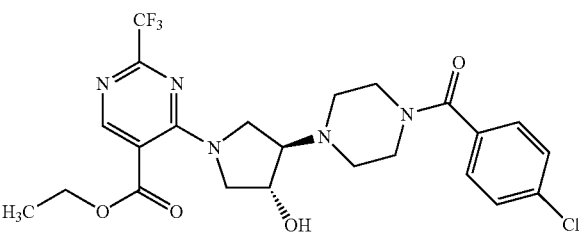

142
ethyl 4-{3-[4-(4-chlorobenzoyl)piperazin-1-
yl]4-hydroxypyrrolidin-1-yl}-2-
(trifluoromethyl)pyrimidine-5-carboxylate

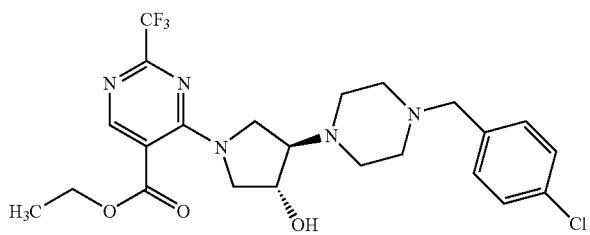

143
ethyl 4-{3-[4-(4-chlorobenzyl)piperazin-1-
yl]-4-hydroxypyrrolidin-1-yl}-2-
(trifluoromethyl)pyrimidine-5-carboxylate

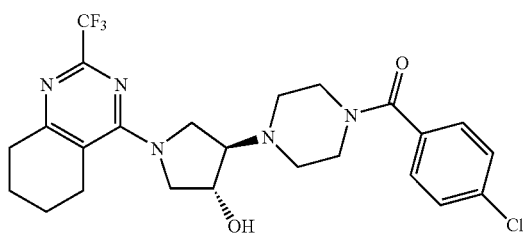

144
4-[4-(4-chlorobenzoyl)piperazin-1-yl]-1-[2-
(trifluoromethyl)-5,6,7,8-
tetrahydroquinazolin-4-yl]pyrrolidin-3-ol TABLE 1-continued
Examples of Compounds of Formula I-A
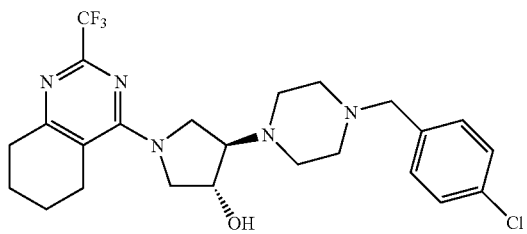
145
4-[4-(4-chlorobenzyl)piperazin-1-yl]-1-[2-
(trifluoromethyl)-5,6,7,8-
tetrahydroquinazolin-4-yl]pyrrolidin-3-ol
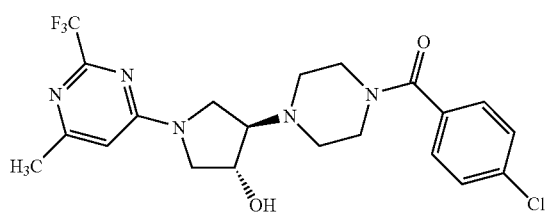
146
4-[4-(4-chlorobenzoyl)piperazin-1-yl]-1-[6-
methyl-2-(trifluoromethyl)pyrimidin-4-
yl]pyrrolidin-3-ol
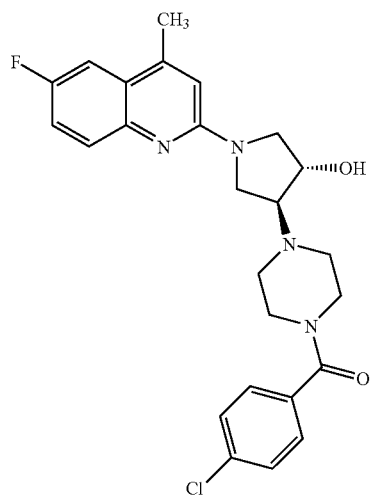
147
4-[4-(4-chlorobenzoyl)piperazin-1-yl]-1-(6-
fluoro-4-methylquinolin-2-yl)pyrrolidin-3-ol TABLE 1-continued
Examples of Compounds of Formula I-A
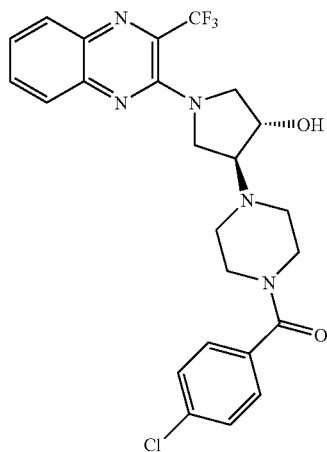
148
4-[4-(4-chlorobenzoyl)piperazin-1-yl]-1-[3-
(trifluoromethyl)quinoxalin-2-yl]pyrrolidin-
3-ol
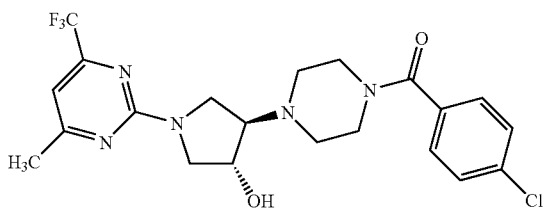
149
(3R,4R)-4-[4-(4-chlorobenzoyl)piperazin-1-
yl]-1-[4-methyl-6-
(trifluoromethyl)pyrimidin-2-yl]pyrrolidin-3-
ol
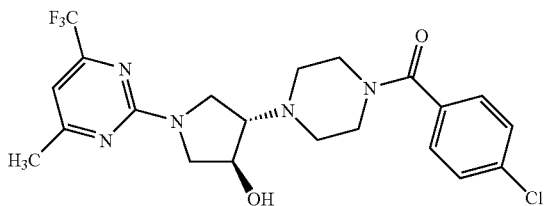
150
(3S,4S)-4-[4-(4-chlorobenzoyl)piperazin-1-
yl]-1-[4-methyl-6-
(trifluoromethyl)pyrimidin-2-yl]pyrrolidin-3-
ol TABLE 1-continued
Examples of Compounds of Formula I-A
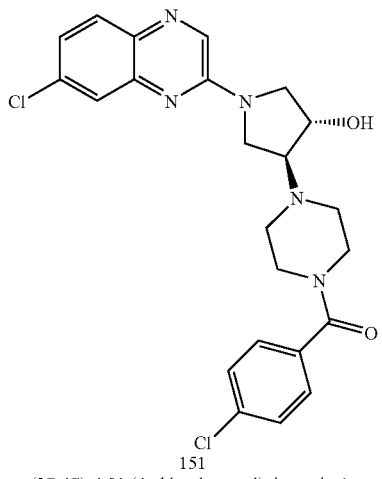
151
(3S,4S)-4-[4-(4-chlorobenzoyl)piperazin-1-
yl]-1-(7-chloroquinoxalin-2-yl)pyrrolidin-3-
ol
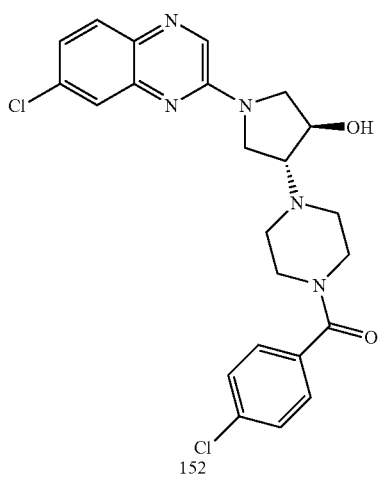
152
(3R,4R)-4-[4-(4-chlorobenzoyl)piperazin-1-
yl]-1-(7-chloroquinoxalin-2-yl)pyrrolidin-3-
ol
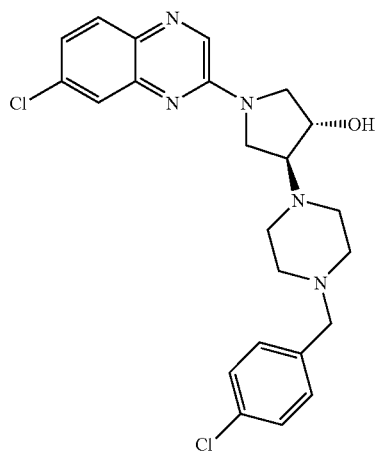
153
4-[4-(4-chlorobenzyl)piperazin-1-yl]-1-(7-
chloroquinoxalin-2-yl)pyrrolidin-3-ol TABLE 1-continued
Examples of Compounds of Formula I-A
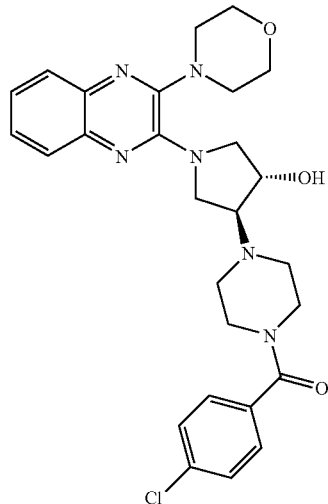
154
4-[4-(4-chlorobenzoyl)piperazin-1-yl]-1-(3-
morpholin-4-ylquinoxalin-2-yl)pyrrolidin-3-
ol
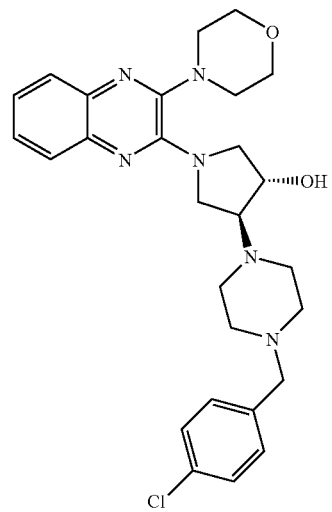
155
4-[4-(4-chlorobenzyl)piperazin-1-yl]-1-(3-
morpholin-4-ylquinoxalin-2-yl)pyrrolidin-3-
ol
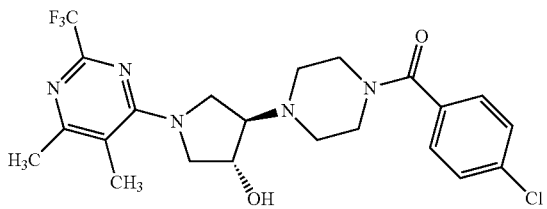
156
(3R,4R)4-[4-(4-chlorobenzoyl)piperazin-1-
yl]-1-[5,6-dimethyl-2-
(trifluoromethyl)pyrimidin-4-yl]pyrrolidin-3-
ol TABLE 1-continued
Examples of Compounds of Formula I-A
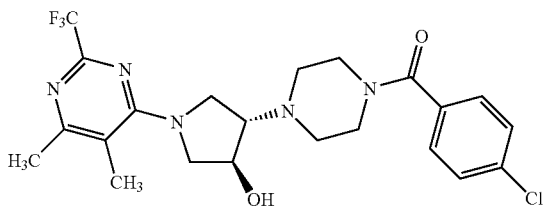
157
(3S,4S)-4-[4-(4-chlorobenzoyl)piperazin-1-
yl]-1-[5,6-dimethyl-2-
(trifluoromethyl)pyrimidin-4-yl]pyrrolidin-3-
ol
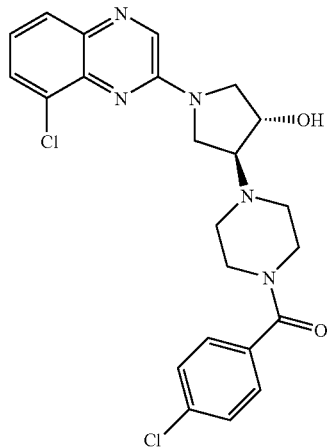
158
4-[4-(4-chlorobenzoyl)piperazin-1-yl]-1-(8-
chloroquinoxalin-2-yl)pyrrolidin-3-ol
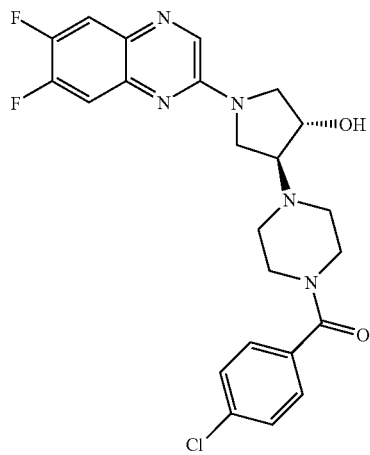
159
4-[4-(4-chlorobenzoyl)piperazin-1-yl]-1-(6,7-
difluoroquinoxalin-2-yl)pyrrolidin-3-ol TABLE 1-continued Examples of Compounds of Formula I-A

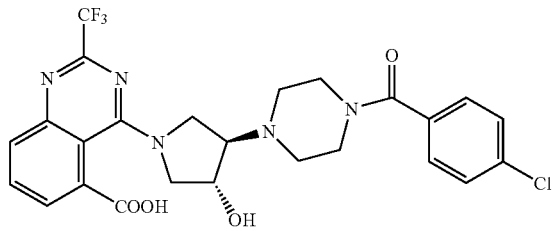

160
4-{3-[4-(4-chlorobenzoyl)piperazin-1-yl]-4-
hydroxypyrrolidin-1-yl}-2-
(trifluoromethyl)quinazoline-5-carboxylic
acid

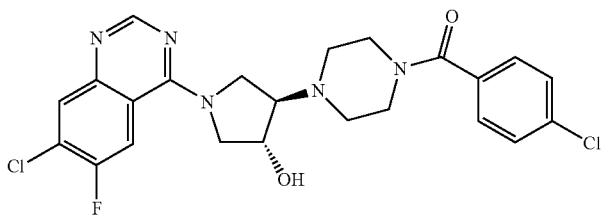

161
4-[4-(4-chlorobenzoyl)piperazin-1-yl]-1-(7-
chloro-6-fluoroquinazolin-4-yl)pyrrolidin-3-
ol

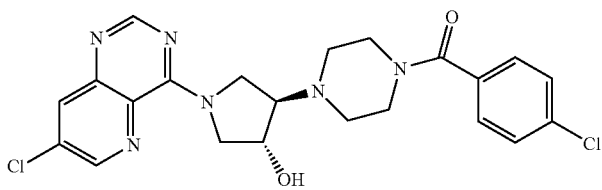

162
4-[4-(4-chlorobenzoyl)piperazin-1-yl]-1-(7-
chloropyrido[3,2-d]pyrimidin-4-
yl)pyrrolidin-3-ol

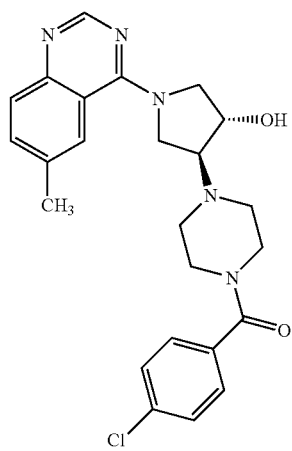

163
4-[4-(4-chlorobenzoyl)piperazin-1-yl]-1-(6-
methylquinazolin-4-yl)pyrrolidin-3-ol TABLE 1-continued
Examples of Compounds of Formula I-A
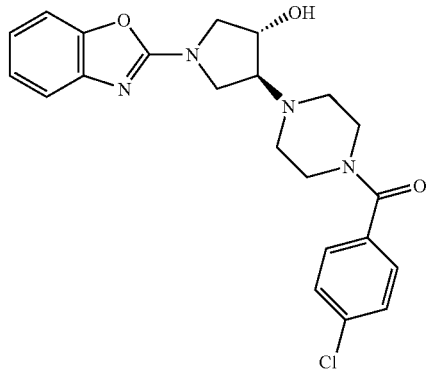
164
1-(1,3-benzoxazol-2-yl)-4-[4-(4-chlorobenzoyl)piperazin-1-yl]pyrrolidin-3-ol
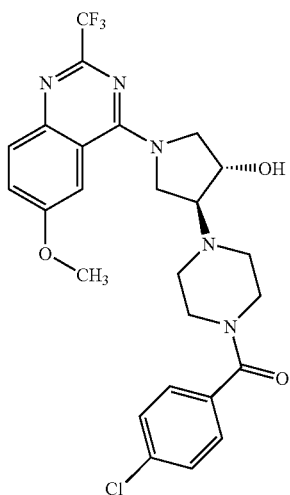
165
4-[4-(4-chlorobenzoyl)piperazin-1-yl]-1-[6-methoxy-2-(trifluoromethyl)quinazolin-4-yl]pyrrolidin-3-ol
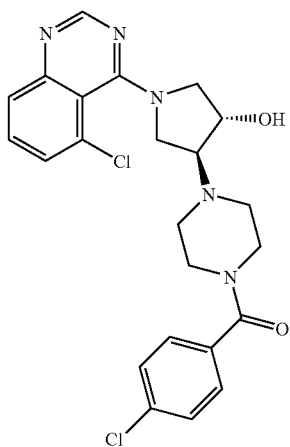
166
4-[4-(4-chlorobenzoyl)piperazin-1-yl]-1-(5-chloroquinazolin-4-yl)pyrrolidin-3-ol TABLE 1-continued
Examples of Compounds of Formula I-A
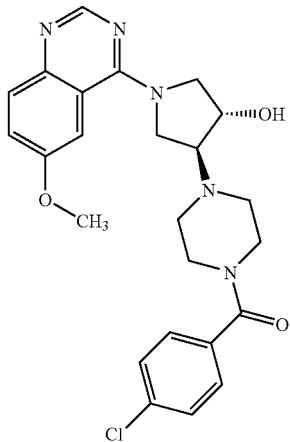
167
4-[4-(4-chlorobenzoyl)piperazin-1-yl]-1-(6-
methoxyquinazolin-4-yl)pyrrolidin-3-ol
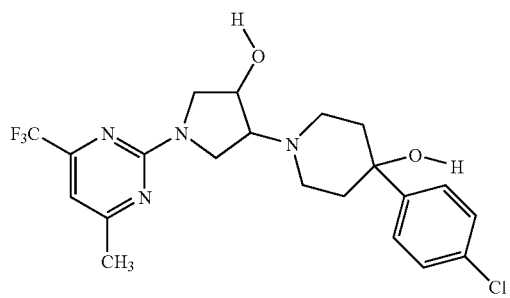
168
4-(4-chlorophenyl)-1-{4-hydroxy-1-[4-
methyl-6-(trifluoromethyl)pyrimidin-2-
yl]pyrrolidin-3-yl}piperidin-4-ol
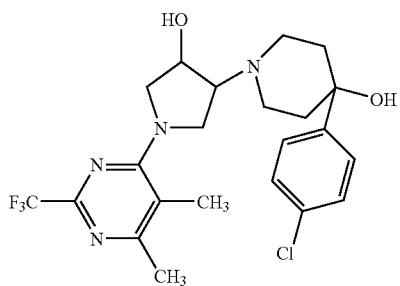
169
4-(4-chlorophenyl)-1-{1-[5,6-dimethyl-2-
(trifluoromethyl)pyrimidin-4-yl]-4-
hydroxypyrrolidin-3-yl}piperidin-4-ol TABLE 1-continued
Examples of Compounds of Formula I-A
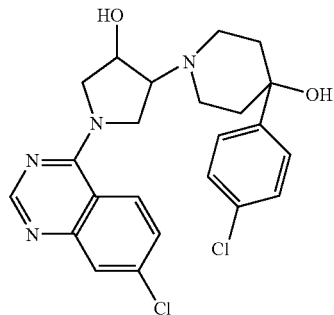
170
4-(4-chlorophenyl)-1-[1-(7-chloroquinazolin-
4-yl)-4-hydroxypyrrolidin-3-yl]piperidin-4-ol
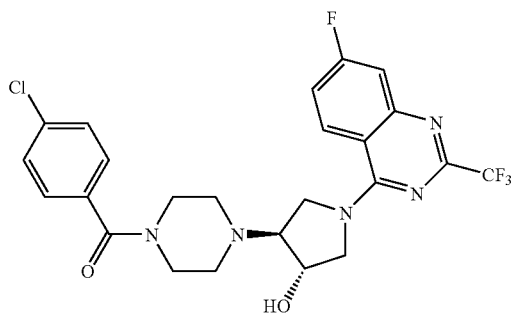
171
4-[4-(4-chlorobenzoyl)piperazin-1-yl]-1-[7-
fluoro-2-(trifluoromethyl)quinazolin-4-
yl]pyrrolidin-3-ol
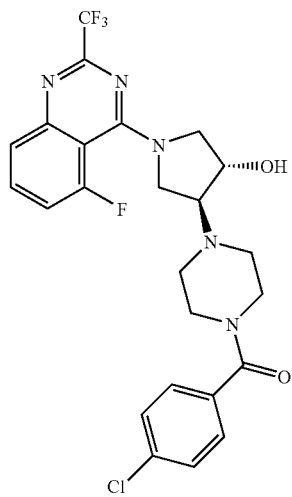
172
4-[4-(4-chlorobenzoyl)piperazin-1-yl]-1-[5-
fluoro-2-(trifluoromethyl)quinazolin-4-
yl]pyrrolidin-3-ol TABLE 1-continued
Examples of Compounds of Formula I-A
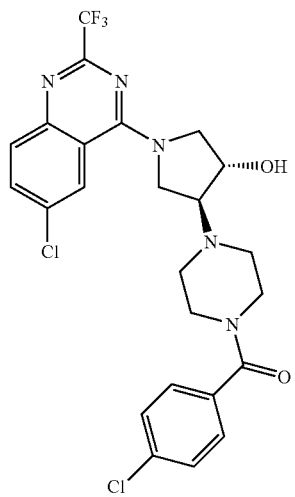
173
4-[4-(4-chlorobenzoyl)piperazin-1-yl]-1-[6-chloro-2-(trifluoromethyl)quinazolin-4-yl]pyrrolidin-3-ol
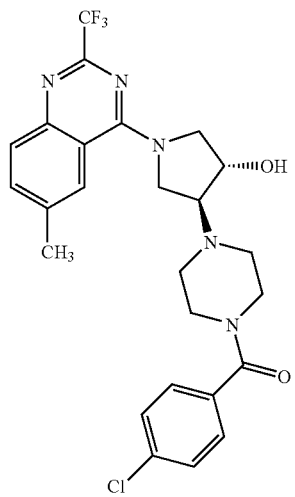
174
4-[4-(4-chlorobenzoyl)piperazin-1-yl]-1-[6-methyl-2-(trifluoromethyl)quinazolin-4-yl]pyrrolidin-3-ol TABLE 1-continued
Examples of Compounds of Formula I-A
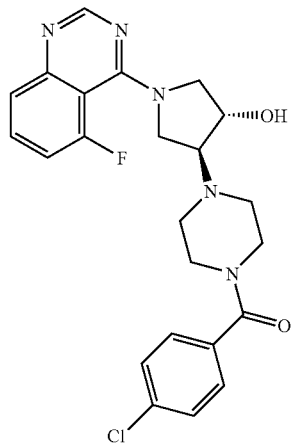
175
4-[4-(4-chlorobenzoyl)piperazin-1-yl]-1-(5-
fluoroquinazolin-4-yl)pyrrolidin-3-ol
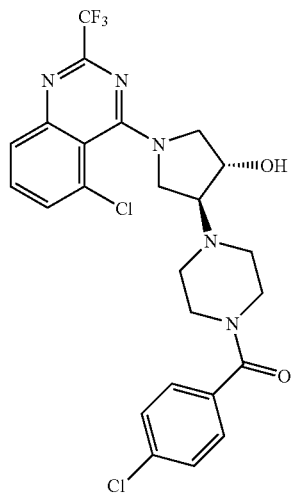
176
4-[4-(4-chlorobenzoyl)piperazin-1-yl]-1-[5-
chloro-2-(trifluoromethyl)quinazolin-4-
yl]pyrrolidin-3-ol TABLE 1-continued
Examples of Compounds of Formula I-A
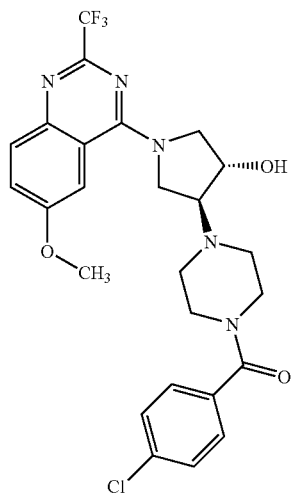
177
4-[4-(3S,4S)-(4-chlorobenzoyl)piperazin-1-
yl]-1-[6-methoxy-2-
(trifluoromethyl)quinazolin-4-yl]pyrrolidin-
3-ol
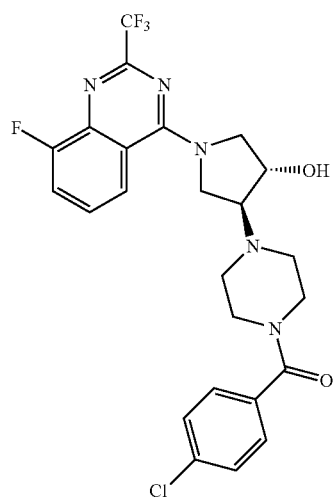
178
4-[4-(4-chlorobenzoyl)piperazin-1-yl]-1-[8-
fluoro-2-(trifluoromethyl)quinazolin-4-
yl]pyrrolidin-3-ol TABLE 1-continued
Examples of Compounds of Formula I-A
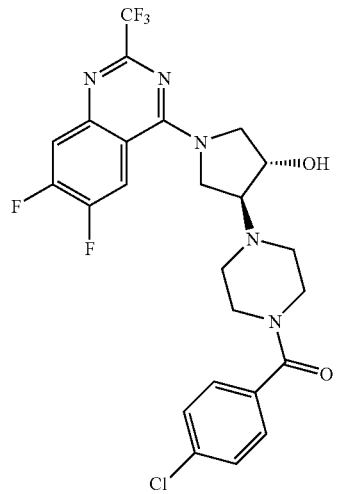
179
4-[4-(4-chlorobenzoyl)piperazin-1-yl]-1-[6,7-
difluoro-2-(trifluoromethyl)quinazolin-4-
yl]pyrrolidin-3-ol
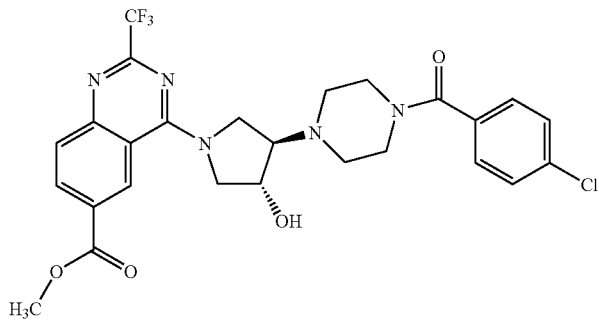
180
methyl 4-{3-[4-(4-chlorobenzoyl)piperazin-
1-yl]-4-hydroxypyrrolidin-1-yl}-2-
(trifluoromethyl)quinazoline-6-carboxylate
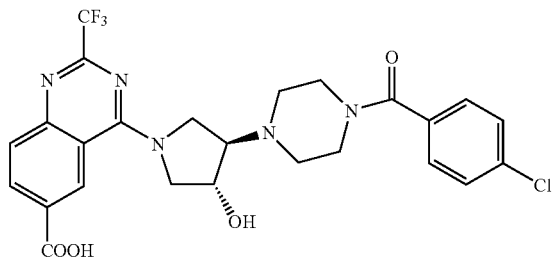
181
4-{3-[4-(4-chlorobenzoyl)piperazin-1-yl]-4-
hydroxypyrrolidin-1-yl}-2-
(trifluoromethyl)quinazoline-6-carboxylic
acid TABLE 1-continued
Examples of Compounds of Formula I-A
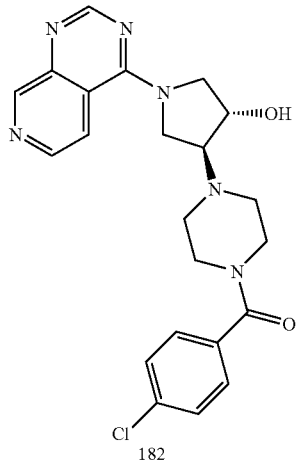
182
4-[4-(4-chlorobenzoyl)piperazin-1-yl]-1-
pyrido[3,4-d]pyrimidin-4-ylpyrrolidin-3-ol
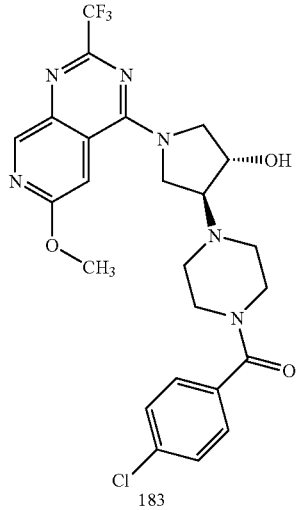
183
4-[4-(4-chlorobenzoyl)piperazin-1-yl]-1-[6-
methoxy-2-(trifluoromethyl)pyrido[3,4-
d]pyrimidin-4-yl]pyrrolidin-3-ol
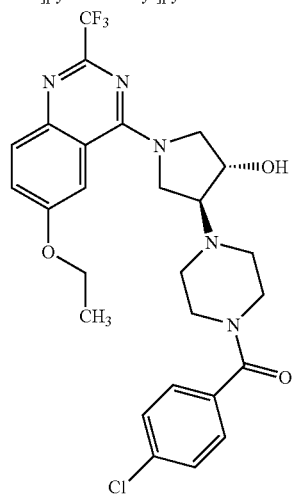
184
4-[4-(4-chlorobenzoyl)piperazin-1-yl]-1-[6-
ethoxy-2-(trifluoromethyl)quinazolin-4-
yl]pyrrolidin-3-ol TABLE 1-continued
Examples of Compounds of Formula I-A
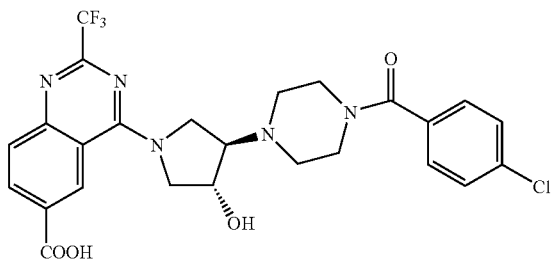
185
4-{(3R,4R)-3-[4-(4-chlorobenzoyl)piperazin-
1-yl]-4-hydroxypyrrolidin-1-yl}-2-
(trifluoromethyl)quinazoline-6-carboxylic
acid
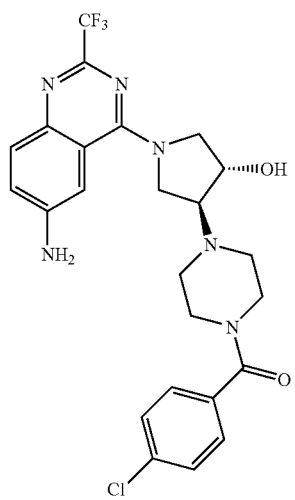
186
1-[6-amino-2-(trifluoromethyl)quinazolin-4-
yl]-4-[4-(4-chlorobenzoyl)piperazin-1-
yl]pyrrolidin-3-ol
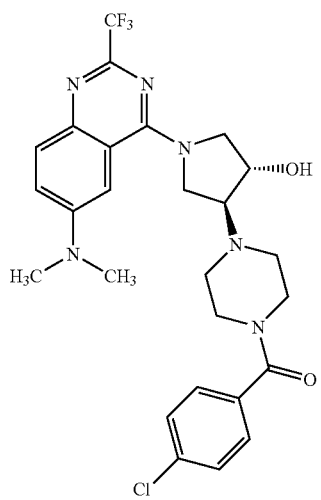
187
4-[4-(4-chlorobenzoyl)piperazin-1-yl]-1-[6-
(dimethylamino)-2-
(trifluoromethyl)quinazolin-4-yl]pyrrolidin-
3-ol TABLE 1-continued
Examples of Compounds of Formula I-A
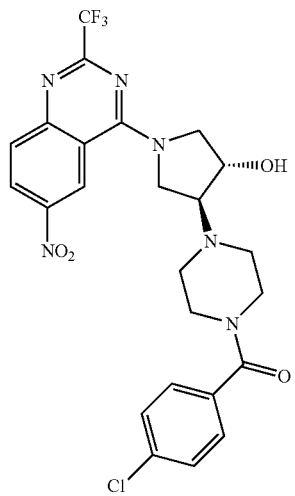
188
4-[4-(4-chlorobenzoyl)piperazin-1-yl]-1-[6-
nitro-2-(trifluoromethyl)quinazolin-4-
yl]pyrrolidin-3-ol
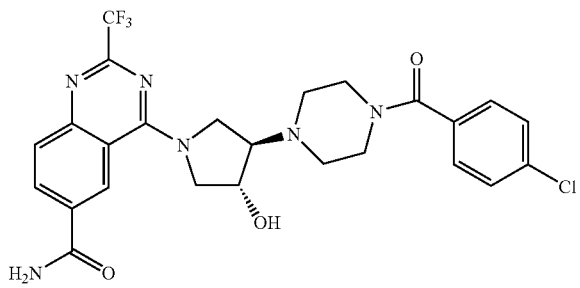
189
4-{(3R,4R)-3-[4-(4-chlorobenzoyl)piperazin-
1-yl]-4-hydroxypyrrolidin-1-yl}-2-
(trifluoromethyl)quinazoline-6-carboxamide
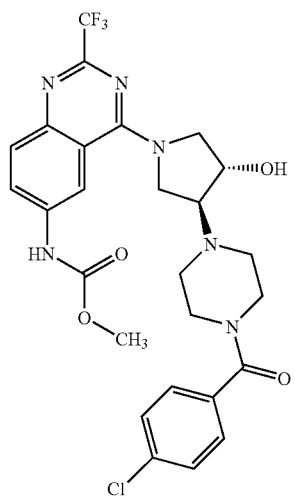
190
methyl [4-{3-[4-(4-chlorobenzoyl)piperazin-
1-yl]-4-hydroxypyrrolidin-1-yl}-2-
(trifluoromethyl)quinazolin-6-yl]carbamate TABLE 1-continued
Examples of Compounds of Formula I-A
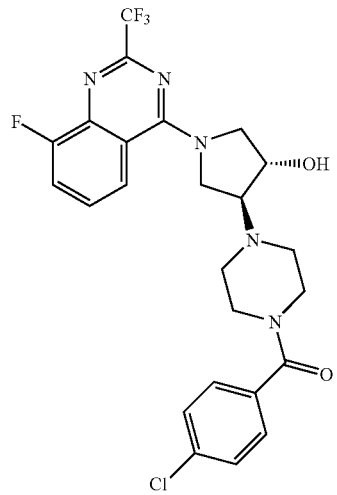
191
4-[4-(4-chlorobenzoyl)piperazin-1-yl]-1-[8-
fluoro-2-(trifluoromethyl)quinazolin-4-
yl]pyrrolidin-3-ol
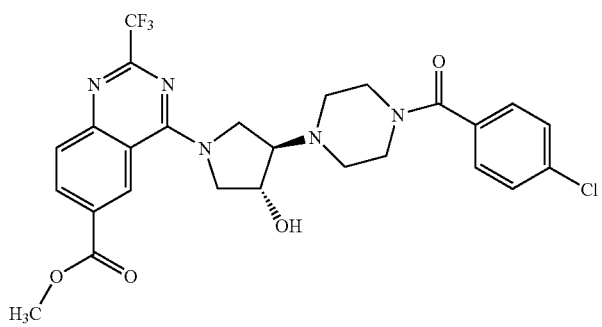
192
methyl 4-{(3R,4R)-3-[4-(4-
chlorobenzoyl)piperazin-1-yl]-4-
hydroxypyrrolidin-1-yl}-2-
(trifluoromethyl)quinazoline-6-carboxylate
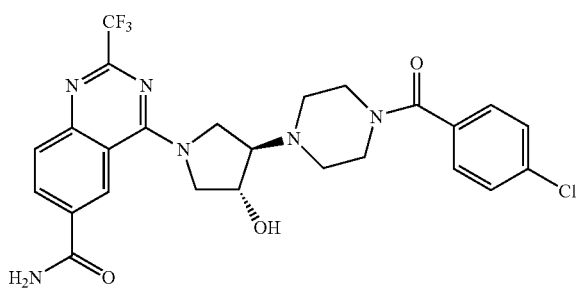
193
4-{(3R,4R)-3-[4-(4-chlorobenzoyl)piperazin-
1-yl]-4-hydroxypyrrolidin-1-yl}-2-
(trifluoromethyl)quinazoline-6-carboxamide TABLE 1-continued
Examples of Compounds of Formula I-A
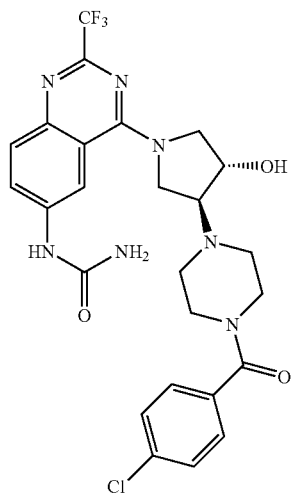
194
N-[4-{3-[4-(4-chlorobenzoyl)piperazin-1-yl]-
4-hydroxypyrrolidin-1-yl}-2-
(trifluoromethyl)quinazolin-6-yl]urea
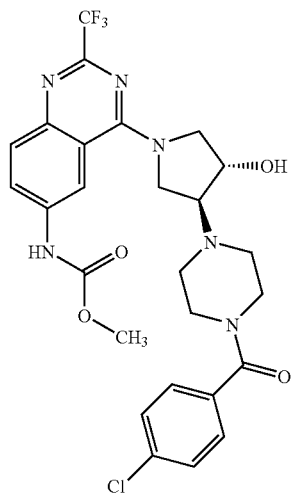
195
methyl [4-{(3S,4S)-3-[4-(4-
chlorobenzoyl)piperazin-1-yl]-4-
hydroxypyrrolidin-1-yl}-2-
(trifluoromethyl)quinazolin-6-yl]carbamate TABLE 1-continued
Examples of Compounds of Formula I-A
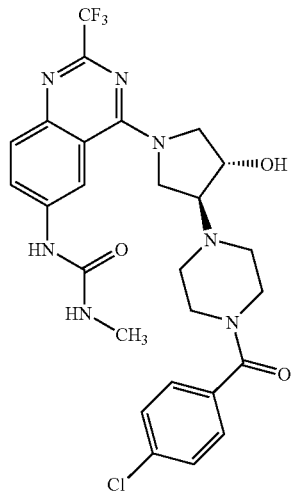
196
N-[4-{3-[4-(4-chlorobenzoyl)piperazin-1-yl]-
4-hydroxypyrrolidin-1-yl}-2-
(trifluoromethyl)quinazolin-6-yl]-N'-
methylurea
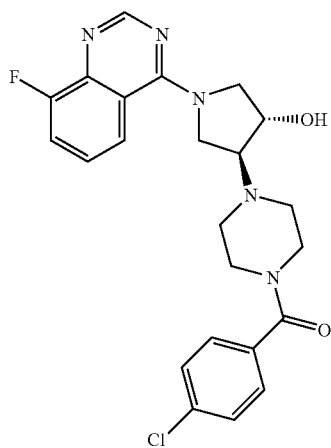
197
4-[4-(4-chlorobenzoyl)piperazin-1-yl]-1-(8-
fluoroquinazolin-4-yl)pyrrolidin-3-ol
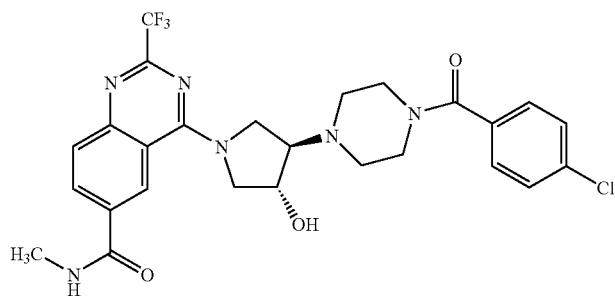
198
4-{3-[4-(4-chlorobenzoyl)piperazin-1-yl]-4-
hydroxypyrrolidin-1-yl}-N-methyl-2-
(trifluoromethyl)quinazoline-6-carboxamide TABLE 1-continued
Examples of Compounds of Formula I-A
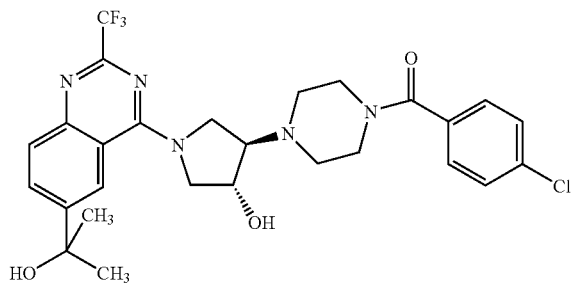
199
4-[4-(4-chlorobenzoyl)piperazin-1-yl]-1-[6-
(1-hydroxy-1-methylethyl)-2-
(trifluoromethyl)quinazolin-4-yl]pyrrolidin-
3-ol
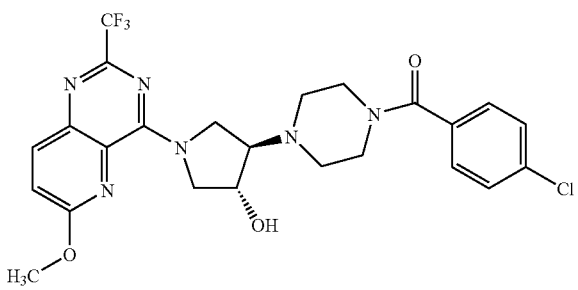
200
4-[4-(4-chlorobenzoyl)piperazin-1-yl]-1-[6-
methoxy-2-(trifluoromethyl)pyrido[3,2-
d]pyrimidin-4-yl]pyrrolidin-3-ol
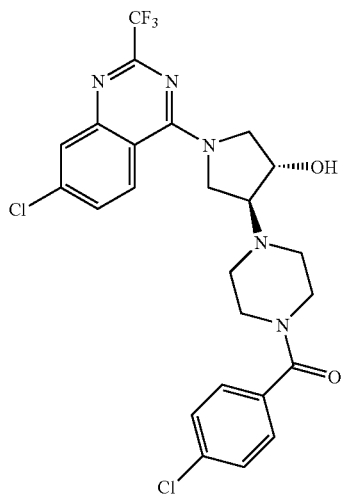
201
4-[4-(4-chlorobenzoyl)piperazin-1-yl]-1-[7-
chloro-2-(trifluoromethyl)quinazolin-4-
yl]pyrrolidin-3-ol TABLE 1-continued
Examples of Compounds of Formula I-A
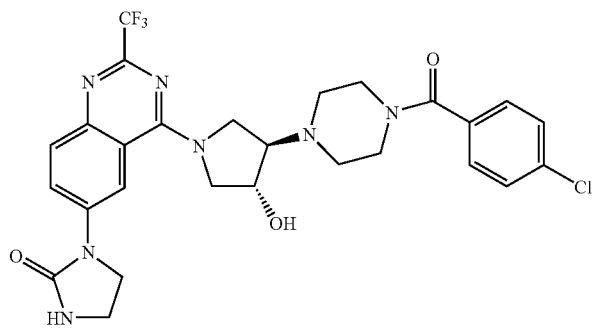
202
1-[4-{3-[4-(4-chlorobenzoyl)piperazin-1-yl]-
4-hydroxypyrrolidin-1-yl}-2-
(trifluoromethyl)quinazolin-6-
yl]imidazolidin-2-one
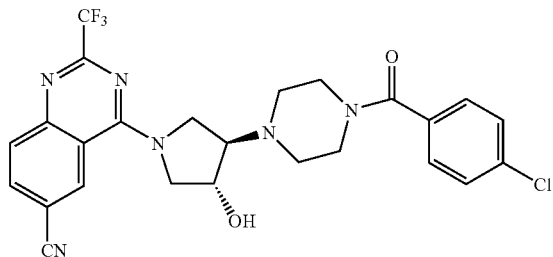
203
4-{3-[4-(4-chlorobenzoyl)piperazin-1-yl]-4-
hydroxypyrrolidin-1-yl}-2-
(trifluoromethyl)quinazoline-6-carbonitrile
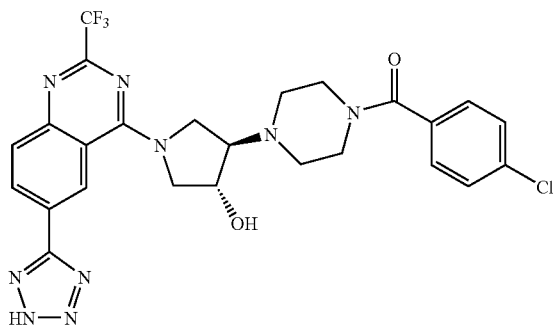
204
4-[4-(4-chlorobenzoyl)piperazin-1-yl]-1-[6-
(2H-tetrazol-5-yl)-2-
(trifluoromethyl)quinazolin-4-yl]pyrrolidin-
3-ol TABLE 1-continued Examples of Compounds of Formula I-A

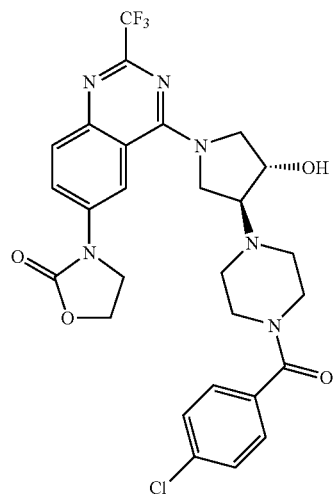

205
3-[4-{3-[4-(4-chlorobenzoyl)piperazin-1-yl]-
4-hydroxypyrrolidin-1-yl}-2-
(trifluoromethyl)quinazolin-6-yl]-1,3-
oxazolidin-2-one

4. General Synthetic Methods

The compounds of this invention may be prepared in general by methods known to those skilled in the art for analogous compounds, as illustrated by the general schemes below, and the preparative examples that follow.

Scheme I below shows a general method for preparing certain exemplary compounds of the invention. The route is exemplified for compounds where Ring A is a pyrrolidine ring, Ring B is a piperazine ring and $R^2$ is 4-chlorobenzoyl. It will be apparent to one skilled in the art that other compounds of formula I, where Ring B and $R^2$ are varied, may be prepared in an analogous manner.

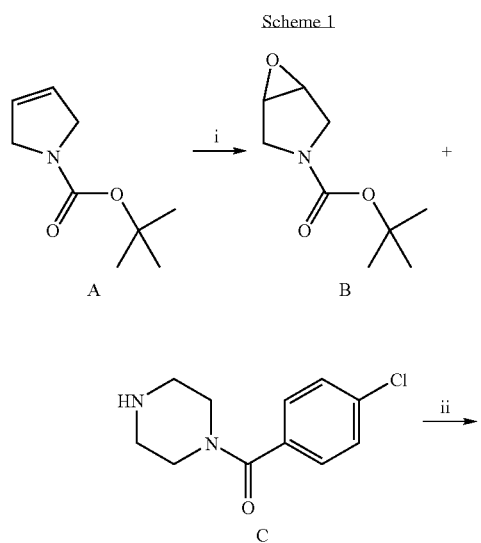

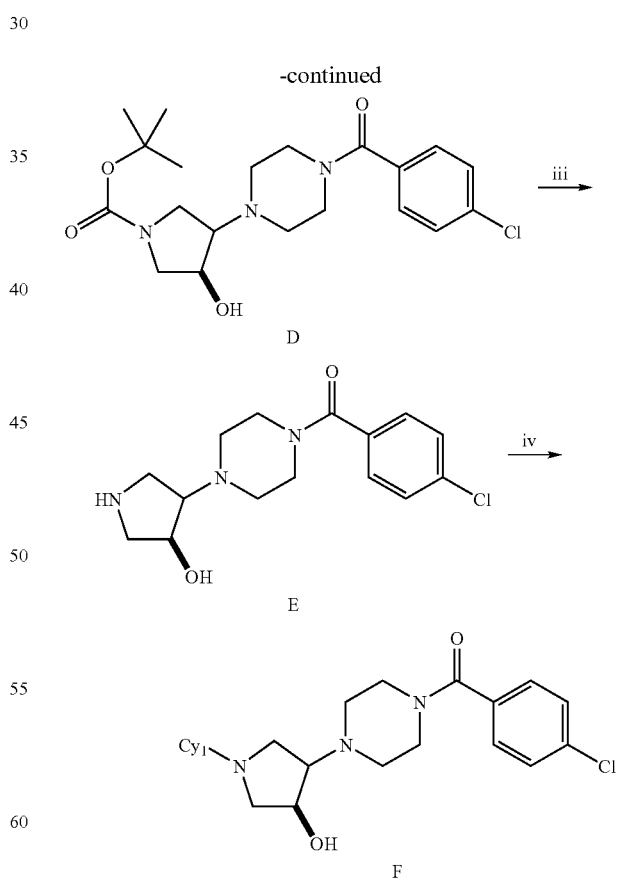

Reagents and conditions: (i) mCPBA, $CH_2Cl_2$; (ii) Procedure A: 130° C. or Procedure B: $Ca(OTf)_2$, $CH_3CN$, reflux; (iii) 4N HCl; (iv) Procedure C: $Cy_1$-Br, $Pd_2(DBA)_3$, BINAP, sodium t-butoxide, dioxane; or Procedure D: $Cy_1$-Cl, diisopropylethylamine, DMF; or Procedure E: $Cy_1$-Cl, DBU, DMP.

Scheme 2 below shows a general method for preparing certain exemplary compounds of the invention where $R^2$ is 4-chlorobenzyl.

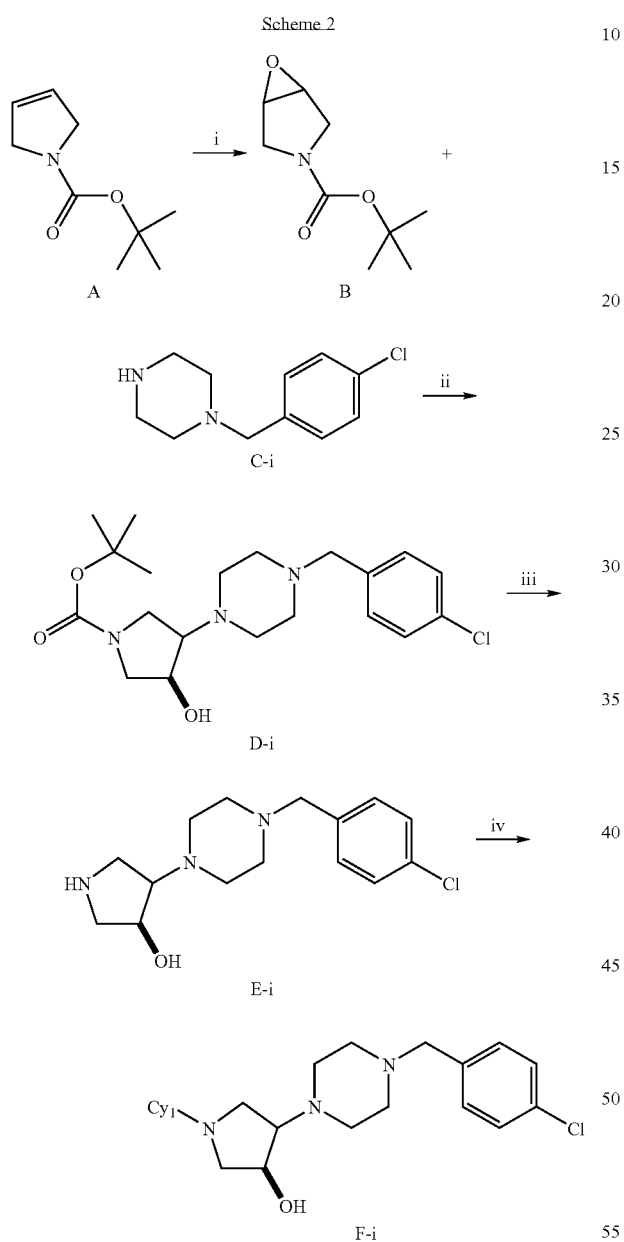

Reagents and conditions: (i) mCPBA, $CH_2Cl_2$; (ii) Procedure A: 130° C. or Procedure B: $Ca(OTf)_2$, $CH_3CN$, reflux; (iii) 4N HCl; (iv) Procedure C: $Cy_1$-Br, $Pd_2(DBA)_3$, BINAP, sodium t-butoxide, dioxane; or Procedure D: $Cy_1$-Cl, diisopropylethylamine, DMF; or Procedure E: $Cy_1$-Cl, DBU, DMP.

Certain intermediates that are useful for making the compounds of this invention are novel. Useful intermediates are compounds of formulae V, VI, VII, VIII, and IX:

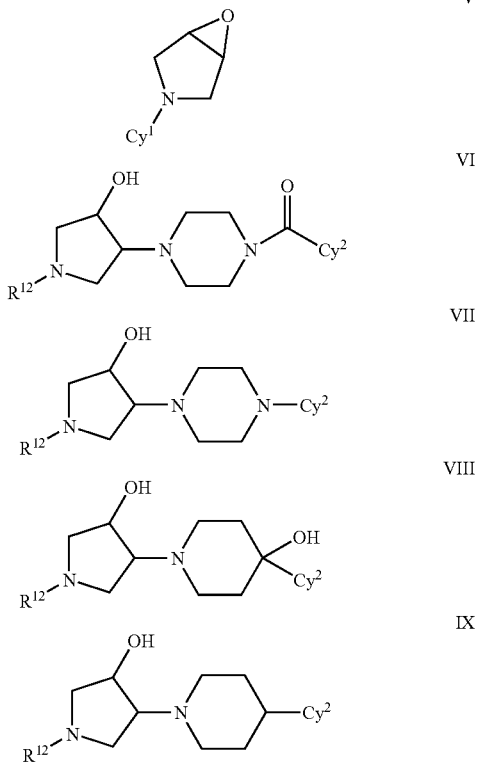

where $Cy^1$ and $Cy^2$ are as described above and $R^{12}$ is hydrogen or a protecting group. Suitable protecting groups are well known to those skilled in the art and include ester groups as tert-butoxycarbonyl and benzyloxycarbonyl, as well as other known protecting groups such as benzyl. Rings A and B of intermediates V-IX may be substituted as described above.

Although certain exemplary embodiments are depicted and described herein, it will be appreciated that compounds of the invention can be prepared according to the methods described generally above using appropriate starting materials by methods generally available to one of ordinary skill in the art. Additional embodiments are exemplified in more detail herein.

5. Uses, Formulation and Administration

As discussed above, the present invention provides compounds that are useful as inhibitors of chemokine receptors, preferably CCR1, and thus the present compounds are useful for treating or lessening the severity of a variety of acute or chronic inflammatory diseases, conditions, or disorders including, but not limited to, inflammatory arthritis, inflammatory demyelinating disease, atherosclerosis, arteriosclerosis, restenosis, ischemia/reperfusion injury, diabetes mellitus, psoriasis, inflammatory bowel diseases, rejection of a transplanted graft, graft versus host disease, allergy, asthma, cancer (including multiple myeloma), and osteolytic bone disorders.

Accordingly, in another aspect of the present invention, pharmaceutical compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a chemokine receptor, preferably CCR1.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, a method for the treatment or lessening the severity of an acute or chronic inflammatory disease or disorder is provided comprising administering an effective amount of a compound, or a pharmaceutical composition to a subject in need thereof. In yet another aspect, a method for treating or lessening the severity of cancer or an osteolytic bone disorder is provided comprising administering an effective amount of a compound, or a pharmaceutical composition to a subject in need thereof. In certain embodiments of the present invention an "effective amount" of the compound or pharmaceutical composition is that amount effective for treating or lessening the severity of an acute or chronic inflammatory disease or disorder, or is that amount effective for treating or lessening the severity of cancer or an osteolytic bone disorder. In other embodiments, an "effective amount" of a compound is an amount which inhibits binding of chemokine to receptor (e.g., CCR1) and thereby inhibits one or more processes mediated by the binding in a subject with a disease associated with pathogenic leukocyte recruitment, pathogenic leukocyte activation or pathogenic leukocyte recruitment and activation. Examples of such processes include leukocyte migration, integrin activation, transient increases in the concentration of intracellular free calcium $[Ca^{2+}]_i$ and granule release of proinflammatory mediators. An "effective amount" of a compound can achieve a desired therapeutic and/or prophylactic effect, such as an amount which results in the prevention of or a decrease in the symptoms associated with a disease associated with pathogenic leukocyte recruitment, pathogenic leukocyte activation or pathogenic leukocyte recruitment and activation.

The compounds and compositions, according to the method of the present invention, may be administered using any amount and any route of administration effective for treating or lessening the severity of an acute or chronic inflammatory disease or disorder. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of chemokine receptor interactions and thus the invention further relates to a method for treating (e.g., palliative, curative, prophylactic) a disease or disorder associated with pathogenic leukocyte recruitment, activation or recruitment and activation, mediated by chemokines or chemokine receptor function including chronic and acute inflammatory disorders.

In one embodiment, the compounds and compositions of the invention are inhibitors of CCR1, and thus, without wishing to be bound by any particular theory, the compounds and compositions are particularly useful for treating or lessening the severity of a disease, condition, or disorder where activation of CCR1 is implicated in the disease, condition, or disorder. When activation of CCR1 is implicated in a particular disease, condition, or disorder, the disease, condition, or disorder may also be referred to as a "CCR1-mediated disease" or disease symptom. Accordingly, in another aspect, the present invention provides a method for treating or lessening the severity of a disease, condition, or disorder where activation or one or more of CCR1 is implicated in the disease state.

As used herein "pathogenic leukocyte recruitment, activation or recruitment and activation" refers to leukocyte recruitment (e.g., accumulation of leukocytes at a sight of inflammation or injury) and/or activation (e.g., physiologic state in which leukocytes perform effector functions) that contributes to the conditions, processes or results of the disease or disorder to be treated. For example, in a subject afflicted with multiple sclerosis, recruitment and/or activation of T cells in the central nervous system is considered "pathogenic leukocyte recruitment, pathogenic leukocyte activation or pathogenic leukocyte recruitment and activation," because recruited and activated T cells contribute to the demyelination characteristic of that disease. Similarly, in a subject afflicted with rheumatoid arthritis, recruitment and/or activation of T cells in joints (e.g., synovial tissue or fluid) is considered "pathogenic leukocyte recruitment, pathogenic leukocyte activation or pathogenic leukocyte recruitment and activation," because recruited and activated T cells contribute to the tissue destruction characteristic of rheumatoid arthritis.

Diseases and disorders characterized by pathogenic leukocyte recruitment, pathogenic leukocyte activation or pathogenic leukocyte recruitment and activation that can be treated according to the methods described herein include, for example, acute and chronic inflammatory disorders characterized by the presence of CCL2 (MCP-1) CCL3 (MIP-1α), CCL4 (MIP-1β., CCL5 (RANTES), CCL7 (MCP-3), CCL8 (MCP-2), CCL13 (MCP-4), CCL14 (HCC-1), CCL15 (Lkn-1) and/or CCL23 (MPIF-1) responsive cells, such as T cells, monocytes or eosinophils. Such diseases or disorders include, but are not limited to, inflammatory arthritis (e.g., rheumatoid arthritis), inflammatory demyelinating disease (e.g., multiple sclerosis), atherosclerosis, arteriosclerosis, restenosis, ischemia/reperfusion injury, diabetes mellitus (e.g., type 1 diabetes mellitus), psoriasis, chronic obstructive pulmonary disorder (COPD), inflammatory bowel diseases such as ulcerative colitis and Crohn's disease, rejection (acute or chronic) of transplanted organs and tissues (e.g., acute allograft rejection, chronic allograft rejection), graft versus host disease, as well as allergies and asthma. Other diseases associated with aberrant leukocyte recruitment and/or activation which can be treated (including prophylactic treatments) with the methods disclosed herein are inflammatory diseases associated with viral (e.g., Human Immunodeficiency Virus (HIV)), bacterial or fungal infection, such as, AIDS associated encephalitis, AIDS related maculopapular skin eruption, AIDS related interstitial pneumonia, AIDS related enteropathy, AIDS related periportal hepatic inflammation and AIDS related glomerulo nephritis. Still other diseases include, but are not limited to cancer and osteolytic bone disorders. The method comprises administering to the subject in need of treatment an effective amount of a compound (i.e., one or more compounds) described herein.

As used herein "inflammatory demyelinating disease" refers to acute and chronic inflammatory diseases characterized by demyelination of central nervous system tissue. The inflammatory demyelinating disease can be an acute inflammatory demyelinating disease, for example, acute disseminated encephalomyelitis, Guillain-Barre syndrome or acute hemorrhagic leukoencephalitis. In other embodiments, the inflammatory demyelinating disease can be a chronic inflammatory demyelinating disease, for example, multiple sclerosis, chronic inflammatory demyelinating polyradiculoneuropathy.

In a preferred embodiment, the invention provides a method of treating multiple sclerosis, comprising administering an effective amount of compounds of general formula I (and subsets thereof as described herein) to a subject in need thereof. The manifestation of MS is variable and the clinical course of MS can be grouped into four categories: relapsing-remitting, primary progressive, secondary progressive and progressive-relapsing. The method of the invention can be used to treat MS which presents with each of the recognized clinical courses. Accordingly, a compound of the invention can be administered to a patient with a progressive course of MS to retard or prevent the progression of neurological impairment. A compound of the invention can also be administered to a subject with relapsing-remitting, secondary progressive or progressive-relapsing MS to inhibit relapse (e.g., an acute attack). For example, a compound of the invention can be administered to a subject with relapsing-remitting MS during the remitting phase of the disease to prevent or delay relapse.

As used herein, "inflammatory arthritis" refers to those diseases of joints where the immune system is causing or exacerbating inflammation in the joint, and includes rheumatoid arthritis, juvenile rheumatoid arthritis and spondyloarthropathies, such as ankylosing spondylitis, reactive arthritis, Reiter's syndrome, psoriatic arthritis, psoriatic spondylitis, enteropathic arthritis, enteropathic spondylitis, juvenile-onset spondyloarthropathy and undifferentiated spondyloarthropathy. Inflammatory arthritis is generally characterized by infiltration of the synovial tissue and/or synovial fluid by leukocytes.

In another preferred embodiment, the invention provides a method of treating rheumatoid arthritis, comprising administering an effective amount of a compound of general formula I (and subsets as described herein) to a subject in need thereof.

The activity of compounds of the present invention can be assessed using suitable assays, such as receptor binding assays or chemotaxis assays. For example, as described in the Examples, small molecule antagonists of MIP-1α binding have been identified utilizing THP-1 cells membranes. Specifically, a high through-put receptor binding assay, which monitors $^{125}$I-MIP-1α binding to THP-1 cell membranes, was used to identify small molecule antagonists which block binding of MIP-1α. Compounds of the present invention can also be identified by virtue of their ability to inhibit the activation steps triggered by binding of a chemokine (e.g., CCL2 (MCP-1) CCL3 (MIP-1α), CCL4 (MIP-1β., CCL5 (RANTES), CCL7 (MCP-3), CCL8 (MCP-2), CCL13 (MCP-4), CCL14 (HCC-1), CCL15 (Lkn-1), CCL23 (MPIF-1)) to its receptor (CCR-1), such as chemotaxis, integrin activation and granule mediator release. They can also be identified by virtue of their ability to block chemokine (e.g., CCL2 (MCP-1) CCL3 (MIP-1α), CCL4 (MIP-1β., CCL5 (RANTES), CCL7 (MCP-3), CCL8 (MCP-2), CCL13 (MCP-4), CCL14 (HCC-1), CCL15 (Lkn-1), CCL23 (MPIF-1)) induced chemotaxis of, for example, HL-60 cells, T-cells, peripheral blood mononuclear cells or eosinophils.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents which are normally administered to treat or prevent a particular disease, or condition, are known as "appropriate for the disease, or condition, being treated".

For example, compounds of the invention can also be administered in combination with one or more additional therapeutic agents, such as, theophylline, β-adrenergic bronchodilators, corticosteroids, antihistamines, antiallergic agents, immunosuppressive agents (e.g., cyclosporin A, FK-506, prednisone, methylprednisolone), hormones (e.g., adrenocorticotropic hormone (ACTH)), cytokines (e.g., interferons (e.g., IFNβ-1a, IFNδ-1b)), anticancer agents, and the like.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Another aspect of the invention relates to inhibiting chemokine receptor, preferably CCR1, activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of chemokine receptor, preferably CCR1, activity in a biological sample is useful for a variety of purposes that are known to one of skill in the art. Examples of such purposes include, but are not limited to, blood transfusion, organ-transplantation, biological specimen storage, and biological assays.

Synthetic Procedures

Examples 1-5 below depict the synthesis of intermediates A, B, C, D, and E, as referred to in Scheme 1, which intermediates are useful for the preparation of compounds of the invention.

EXAMPLE 1

Synthesis of 2,5-Dihydro-pyrrole-1-carboxylic acid tert-butyl ester (A) and 6-Oxa-3-aza-bicyclo[3.1.0] hexane-3-carboxylic acid tert-butyl ester (B)

2,5-Dihydro-pyrrole-1-carboxylic acid tert-butyl ester (A)

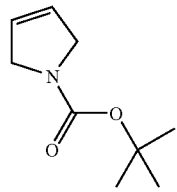

A

Pyrroline (65% purity, 20 g) was dissolved in CH$_2$Cl$_2$ (500 mL), Et$_3$N (44 mL, 1.1 eq) was added. The mixture was cooled to 0° C. Boc anhydide (68 g, 1.01 eq) was added very slowly at 0° C. Finally the reaction mixture was stirred at 0° C. to RT for overnight. The reaction mixture was washed with 1N NaOH solution (2×100 mL). The organic phase was dried over Na$_2$SO$_4$. The resulting oil was purified by column chromatography (Hexane:Ethyl Acetate 3:1) to give 46.46 g of desired product as a colorless oil (95% yield, 65% purity). $^1$H-NMR (300 MHz, CDCl$_3$): δ 1.45 (s, 9 H), 4.08 (d, 4 H), 5.73 (d, 2 H)

6-Oxa-3-aza-bicyclo[3.1.0]hexane-3-carboxylic acid tert-butyl ester (B)

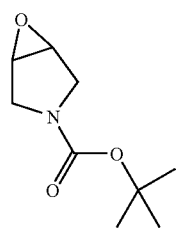

B 2,5-Dihydro-pyrrole-1-carboxylic acid tert-butyl ester (46 g, 65% purity) was dissolved in CH$_2$Cl$_2$ (500 mL). The solution was cooled to 0° C. mCPBA (122 g, 2 eq, 77% purity) was slowly added to the solution at 0° C. The reaction mixture was stirred at 0° C. to RT for overnight. The mixture was concentrated to 200 ml, and filtered. The organic phase was washed with 1 N NaOH solution (4×100 mL), dried over Na$_2$SO$_4$. The resulting oil was purified by column chromatography (hexane:ethyl acetate 3:1) to give 28 g of desired product as a colorless oil (87% yield). $^1$H-NMR (300 MHz, CDCl$_3$): δ 1.41 (s 9 H), 3.26 (dd, 2 H), 3.25-3.80 (m, 4 H)

EXAMPLE 2

Synthesis of (4-Chloro-phenyl)-piperazin-1-yl-methanone (C)

Step 1: 4-(4-Chloro-benzoyl)-piperazine-1-carboxylic acid tert-butyl ester

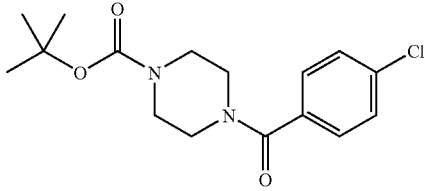

Piperazine-1-carboxylic acid tert-butyl ester (16 g) was dissolved in CH$_2$Cl$_2$ (150 mL). Et$_3$N (13.16 mL, 1.1 eq) and Cat. DMAP were added. The mixture was cooled to 0° C. Acid chloride (11.47 mL, 1.05 eq) was added very slowly at 0° C. Finally the reaction mixture was stirred at 0° C. to RT for overnight. The reaction mixture was washed with 1N NaOH solution (2×100 mL). The organic phase was dried over Na$_2$SO$_4$. The desired product was purified by recrystallization in EtOAc (26 g, 93% yield). $^1$H-NMR (300 MHz, CDCl$_3$): δ 1.44 (s, 9 H), 3.20-3.80 (m, 8 H), 7.34 (d, 2 H), 7.36 (d, 2 H) Retention Time (LC, method: Formic acid standard): 1.81 min. MS (M+H$^+$): 325

Step 2: (4-Chloro-phenyl)-piperazin-1-yl-methanone (C)

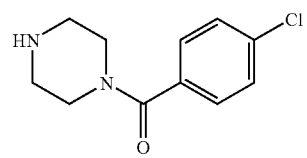

C 4-(4-Chloro-benzoyl)-piperazine-1-carboxylic acid tert-butyl ester (26 g) was dissolved in CH$_2$Cl$_2$ (350 mL). 4M HCL/Dioxane (150 mL) was added. The mixture was stirred at RT for 4 h. White precipitate was formed. The mixture was concentrated. The white solid was washed with Et$_2$O. After the white solid was treated with 1N NaOH (200 mL) and extracted with Ethyl acetate (3×100 mL), the combined organic phase was dried over Na$_2$SO$_4$ and concentrated to give 17.79 g of desired product (99% yield). $^1$H-NMR (for HCl salt) (300 MHz, MeOD): δ 2.80-2.90 (m, 4 H), 3.20-3.80 (m, 4 H), 7.29-7.36 (m, 4 H).

EXAMPLE 3

3-[4-(4-Chloro-benzoyl)-piperazin-1-yl]-4-hydroxy-pyrrolidine-1-carboxylic acid tert-butyl ester (D)

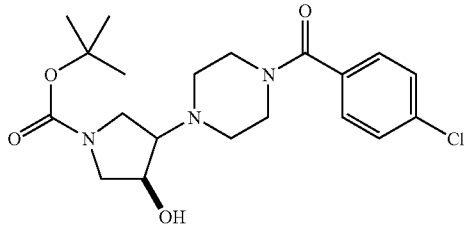

This is an example of Procedure A in Scheme 1 above. 6-Oxa-3-aza-bicyclo[3.1.0]hexane-3-carboxylic acid tert-butyl ester (1.85 g 1 eq) and (4-Chloro-phenyl)-piperazin-1-yl-methanone (2.2 g 1 eq) were added into a sealed tube. The mixture was heated to 130° C. for 5 h. The resulting oil was purified by column chromatography (EtOAc:MeOH:Et$_3$N 10:1:0.01) to give 3.38 g of desired product as a sticky oil (84% yield). $^1$H-NMR (300 MHz, DMSO): δ 1.43 (s, 9 H), 2.40-2.80 (m, 4H), 3.15-3.85 (m, 9 H), 4.26-4.30 (m, 1 H), 7.35 (d, 2 H), 7.38 (d, 2 H) Retention Time (LC, method: Formic acid polar): 1.19 min. MS (M+H$^+$): 410

EXAMPLE 4

3-[4-(4-Chloro-benzoyl)-piperazin-1-yl]-4-hydroxy-pyrrolidine-1-carboxylic acid tert-butyl ester (D) (same as Example 3 using a Different Procedure)

This is an example of Procedure B in Scheme 1 above. 6-Oxa-3-aza-bicyclo[3.1.0]hexane-3-carboxylic acid tert-butyl ester (0.5 g 1 eq) and (4-Chloro-phenyl)-piperazin-1-yl-methanone (0.6 g 1 eq) were dissolved in CH$_3$CN (5 mL). Ca(OTf)$_2$ (0.456 g, 0.5 eq) was added into the mixture. Reaction mixture was stirred at RT for overnight, then 80-85° C. for 8 h. After concentrating and adding EtOAc 20 mL to the residue, the organic phase was washed with H$_2$O, dried over Na$_2$SO$_4$. The resulting oil was purified by column chromatography (EtOAc:MeOH:Et$_3$N 10:1:0.01) to give 1.01 g of desired product as a sticky oil (92% yield). * It is important to note that during workup, the organic phase should be washed with H$_2$O and saturated NaCl solution, not saturated NaHCO$_3$ solution.

EXAMPLE 5

(4-Chloro-phenyl)-[4-(4-hydroxy-pyrrolidin-3-yl)-piperazin-1-yl]-methanone (E)

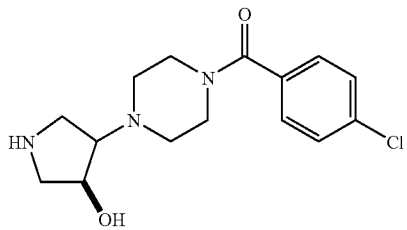

3-[4-(4-Chloro-benzoyl)-piperazin-1-yl]-4-hydroxy-pyrrolidine-1-carboxylic acid tert-butyl ester was dissolved in CH$_2$Cl$_2$. 4M HCl/dioxane (150 mL) was added. The mixture was stirred at RT for 4 h. White precipitate was formed. The mixture was diluted with ether, filtered. The white solid was washed with ether and dried to give desired product (99% yield). $^1$H-NMR (300 MHz, DMSO, HCl salt): δ 3.0-4.0 (m, 12 H), 4.85 (m, 2 H), 7.25 (d, 2 H), 7.54 (d, 2 H) Retention Time (LC method: formic acid polar): 1.01 min. MS (M+H$^+$): 310

Examples 6 and 7 below describe the synthesis of intermediates D-i, and E-i, as referred to in Scheme 2, which intermediates are useful for the preparation of compounds of the invention.

EXAMPLE 6

3-[4-(4-Chloro-benzyl)-piperazin-1-yl]-4-hydroxy-pyrrolidine-1-carboxylic acid tert-butyl ester (D-i)

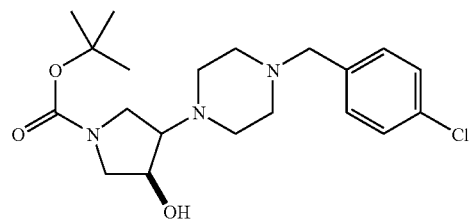

6-Oxa-3-aza-bicyclo[3.1.0]hexane-3-carboxylic acid tert-butyl ester (5.0 1.05 eq) and 1-(4-Chloro-benzyl)-piperazine (5.04 g 1 eq) were dissolved in CH$_3$CN (250 mL).a(OTf)$_2$ (4.35 g, 0.5 eq) was added into the mixture. Reaction mixture was refluxed overnight. After concentrating, added EtOAc (100 mL) and filtered. The organic phase was washed with satd. NaHCO$_3$ and water. Dried the organic phase over MgSO$_4$ and purified by column chromatography (EtOAc:MeOH:Et$_3$N 10:1:0.01) to give 4.5 g of white solid. $^1$H-NMR (300 MHz, CDCl$_3$): δ 1.42 (s, 9 H), 2.05-3.0 (s, 9 H), 3.15-3.25 (m, 2 H), 3.45 (s, 2 H), 3.46-3.80 (m, 2 H), 4.28 (dd, 1 H), 7.20-7.29 (m, 4 H) Retention Time (LC, method: Formic acid stardard): 1.09 min. MS (M+H$^+$): 396

EXAMPLE 7

4-[4-(4-Chloro-benzyl)-piperazin-1-yl]-pyrrolidin-3-ol

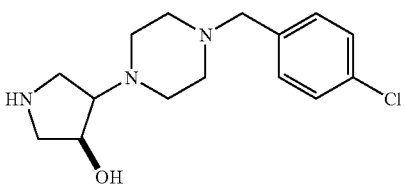

The desired compound was prepared from 3-[4-(4-Chloro-benzyl)-piperazin-1-yl]-4-hydroxy-pyrrolidine-1-carboxylic acid tert-butyl ester in a manner similar to that described in Example 5. $^1$H-NMR (300 MHz, DMSO, HCl salt): δ 2.80-3.60 (m, 12 H), 4.20-4.35 (m, 4 H), 7.51 (d, 2 H), 7.66 (d, 2 H). Retention Time (LC, method: Formic acid polar): 0.68 min. MS (M+H$^+$): 296

Examples 8-10 exemplify the synthesis of intermediates useful for preparation of compounds of the invention where Ring B is a [1,4]diazepane ring. The unprotected pyrrolidinyl-diazepane ring can then be coupled to a desired $Cy^1$ group using the conditions described for Procedure C, D, or E (as shown in Schemes 1 and 2 and as described generally above).

EXAMPLE 8

1-(4-Chloro-phenyl)-[1,4]diazepane

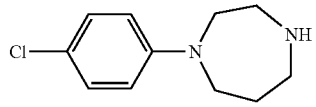

To a solution of [1,4]-diazepane-1-carboxylic acid tert-butyl ester (1.94 mL, 10.0 mmol) in toluene (20 mL) was added 1-Bromo-4-chloro-benzene (2.52 g, 13.0 mmol), Palladium dibenzylideneacetone ($Pd_2(dba)_3$, 0.229 g, 0.250 mmol), sodium tert-butoxide (2.50 g, 26 mmol) and BINAP (0.311 g, 0.500 mmol). The solution was stirred at reflux for 23 hours under nitrogen atmosphere. The reaction was filtered trough a pad of celite, and the cake was rinsed with ethyl acetate. The combined organic layers were washed with water, brine, and evaporated in vacuo. The residue was purified by silica gel plug filtration (80:20 hexane:ethyl acetate) to yield 3.1 g (~100%) of the Boc-protected intermediate, which was used without further purification.

The crude 4-(4-Chloro-phenyl)-[1,4]diazepane-1-carboxylic acid tert-butyl ester (3.10 g, 10.0 mmol) was dissolved in methylene chloride (1 mL) and treated with 4 N HCl/dioxane (10 mL, 40 mmol). The solution was stirred at rt for 1 hour. The reaction was concentrated in vacuo. The residue was diluted with saturated aqueous sodium bicarbonate (100 mL) and extracted with ethyl acetate (3×30 mL). The combined organics were washed with brine, dried over $MgSO_4$, and evaporated to yield 1.00 g (48%) of the title compound. $^1$H-NMR ($CDCl_3$) δ: 1.90 (2H, m), 2.23 (1H, brs), 2.83 (2H, m), 3.02 (2H, m), 3.54 (4H, m), 6.58 (2H, d, j=9.3 Hz), 7.13 (2H, d, j=9.3 Hz). ESI-MS m/z: 211 (M+1), FAS method rt: 1.04 min.

EXAMPLE 9

Trans-3-[4-(4-Chloro-phenyl)-[1,4]diazepan-1-yl]-4-hydroxy-pyrrolidine-1-carboxylic acid tert-butyl ester

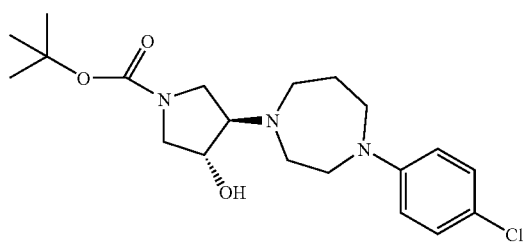

To a solution of 1-(4-Chloro-phenyl)-[1,4]diazepane (1.00 g, 4.80 mmol) in acetonitrile (10 mL) was added 6-oxa-3-azabicyclo[3.1.0]hexane-3-carboxylic acid tert-butyl ester (0.925 g, 5.00 mmol) and calcium(II) trifluoromethanesulfonate (0.676 g, 2.00 mmol). The solution was stirred at 80° C. for 17 hours under nitrogen atmosphere. The reaction was concentrated in vacuo. The residue was diluted with saturated aqueous sodium bicarbonate (50 mL) and extracted with ethyl acetate (3×30 mL). The combined organics were washed with brine, dried over $MgSO_4$, and evaporated. The residue was purified by silica gel chromatography (gradient ethyl acetate to 87:10:3 ethyl acetate:methanol:triethylamine) to yield 0.819 g (41%) of the title compound. ESI-MS mz: 396 (M+1), FAS method rt: 1.25 min

EXAMPLE 10

Trans-4-[4-(4-Chloro-phenyl)-[1,4]diazepan-1-yl]-pyrrolidin-3-ol

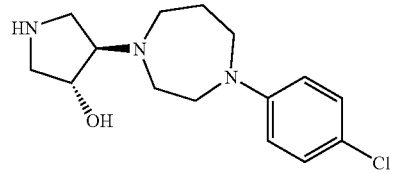

To a solution of trans-3-[4-(4-Chloro-phenyl)-[1,4]diazepan-1-yl]-4-hydroxy-pyrrolidine-1-carboxylic acid tert-butyl ester (0.820 g, 2.08 mmol) in methylene chloride (1 mL) was added 4 N HCl/dioxane (10 mL, 40 mmol). The solution was stirred at rt for 1 hour, upon which a brown precipitate formed. The reaction was concentrated in vacuo to yield 0.930 g (~100%) of the title compound. ESI-MS m/z: 296 (M+1), FAS method rt: 0.83 min.

Example 11 below exemplifies the synthesis of an intermediate useful for the preparation of compounds of the invention where Ring B is a piperidinyl ring and $R^2$ is 4-chlorophenyloxy. This intermediate can then be used to prepare other intermediates and ultimately compounds of the invention as described generally above and herein. For example, this compound can be reacted with intermediate B (Schemes I and 2 above) to generate an intermediate suitable for reacting with a desired $Cy^1$ group.

EXAMPLE 11

4-(4-Chloro-phenoxy)-piperidinecarboxylic acid t-butylester

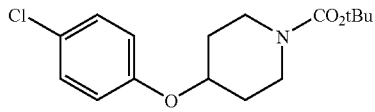

4-Hydroxy-piperidine-1-carboxylic acid tert-butyl ester (1.61 g, 8 mmol), 4-chloro-phenol (1.23 g, 9.6 mmol), $Ph_3P$ (2.30 g, 8.8 mmol) and DEAD (1.4 mL, 8.8 mmol) were added to 20 mL THF and let it stir at room temperature for overnight. The reaction mixture was partitioned in ether and 1M NaOH. The organic phase was washed with 1M NaOH, water and brine, dried over $Na_2SO_4$ and concentrated down to dryness. The resulting crude residue was purified by column chromatography on silica (hexane:ethyl acetate 5% to 15%)

to give 1.82 g tert-butylester of 4-(4-chloro-phenoxy)-piperidine. From the foregoing ester, 4-(4-chloro-phenoxy)-piperidine was obtained in about 99% by deprotection of the Boc group as described above.

Examples 12-14 below describe general procedures for the coupling of $Cy^1$ (via $Cy^1$-halide) to the pyrrolidinyl nitrogen atom (as depicted for some embodiments in Schemes I and 2)

EXAMPLE 12

General Arylation Procedure C (as referred to in Schemes I and 2) (Buchwald Reaction)

The bi-HCl or tri-HCl salt of the desired amines (1 eq), aryl bromides (1 eq), $Pd_2(dba)_3$ (0.0125 eq), BINAP (0.0375 eq) and sodium tert-butoxide (5 eq) were dissolved in dioxane (anhydrous, 2 mL) under Argon. The reaction mixture was stirred at 100° C. overnight. After cooling to room temperature, the mixture was concentrated. Ethyl acetate (4 mL) was added to the residue. The organic phase was washed with Saturated $Na_2CO_3$, dried over $Na_2SO_4$, and concentrated. The resulting solid was washed with ethyl acetate and methanol to provide the desired product.

EXAMPLE 13

General Arylation Procedure D (as referred to in Schemes I and 2) ($S_NAr$ Reaction)

The appropriate bi-HCl or tri-HCl salt of the desired amines (1 eq), aryl chloride (1 eq) and DIPEA (3-4 eq) were dissolved in DMF (0.5 mL). The reaction mixture was stirred at 90° C. overnight. After cooling to room temperature, the mixture was concentrated. Ethyl acetate (4 mL) was added to the residue. The organic phase was washed with Saturated $Na_2CO_3$, dried over $Na_2SO_4$, and concentrated. The residue was purified by column chromatography (Ethyl acetate:Methanol:$Et_3N$: 10:1:0.1) to give the desired product

EXAMPLE 14

General Arylation Procedure E (as referred to in Schemes I and 2)

1-Chloro-isoquinoline (176 mg, 1.07 mmol), piperazine-1-carboxylic acid tert-butyl ester (420 mg, 2.26 mmol) and DBU (0.25 mL, 1.61 mmol) were added into DMP (2 mL). The mixture was heated to 105-110° C. for overnight. The residue was diluted with water and extracted with ether. The organic layer was washed with brine, dried over $Na_2SO_4$ and concentrated in vacuo to dryness. The resulting residue was purified by column chromatography (5% to 10% ethyl acetate/hexane) to give 222 mg of the desired product 4-isoquinolin-1-yl-piperazine-1-carboxylic acid tert-butyl ester (yield: 66%).

Examples 15-20 below describe the synthesis of certain exemplary compounds of the invention where $Cy^1$ is a substituted aryl group. It will be appreciated that compounds as described generally herein and as exemplified in Table 1 herein can be prepared according to the methods described above and herein.

EXAMPLE 15

{4-[1-(4-Chloro-2-nitro-phenyl)-4-hydroxy-pyrrolidin-3-yl]-piperazin-1-yl}-(4-chloro-phenyl)-methanone

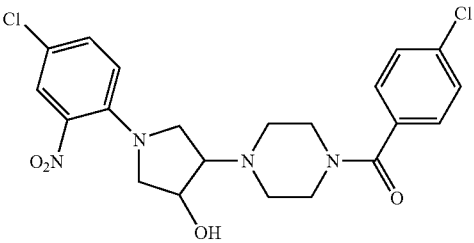

Following general procedures described above, the title compound was obtained as a yellow solid (90% yield), by using 4-chloro-2-fluoro-1-nitro-benzene as the starting material. MS: (ESI), M/Z, 465 (M+1). Retention time: 2.22 min (FA-polar).

EXAMPLE 16

Acetic acid 4-[4-(4-chloro-benzoyl)-piperazin-1-yl]-1-(4-chloro-2-ureido-phenyl)-pyrrolidin-3-yl ester Step 1: Acetic acid 4-[4-(4-chloro-benzoyl)-piperazin-1-yl]-1-(4-chloro-2-nitro-phenyl)-pyrrolidin-3-yl ester

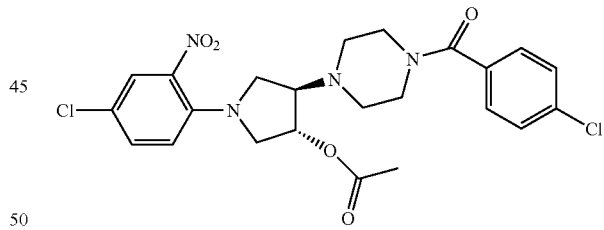

To a solution of {4-[1-(4-chloro-2-nitro-phenyl)-4-hydroxy-pyrrolidin-3-yl]-piperazin-1-yl}-(4-chloro-phenyl)-methanone (300 mg, 0.64 mmol) in $CH_2Cl_2$ (5 mL) at 0° C., was added $Et_3N$ (0.2 mL, 1.42 mmol) and acetyl chloride (112 mg, 1.42 mmol). The mixture was stirred at RT for overnight. The organic phase was washed with Saturated $NaHCO_3$, dried over $Na_2SO_4$, and concentrated. The residue was purified by column chromatography (Ethyl acetate) to give the desired product (160 mg, 50% yield) as a yellow oil. MS: (ESI), M/Z, 507(M+1). Retention time: 2.59 min (FA-polar).

Step 2: Acetic acid 1-(2-amino-4-chloro-phenyl)-4-[4-(4-chloro-benzoyl)-piperazin-1-yl]-pyrrolidin-3-yl ester

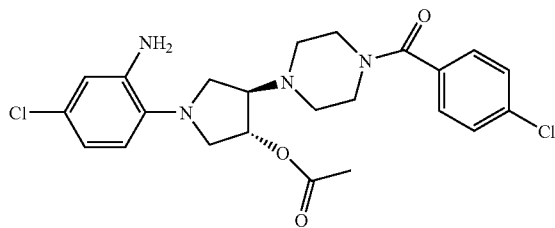

To a solution of acetic acid 4-[4-(4-chloro-benzoyl)-piperazin-1-yl]-1-(4-chloro-2-nitro-phenyl)-pyrrolidin-3-yl ester (140 mg, 0.31 mmol) in ethanol (1 mL), was added Pt (S) (28 mg, 20 weight %) and $HCOONH_4$ (87 mg, 1.38 mmol). The mixture was stirred at reflux for 1 h. After cooling, the mixture was filtered through celite and concentrated to give the desired compound as a light purple oil (67 mg, 50% yield). MS: (ESI), M/Z, 477(M+1). Retention time: 2.28 min (FA-polar).

Step 3: Acetic acid 4-[4-(4-chloro-benzoyl)-piperazin-1-yl]-1-(4-chloro-2-ureido-phenyl)-pyrrolidin-3-yl ester

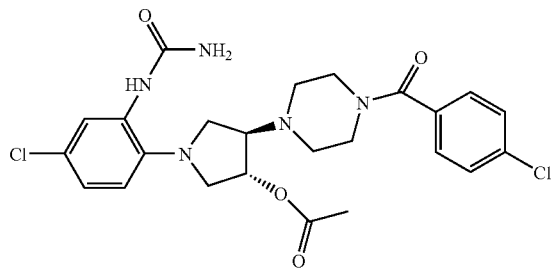

To a solution of acetic acid 1-(2-amino-4-chloro-phenyl)-4-[4-(4-chloro-benzoyl)-piperazin-1-yl]-pyrrolidin-3-yl ester (66 mg, 0.138 mmol) in 2 mL of $AcOH/H_2O$ (1:1), was added KNCO (22 mg, 0.27 mmol). The mixture was reflex for 15 min. EtOAc (2 mL) was added. The organic phase was basified with 1N NaOH solution, dried over $Na_2SO_4$ and concentrated. The desired product was obtained as a colorless oil (60 mg, 84% yield). MS: (ESI), M/Z, 520 (M+1). Retention time: 2.18 min (FA-polar).

EXAMPLE 17

(5-Chloro-2-{3-[4-(4-chloro-benzoyl)-piperazin-1-yl]-4-hydroxy-pyrrolidin-1-yl}-phenyl)-urea

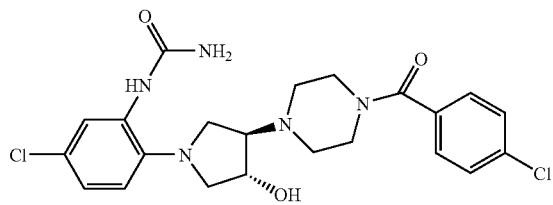

To a solution of acetic acid 4-[4-(4-chloro-benzoyl)-piperazin-1-yl]-1-(4-chloro-2-ureido-phenyl)-pyrrolidin-3-yl ester (60 mg, 0.11 mmol) in MeOH (2 mL), was added $K_2CO_3$ (30 mg). The mixture was stirred for 2 h. After concentrating, the residue was purified by column chromatography (ethyl acetate:MeOH:$Et_3N$: 10:1:0.1)) to give the desired product (20 mg, 50% yield) as a yellow oil. MS (ESI), M/Z, 478(M+1). Retention time: 1.68 min (FA-polar).

EXAMPLE 18

4-[4-(4-Chloro-benzyl)-piperazin-1-yl]-1-(4-chloro-2-nitro-phenyl)-pyrrolidin-3-ol

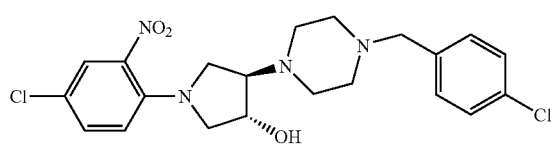

Following general procedures described above, the title compound was obtained as a yellow solid (95% yield), by using 4-chloro-2-fluoro-1-nitro-benzene as the starting material. MS: (ESI), M/Z, 451 (M+1). Retention time: 1.80 min (FA-polar).

EXAMPLE 19

Acetic acid 1-(2-amino-4-chloro-phenyl)-4-[4-(4-chloro-benzyl)-piperazin-1-yl]-pyrrolidin-3-yl ester Step 1: Acetic acid 4-[4-(4-chloro-benzyl)-piperazin-1-yl]-1-(4-chloro-2-nitro-phenyl)-pyrrolidin-3-yl ester

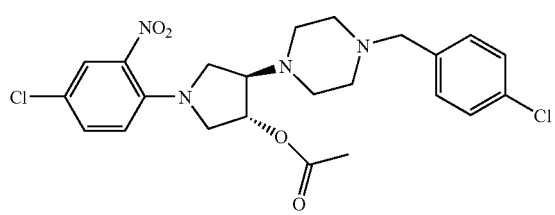

In a manner analogous to Step 1 of Example 16, except using 4-[4-(4-chloro-benzyl)-piperazin-1-yl]-1-(4-chloro-2-nitro-phenyl)-pyrrolidin-3-ol as the starting material, the title compound was obtain as a yellow oil (72% yield). MS: (ESI), M/Z, 493(M+1). Retention time: 2.17 min (FA-polar).

Step 2: Acetic acid 1-(2-amino-4-chloro-phenyl)-4-[4-(4-chloro-benzyl)-piperazin-1-yl]-pyrrolidin-3-yl ester

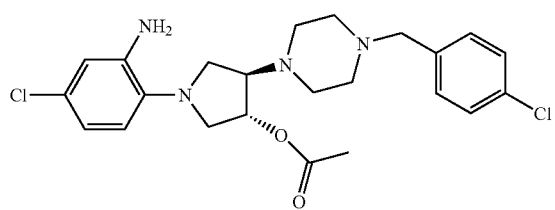

In a manner analogous to Step 2 of Example 16, except using acetic acid 4-[4-(4-chloro-benzyl)-piperazin-1-yl]-1-

(4-chloro-2-nitro-phenyl)-pyrrolidin-3-yl ester as starting material, the title compound was obtained as a white solid in 74% yield. MS: (ESI), M/Z, 463(M+1). Retention time: 1.92 min (FA-polar).

Step 3: Acetic acid 4-[4-(4-chloro-benzyl)-piperazin-1-yl]-1-(4-chloro-2-ureido-phenyl)-pyrrolidin-3-yl ester

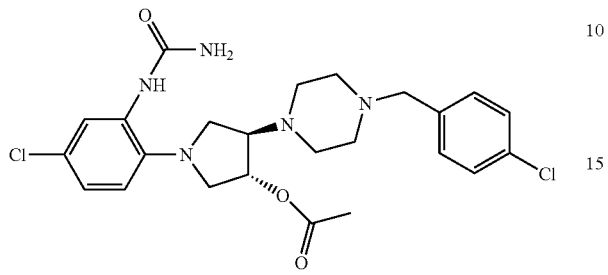

In a manner analogous to Step 3 of Example 16, except using acetic acid 1-(2-amino-4-chloro-phenyl)-4-[4-(4-chloro-benzyl)-piperazin-1-yl]-pyrrolidin-3-yl ester as starting material, the title compound was obtained as a colorless oil in 28% yield. MS: (ESI), M/Z, 506(M+1). Retention time: 1.77 min (FA-polar).

EXAMPLE 20

(5-Chloro-2-{3-[4-(4-chloro-benzyl)-piperazin-1-yl]-4-hydroxy-pyrrolidin-1-yl}-phenyl)-urea

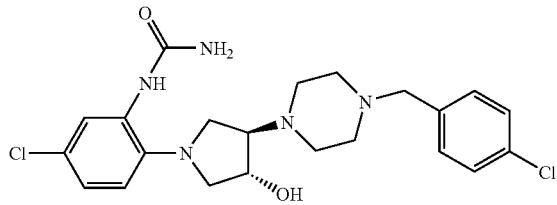

Following general procedures above using acetic acid 4-[4-(4-chloro-benzyl)-piperazin-1-yl]-1-(4-chloro-2-ureido-phenyl)-pyrrolidin-3-yl ester as starting material, the title compound was obtained as a white solid in 50% yield. MS: (ESI), M/Z, 464(M+1). Retention time: 1.62 min (FA-polar).

As depicted in the general schemes I and 2, and as described in the procedures above, coupling of the pyrrolidinyl intermediate with a suitable aryl or heteroaryl halide yields compounds of the invention. A variety of aryl and heteroaryl halides are commercially available (for example, 4,7-dichloroquinoline, 2-chloro-4-(trifluoromethyl)pyrimidine, 1-bromo-4-chlorobenzene, 3-bromopyridine, 5-bromo-2-chloropyrimidine, methyl-2-chloro-4-(trifluoromethyl)pyrimidine-5-carboxylate, 4-chloro-7-(trifluoromethyl)quinoline, 4-chloro-8-(trifluoromethyl)quinoline, 1-bromo-3-(trifluoromethyl)benzene, 2-chloro-1H-benzo[d]imidazole, 2-chloro-5-fluoropyrimidin-4-amine, 2-chloropyrimidine, 1-chloroisoquinoline, 2,3,5-trichloropyridine, 4,7-dichloroquinazoline, 2,3-dichloro-5-(trifluoromethyl)pyridine, ethyl-2-chloronicotinate, 4-chloro-2,8-bis(trifluoromethyl)quinoline, 4-chloro-6,7-dimethoxyquinazoline, 2,4-dichloropyrimidine, 1,6-dichloroisoquinoline, 2-chloro-4-methoxypyrimidine, 2,5-dichloropyridine, 2-chloro-4-methyl-6-phenylpyrimidine, 6-chloro-9H-purin-2-amine, and 4-chloro-6-phenylpyrimidine, to name a few). Additionally, a variety of aryl and heteroaryl halides may be prepared according to methods known in the art. Examples 21-28 below describe the synthesis of certain exemplary heteroaryl halides for use in the preparation of compounds of the invention.

EXAMPLE 21

4-Chloro-6-(4-chloro-phenyl)-pyrimidine

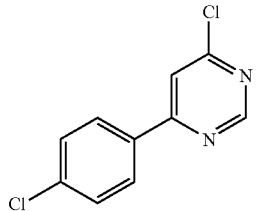

To a solution of 2,4-dichloro-pyrimidine (1 eq) in THF/H$_2$O (4:3) solution, was added 4-chloro phenyl boronic acid (1 eq), Pd(PPh$_3$)$_4$ (0.01 eq) and Na$_2$CO$_3$ (2 eq) under Ar. The reaction mixture was stirred at reflux for overnight. EtOAc (10 mL) was added. The organic phase was separated, dried over Na$_2$SO$_4$, and concentrated. The residue was purified by column chromatography (Ethyl acetate:Hexane:1:3) to give the desired product as a white powder (71% yield. MS: (ESI), MIZ, 225 (M+1). Retention time: 1.07 min (FA-non polar).

EXAMPLE 22

2-Chloro-4-(4-chloro-phenyl)-6-methyl-pyrimidine

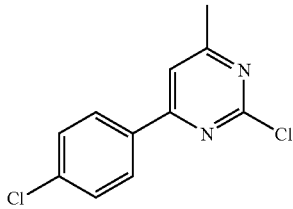

Following the general procedure described in Example 21, the title compound was obtained as a white powder (54% yield), by using 2,4-dichloro-6-methyl-pyrimidineand 4-chlorophenyl boronic acid as the starting material. MS: (ESI), M/Z, 239 (M+1). Retention time: 0.84 min (FA-non polar).

EXAMPLE 23

2-Chloro-4-(3-chloro-phenyl)-6-methyl-pyrimidine

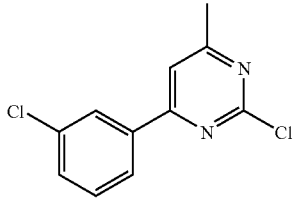

Following the general procedure described in Example 21, the title compound was obtained as a white powder (54% yield), by using 2,4-dichloro-6-methyl-pyrirnidineand 3-chlorophenyl boronic acid as the starting material. MS: (ESI), M/Z, 239 (M+1). Retention time: 0.92 min (FA-non polar).

EXAMPLE 24

(4-Chloro-phenyl)-(2-chloro-6-trifluoromethyl-pyrimidin-4-yl)-amine 2,4-Dichloro-6-trifluoromethyl-pyrimidine

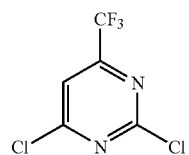

To 6-trifluoromethyl-pyrimidine-2,4-diol (460 mg, 2.55 mmol), was added POCl₃ (1.1 mL). The mixture was stirred at reflux for overnight. After cooling to RT, the mixture was quenched with ice and extracted with EtOAc (2×10 mL). The organic phase was dried over Na₂SO₄ and concentrated. The residue was purified by column chromatography (Ethyl acetate:Hexane: 1:1) to give the desired product as a brown oil (90 mg, 16% yield). This compound was not ionized in the LC-MS method. $^1$H NMR (CDCl₃) δ 7.62 (s, 1H).

(4-Chloro-phenyl)-(2-chloro-6-trifluoromethyl-pyrimidin-4-yl)-amine

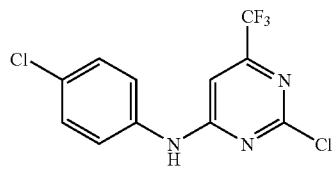

To a solution of 2,4-dichloro-6-trifluoromethyl-pyrimidine (90 mg, 0.41 mmol) in n-butanol (1 mL), was added 4-chlorophenylamine (52 mg, 0.416 mmol) and DIPEA (72 uL, 0.416). The mixture was stirred at 100° C. for overnight. The LC-MS showed the desired product mass [MS:(ESI), M/Z, 308 (M+1). Retention time: 2.70 min (FA-polar)]. This intermediate was used in situ without purification.

EXAMPLE 25

General procedure to synthesize 2-chloro-4-trifluoromethyl-6-alkyl pyrimidine

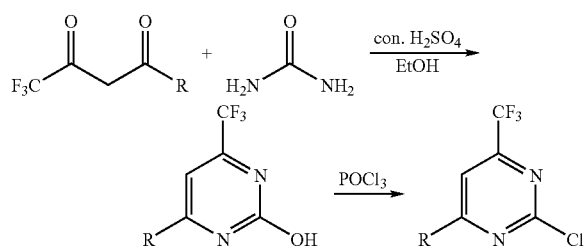

Step 1: Formation of 2-hydroxy-4-trifluoromethyl-6-alkyl pyrimide

To a solution of 2,4-diketone (15 mmol) in EtOH (50 mL), was added urea (15 mmol) and concentrated H₂SO₄ solution (0.5 mL). The mixture was stirred at reflux for overnight. After concentrating and neutralizing with Sat. NaHCO₃, the aqueous phase was extracted with EtOAc (3×20 mL). The organic phase was dried over MgSO₄ and concentrated. The pure product (2-hydroxy-chloro-4-trifluoromethyl-6-alkyl pyramiding) was obtained by titrating in toluene with Et₂O.

Step 2: Formation of 2-chloro-4-trifluoromethyl-6-alkyl pyrimidine

To 2-hydroxy-4-trifluoromethyl-6-alkyl pyrimide (1 eq), was added POCl₃ (5 eq). The mixture was stirred at reflux for overnight. After cooling to RT, the mixture was quenched with ice and neutralized with Sat. NaOH at 0° C. After extracting with EtOAc, the organic phase was dried over Na₂SO₄ and concentrated. The residue was purified by column chromatography (Ethyl acetate:Hexane: 1:4) to give the desired product.

EXAMPLE 26

2-Chloro-4-methyl-6-trifluoromethyl-pyrimidine

4-Methyl-6-trifluoromethyl-pyrimidin-2-ol

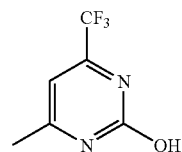

Following the procedure in Example 25, using 1,1,1-trifluoro-pentane-2,4-dione as the starting material, the title compound was obtained as an orange solid (20% yield). MS: (ESI), M/Z, 179(M+1), Retention time: 1.18 min (FA-polar).

2-Chloro-4-methyl-6-trifluoromethyl-pyrimidine

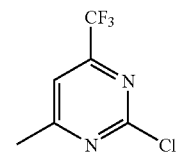

Following the procedure in Example 25, using 4-methyl-6-trifluoromethyl-pyrimidin-2-ol as the starting material, the title compound was obtained as a brown oil (37% yield). This compound was not ionized in the LC-MS method. $^1$H NMR (CDCl₃) δ 7.44 (s, 1H), 2.68 (s, 3H).

EXAMPLE 27

2-Chloro-4-methyl-6-trifluoromethyl-pyrimidine 4,6-Bis-trifluoromethyl-pyrimidin-2-ol

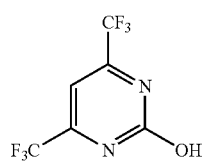

Following the procedure in Example 25, using 1,1,1,5,5,5-hexafluoro-pentane-2,4-dione as the starting material, the title compound was obtained as a white solid (20% yield). MS:(ESI), M/Z, 231(M−1), Retention time: 2.42 min (FA-polar).

Example 28

2-Chloro-4-methyl-6-trifluoromethyl-pyrimidine

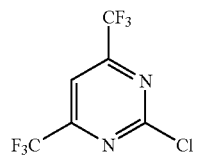

Following the procedure in Example 25, using 4,6-bis-trifluoromethyl-pyrimidin-2-ol as the starting material, the title compound was obtained as a volatile oil. Due to volatility, this intermediate was not charaterized. This compound was not ionized in the LC-MS.

Examples 29-34 below describe the synthesis of certain exemplary compounds of the invention where $Cy^1$ is a substituted heteroaryl group. It will be appreciated that compounds as described generally herein and as exemplified in Table 1 herein can also be prepared according to the methods described above and herein.

EXAMPLE 29

(4-Chloro-phenyl)-{4-[4-hydroxy-1-(6-methoxy-2-trifluoromethyl-quinazolin-4-yl)-pyrrolidin-3-yl]-piperazin-1-yl}-methanone Step 1:
6-methoxy-2-trifluoromethyl-3H-quinazolin-4-one

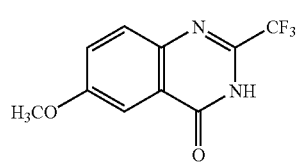

To 2.99 mmoles of 2-amino-5-methoxy anthranilic acid in 10 mL acetonitrile, add 14.9 mmoles of pyridine. The reaction mixture was cooled in ice and then 8.97 mmoles of trifluoroacetic anhydride was added to the reaction mixture and it was slowly warmed to room temperature and allowed to stir for 2 hours. This reaction mixture was added to an ice cooled suspension of 11.96 mmoles ammonium carbonate in 5 mL acetonitrile and it was allowed to warm to room temperature and stirred overnight. The reaction mixture was concentrated to a thick oil, 10 mL acetic acid was added to the residue and it was heated at 118-120° C. for 2.5-3 hours. The reaction mixture was concentrated and then a 1:1 soln of ethanol-water was added, the white solid obtained was filtered and washed with fresh cold ethanol-water and vaccum dried to yield the title compound in 74% yield. LC-MS: m/z=245 (M$^+$+1)

Step 2. Synthesis of
4-chloro-6-methoxy-2-trifluoromethyl-quinazoline

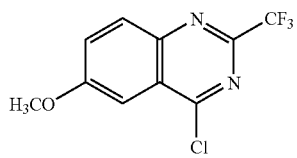

To 0.614 mmoles of 6-methoxy-2-methyl-3H-quinazolin-4-one in 0.4M soln of DCE, add 0.737 mmoles of PCl$_5$ and microwave at 150° C. for 4000 secs. For the workup, the reaction mixture was diluted with CH$_2$Cl$_2$ and washed with water and brine. The organic layer was separated and dried over MgSO$_4$, filtered and excess solvent was removed on under pressure to yield the title compound in 70% yield. The compound was used for the next step without further purification. LC-MS: m/z=263 (M$^+$+1)

Step 3. (4-Chloro-phenyl)-{4-[(3S,4S)-4-hydroxy-1-(6-methoxy-2-trifluoromethyl-quinazolin-4-yl)-pyrrolidin-3-yl]-piperazin-1-yl}-methanone

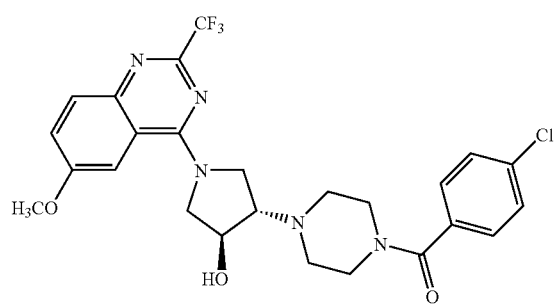

To 0.326 mmoles of (4-Chloro-phenyl)-[4-(4-hydroxy-pyrrolidin-3-yl)-piperazin-1-yl]-methanone (synthesis described above in Example 5), add 1.6 mL acetonitrile and 1.63 mmoles of DBU. The stirred solution was cooled in ice and then 0.358 mmoles of 4-chloro-6-methoxy-2-trifluoromethyl-quinazoline was added and the reaction mixture was allowed to stir for a period of 2.5 hours. For the workup, the reaction mixture was diluted with methanol and concentrated on the rotavap. To the concentrate about 35 mL of water was added and was extracted with 40 mL EtOAc. The organic layer was separated and washed with 35 mL of 1M aq K$_2$CO$_3$ soln, and brine, dried over MgSO₄ and excess solvent was removed on rotavap to yield a crude oil. This was diluted with about 2 mL EtOAc and about 8 mL ether was added and the white solid obtained was filtered off and vaccum dried to give the title compound in 80% yield. LC-MS: m/z=536 (M⁺+1)

EXAMPLE 30

(4-Chloro-phenyl)-{4-[(3S,4S)-4-hydroxy-1-(6-methoxy-quinazolin-4-yl)-pyrrolidin-3-yl]-piperazin-1-yl}-methanone Step 1. 6-Methoxy-3H-quinazolin-4-one To 1.025 mmoles of 2-amino-5-methoxy anthranilic acid add 6.14 mmoles of formamide and microwave reaction mixture for 20 mins at 160° C. After cooling the solid was diluted with 10 mL ethanol, the mixture was heated to reflux and allowed to cool slowly. The solid obtained was filtered and washed with cold ethanol and vaccum dried to give the title compound in 50% yield.
LC-MS: m/z=177 (M⁺+1)

Step 2. Synthesis of 4-chloro-6-methoxy-quinazoline

To 0.852 mmoles of 6-methoxy-3H-quinazolin-4-one in 0.4M soln of DCE, add 1.022 mmoles of PCl₅. Microwave at 150° C. for 4000 secs. Work-up: The reaction mixture was diluted with CH₂Cl₂ and washed with water and brine. The organic layer was separated dried over MgSO₄, filtered and excess solvent was removed on rotavap to yield the title compound in 75% yield. The compound was used for the next step without further purification. LC-MS: m/z=195 (M⁺+1)

Step 3. (4-Chloro-phenyl)-{4-[(3S,4S)-4-hydroxy-1-(6-methoxy-quinazolin-4-yl)-pyrrolidin-3-yl]-piperazin-1-yl}-methanone

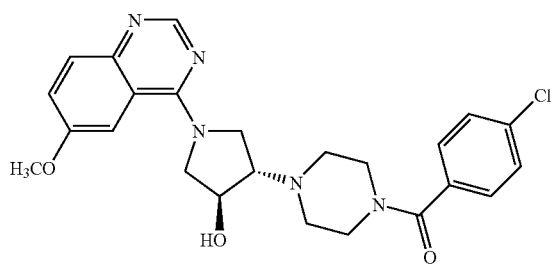

To 0.326 mmoles of (4-Chloro-phenyl)-[4-(4-hydroxy-pyrrolidin-3-yl)-piperazin-1-yl]-methanone (synthesis described above in Example 5), add 1.6 mL acetonitrile and 1.6 mmoles of DBU. The stirred solution was cooled in ice and then 0.358 mmoles of 4-chloro-6-methoxy-quinazoline was added and the reaction mixture was allowed to stir for a period of 2.5 hours. To 0.326 mmoles of (4-Chloro-phenyl)-[4-(4-hydroxy-pyrrolidin-3-yl)-piperazin-1-yl]-methanone, add 1.6 mL acetonitrile and 1.63 mmoles of DBU. The stirred solution was cooled in ice and then 0.358 mmoles of 4-chloro-6-methoxy-2-methyl-quinazoline (from Step 2 above) was added and the reaction mixture was allowed to stir for a period of 2.5 hours. For the reaction workup, the reaction mixture was diluted with methanol and concentrated on the rotavap. To the concentrate about 30 mL of water was added and was extracted with 40 mL EtOAc. The organic layer was separated and washed with 30 mL of 1M aq K₂CO₃ solution, and brine, dried over MgSO₄ and excess solvent was removed on rotavap to yield a crude oil. This was diluted with about 2 mL EtOAc and about 8 mL ether was added and the white solid obtained was filtered off and vaccum dried to give the title compound in 50% yield. LC-MS: m/z=468 (M⁺+1).

EXAMPLE 31

2-{3-[4-(4-Chloro-benzoyl)-piperazin-1-yl]-4-hydroxy-pyrrolidin-1-yl}-4-trifluoromethyl-pyrimidine-5-carboxylic acid

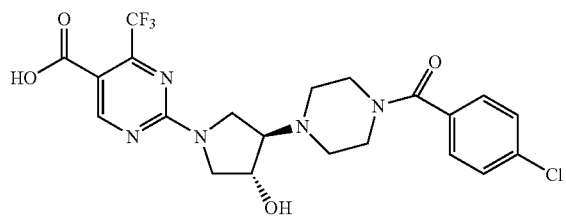

To a solution of 2-{3-[4-(4-Chloro-benzoyl)-piperazin-1-yl]-4-hydroxy-pyrrolidin-1-yl}-4-trifluoromethyl-pyrimidine-5-carboxylic ester in THF (1 mL), was added 1N LiOH solution (1 eq). The mixture was stirred at reflux for 5 h. The reaction mixture was acidified with 1 N HCl solution to PH=7 and concentrated to dryness. The obtained crude product was used in next step without purification. (100% yield). MS: (ESI), M/Z, 500 (M+1). Retention time: 1.77 min (FA-polar).

EXAMPLE 32

2-{3-[4-(4-Chloro-benzoyl)-piperazin-1-yl]-4-hydroxy-pyrrolidin-1-yl}-4-trifluoromethyl-pyrimidine-5-carboxylic acid amide

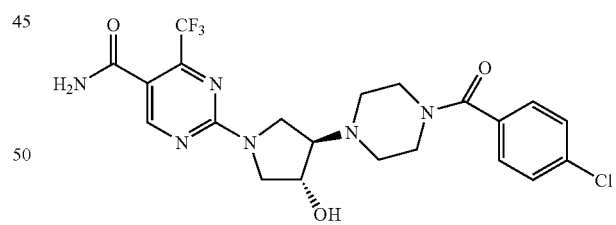

To a solution of 2-{3-[4-(4-Chloro-benzoyl)-piperazin-1-yl]-4-hydroxy-pyrrolidin-1-yl}-4-trifluoromethyl-pyrimidine-5-carboxylic acid (1 eq) in DMF (1 mL), was added HATU (1.5 eq), DIPEA (4 eq) and HOBt (1.5 eq). The mixture was stirred at RT for 5 min. Then NH₄Cl (2 eq) was added. The final reaction mixture was stirred at RT for overnight. EtOAc (2 mL) was added. The organic layer was washed with H₂O (2×1 mL), dried over Na₂SO₄, and concentrated. The residue was purified by column chromatography (Ethyl acetate) to give the desired product as a white solid (35% yield). MS: (ESI), M/Z, 499 (M+1). Retention time: 1.56 min (FA-polar).

EXAMPLE 33

2-{3-[4-(4-Chloro-benzyl)-piperazin-1-yl]-4-hydroxy-pyrrolidin-1-yl}-4-trifluoromethyl-pyrimidine-5-carboxylic acid

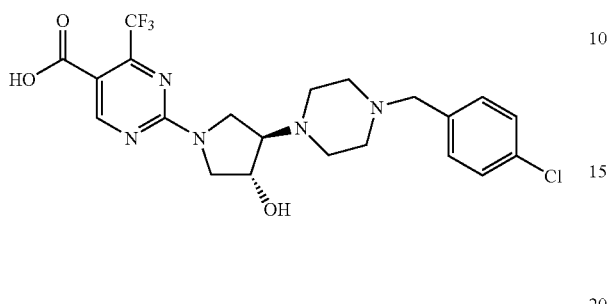

Following the procedure for hydrolysis in Example 31, the title compound was obtained as a white solid (100% yield). MS: (ESI), M/Z, 486 (M+1). Retention time: 1.57 min (FA-polar).

EXAMPLE 34

2-{3-[4-(4-Chloro-benzyl)-piperazin-1-yl]-4-hydroxy-pyrrolidin-1-yl}-4-trifluoromethyl-pyrimidine-5-carboxylic acid amide Following the procedure for primary amide formation in Example 32, the title compound was obtained as a white solid (30% yield). MS: (ESI), M/Z, 485 (M+1). Retention time: 1.46 min (FA-polar).

Syntheses of heteroaryl halides (not commercially available) used for preparation of compounds in the invention are shown in Schemes 3, 4, 5, 6, 7 and 8.

Scheme 3

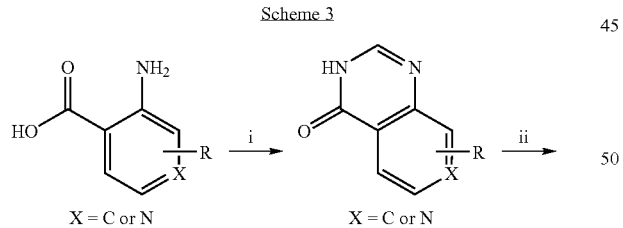

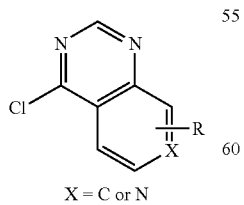

Reagents and conditions: (i) HCONH$_2$, 150° C., 20 min. microwave. (ii) PCl$_5$, dichloroethane, 150° C., 20-40 min. microwave.

Scheme 4

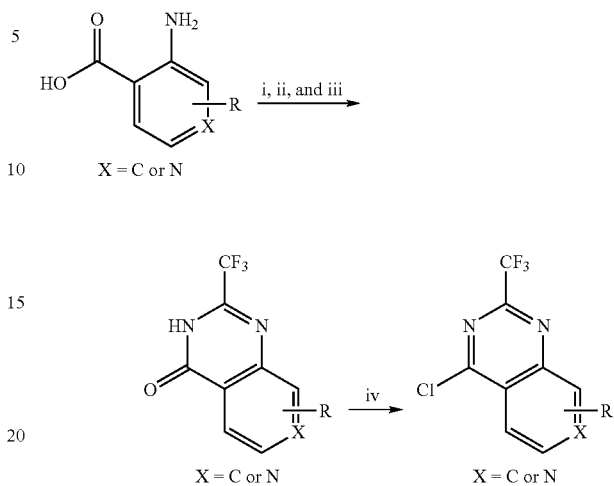

Reagents and conditions: (i) (CF$_3$CO)$_2$O, Pyridine/CH$_3$CN, 0° C.-r.t., 2 h. (no work-up) (ii) (NH$_4$)$_2$CO$_3$, 0° C.-r.t., 16-18 h; (no work-up, evaporate solvent) (iii) CH$_3$CO$_2$H, 120° C. 3 h. (iv) PCl$_5$, dichloroethane, 150° C., 20-40 min. microwave.

Scheme 5

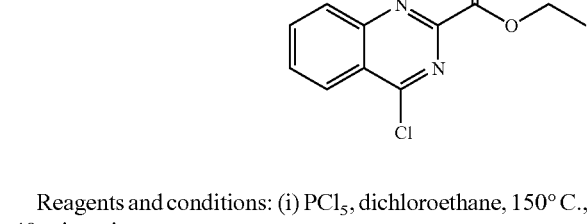
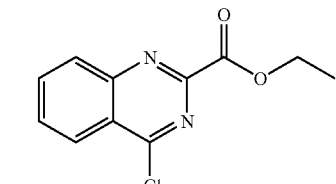

Reagents and conditions: (i) PCl$_5$, dichloroethane, 150° C., 40 min. microwave.

Scheme 6

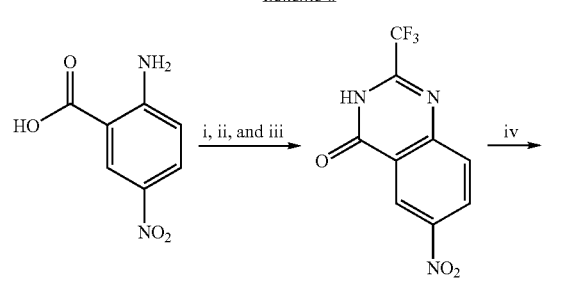

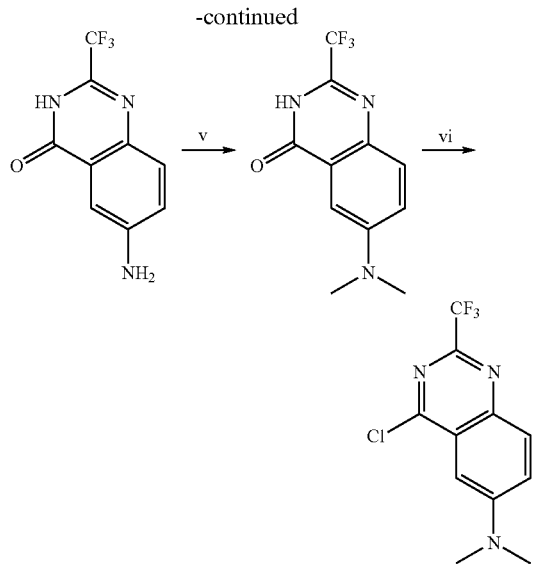

Reagents and conditions: (i) (CF₃CO)₂O, Pyridine/CH₃CN, 0° C.-r.t., 2 h. (no work-up) (ii) (NH₄)₂CO₃, 0° C.-r.t., 16-18 h; (no work-up, evaporate solvent) (iii) CH₃CO₂H, 120° C. 3 h. (iv) H₂, Pd—C, MeOH, r.t, 18 h. (v) aqueous HCHO, H₂, Pd—C, r.t., 48 h (vi) PCl₅, dichloroethane, 160° C., 20 min. microwave.

Scheme 7

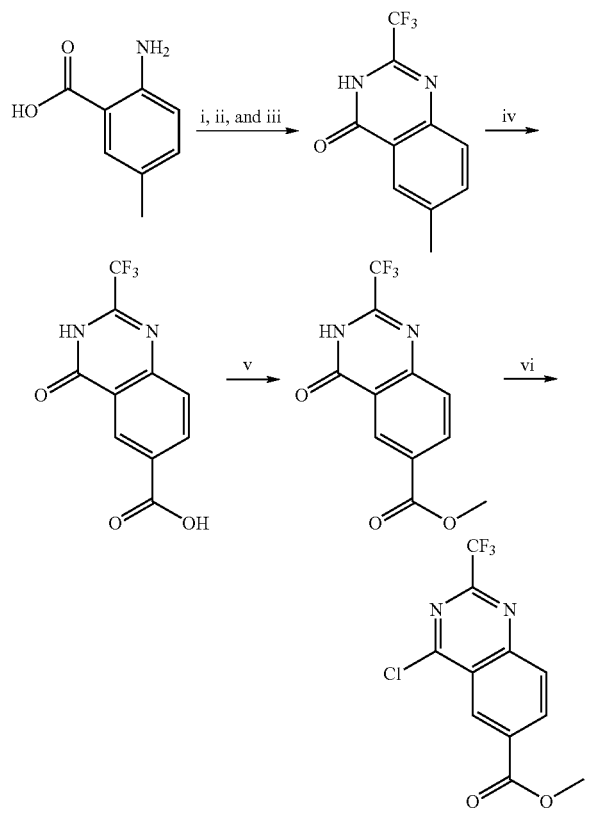

Reagents and conditions: (i) (CF₃CO)₂O, Pyridine/CH₃CN, 0° C.-r.t., 2 h. (no work-up) (ii) (NH₄)₂CO₃, 0° C.-r.t., 16-18 h; (no work-up, evaporate solvent) (iii) CH₃CO₂H, 120° C. 3 h. (iv) KMnO₄, H₂O, t-BuOH, 100° C., 3 h. (v) H₂SO₄, MeOH, 50° C., 16 h. (vi) PCl₅, dichloroethane, 160° C., 20 min. microwave.

Scheme 8

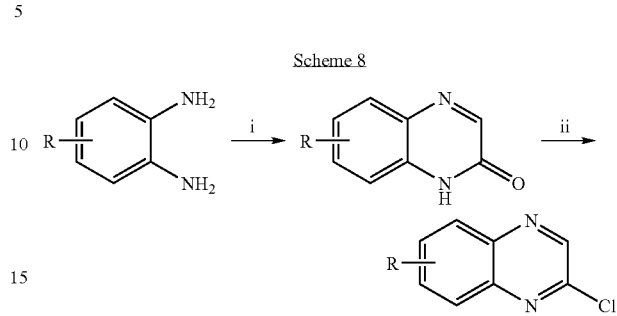

Reagents and conditions: (i) CHOCH₂CO₂H, EtOH, reflux 3 h; (ii) PCl₅, dichloroethane, 150° C., 20-40 min. microwave.

Example 35 below describes the synthesis of certain exemplary intermediates and compounds where Ring A is disubstituted.

EXAMPLE 35

(4-Chloro-phenyl)-{4-[1-(7-chloro-quinazolin-4-yl)-4-hydroxy-4-methyl-pyrrolidin-3-yl]-piperazin-1-yl}-methanone Step 1:

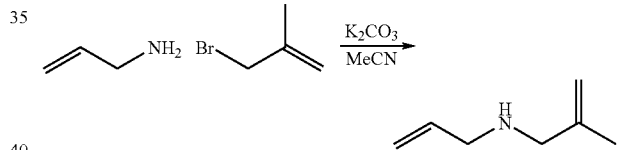

To a cold solution of allylamine (3.0 mL, 40 mmol) in 100 mL MeCN was added 3-bromo-2-methyl-propene (4.1 mL, 40 mmol) and then K₂CO₃ (8.3 g, 60 mmol). After 5 mins, the mixture was warmed up to rt and stirred overnight. The mixture was partitioned in ether and water. The organic phase was washed with NaHCO₃, brine, dried over Na₂SO₄ and concentrated down to give 2.0 g desired product.

Step 2:

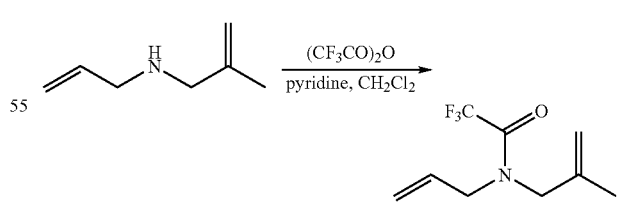

To a cold solution (3-5° C.) of allyl-(2-methyl-allyl)-amine (888 mg, 8 mmol) and pyridine (0.775 mL, 9.6 mmol) in 20 mL of DCM was added TFA anhydride (1.25 mL, 8.8 mmol). After 10 min., the mixture was warmed up to rt and stirred for 4 hrs. The mixture was diluted with ether and washed with 1N HCl (twice), water, saturated NaHCO₃. The organic phase was dried over MgSO₄ and concentrated to give 1 g of desired product. ¹H-NMR (300 MHz, CDCl₃) δ 1.75.(m3H), 4.02 (m, 4H), 4.86 (m, 1H), 5.03 (m, 1H), 5.3 (m, 2H), 5.79 (m, 1H).

Step 3:

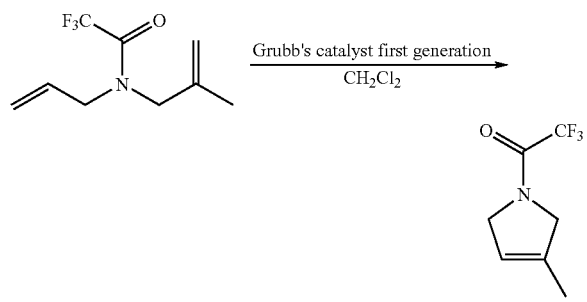

N-Allyl-2,2,2-trifluoro-N-(2-methyl-allyl)-acetamide (697 mg, 3.37 mmol) and Grubb's catalyst (138 mg, 0.17 mmol) were added together in CH₂Cl₂ (6.5 mL). The reaction mixture was reflux for 3 hrs and then stirred at rt overnight. The solvent was evaporated, and the resulting crude residue was purified by column chromatography on silica (hexane: ethyl Acetate 0% to 15%) to give 507 mg of desired product. ¹H-NMR (300 MHz, CDCl3): mixture of rotamers δ 1.85.m.3H), 4.37 (m, 4H), 5.50 (m, 1H)

Step 4:

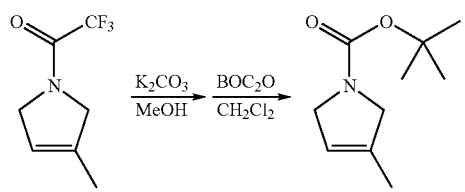

K₂CO₃ (92 mg, 0.66 mmol) was added to a methanol (3 ml) solution of 2,2,2-Trifluoro-1-(3-methyl-2,5-dihydro-pyrrol-1-yl)-ethanone and stirred at rt overnight. BOC₂O (160 mg, 0.75 mmol) in 1 mL of CH₂Cl₂ was added. The reaction mixture was stirred at rt for 1 hour and concentrated down. The residue was partitioned in ether and water. The organic phase was washed with brine, dried over Na₂SO₄ and concentrated down to give 70 mg of the desired product in 64% yield. ¹H-NMR (300 MHz, CDCl₃): mixture of rotamers δ 1.52 (m, 9H), 1.79 (bs.3H), 4.07 (m, 4H), 5.41 (m, 1H)

Step 5:

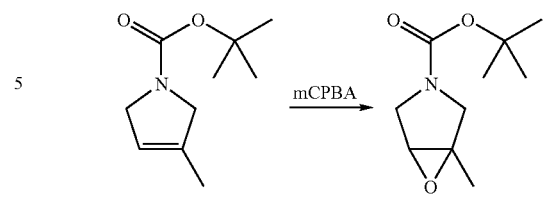

The desired compound was prepared in 91% yield according to the general epoxidation procedure described in Example 1, starting from 3-Methyl-2,5-dihydro-pyrrole-1-carboxylic acid tert-butyl ester. ¹H-NMR (300 MHz, CDCl₃): mixture of rotamers δ 1.49 (m, 9H), 1.56 (m, 3H), 3.27 (m, 1H), 3.38 (m, 1H), 3.49 (m, 1H), 3.75 (m, 2H).

Step 6:

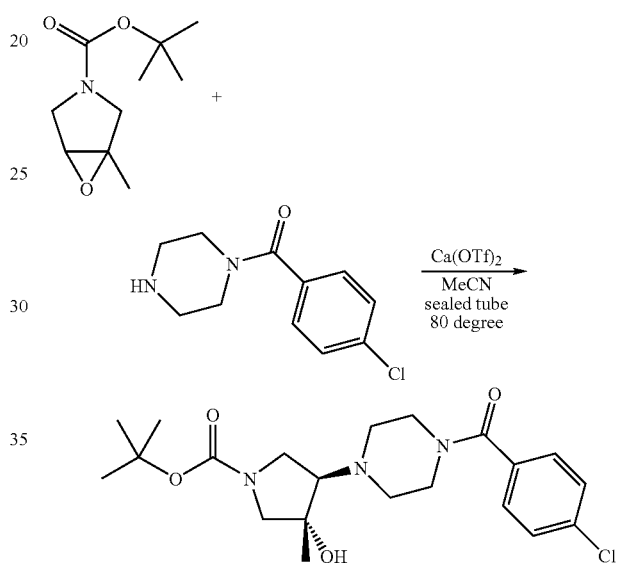

The desired compound was prepared according to Method B (as shown in Schemes I and II and as described generally above) from 1-Methyl-6-oxa-3-aza-bicyclo[3.1.0]hexane-3-carboxylic acid tert-butyl ester and (4-Chloro-phenyl)-piperazin-1-yl-methanone in 33% yield. Retention time (LC method: ammonium acetate standard): 1.60 min. MS (M+H⁺): 424.3

Step 7:

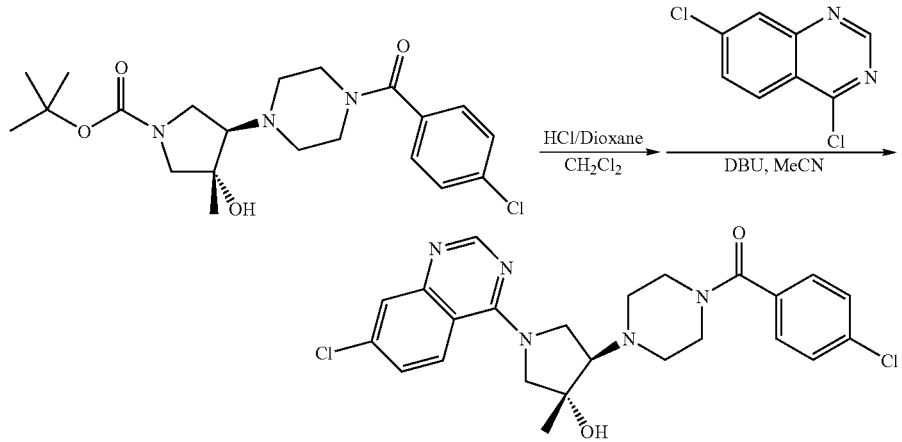

The desired compound (4-Chloro-phenyl)-{4-[1-(7-chloro-quinazolin-4-yl)-4-hydroxy-4-methyl-pyrrolidin-3-yl]-piperazin-1-yl}-methanone was prepared as shown above according to general methods for Boc deprotection described above, then Procedure E. Retention time (LC method: ammonium acetate standard): 1.56 min. MS (M+H$^+$): 486.4

Examples 36-38 below describe the synthesis of exemplary intermediates and compounds where Ring B is further substituted at the site of attachment of the chlorophenyl ring.

EXAMPLE 36

Trans-4-(4-chloro-phenyl)-1-(4-hydroxy-pyrrolidin-3-yl)-piperidin-4-ol hydrochloride

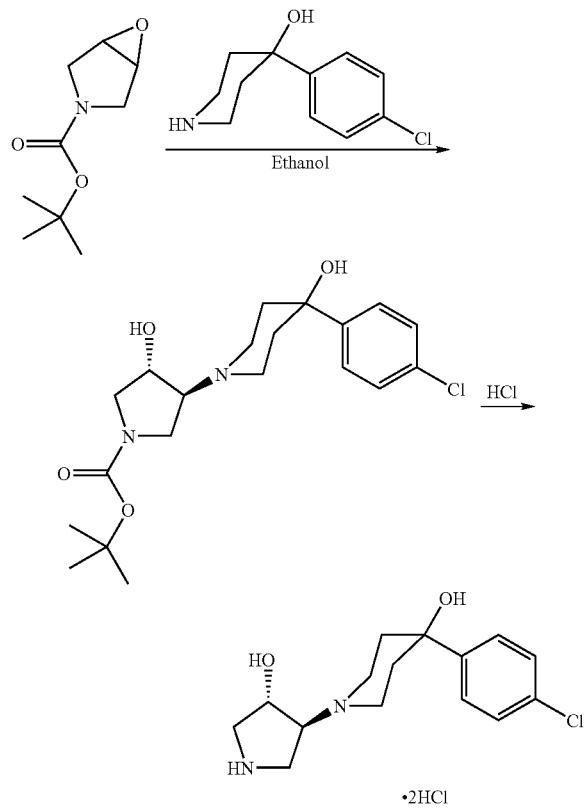

The title compound was prepared following general procedures described above. LC, AA standard method, retention time: 1.00 minutes. MS (M+H$^+$): 297.

EXAMPLE 37

4-(4-Chloro-phenyl)-1-[4-hydroxy-1-(4-methyl-6-trifluoromethyl-pyrimidin-2-yl)-pyrrolidin-3-yl]-piperidin-4-ol

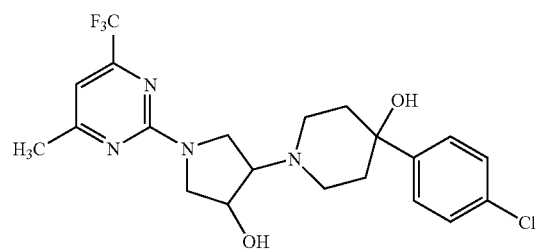

The title compound was prepared following general procedures described above from trans-4-(4-chloro-phenyl)-1-(4-hydroxy-pyrrolidin-3-yl)-piperidin-4-ol hydrochloride and 4-chloro-5-methyl-2-trifluoromethyl-pyrimidine in the presence of diisopropylethylamine and DMF. $^1$H-NMR (300 MHz, DMSO): δ 1.58 (2 H, m), 1.89 (2 H, m), 2.40 (3 H, s), 2.60 (3 H, m), 2.95 (2 H, m), 3.44 (1 H, m), 3.80 (2 H, m), 4.32 (1 H, m), 4.90 (1 H, s), 5.20 (1 H, d), 6.92 (1 H, s), 7.42 (4 H, dd). Retention Time (LC, method, AA standard): 1.75 min. MS (M+H$^+$): 457

EXAMPLE 37

4-(4-Chloro-phenyl)-1-[(3S,4S)-1-(7-chloro-quinazolin-4-yl)-4-hydroxy-pyrrolidin-3-yl]-piperidin-4-ol

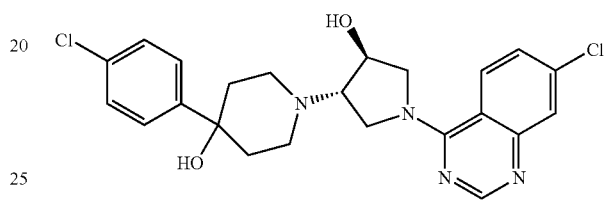

The title compound was prepared following general procedures described above from 4-(4-Chlorophenyl)-1-(4-hydroxy-pyrrolidin-3-yl)-piperidin-4-ol and 4,7-dichloro-quinazoline. $^1$H-NMR (300 MHz, DMSO): δ1.57 (2 H, m), 1.90 (2 H, m), 2.60-2.70 (3 H, m), 2.96 (2 H, m), 3.70 (1 H, m), 3.85 (1 H, m), 4.10 (2 H, m), 4.36 (1 H, m), 4.90 (1 H, s), 5.32 (1 H, d), 7.40 (4 H, dd), 7.48 (1 H, m), 7.73 (1 H, d), 8.30 (1 H, d), 8.45 (1 H, s). Retention Time (LC, method, AA standard): 1.48 min. MS (M+H$^+$): 459.

EXAMPLE 38

4-(4-Chloro-phenyl)-1-[1-(5,6-dimethyl-2-trifluoromethyl-pyrimidin-4-yl)-4-hydroxy-pyrrolidin-3-yl]-piperidin-4-ol

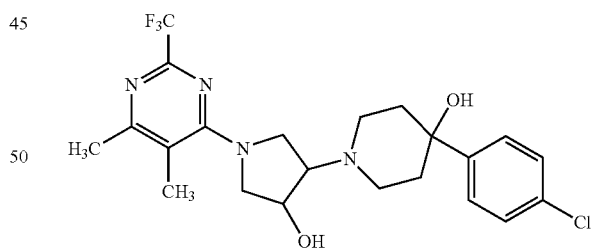

The title compound was prepared following general procedures described above from trans-4-(4-chloro-phenyl)-1-(4-hydroxy-pyrrolidin-3-yl)-piperidin-4-ol hydrochloride and 4-chloro-5,6-dimethyl-2-trifluoromethyl-pyrimidine in the presence of diisopropylethylamine and DMF. $^1$H-NMR (300 MHz, DMSO): δ 1.58 (2 H, m), 1.89 (2 H, m), 2.40 (3 H, s), 2.60 (3 H, m), 2.95 (2 H, m), 3.32 (1 H, m), 3.44 (1 H, m), 3.80 (2 H, m), 4.32 (1 H, m), 4.90 (1 H, s), 5.20 (1 H, d), 6.92 (1 H, s), 7.42 (4 H, dd). Retention Time (LC, method, AA standard): 1.75 min. MS (M+H$^+$): 457

Additional compounds in the invention can be prepared as shown in Schemes 9,10, and 11.

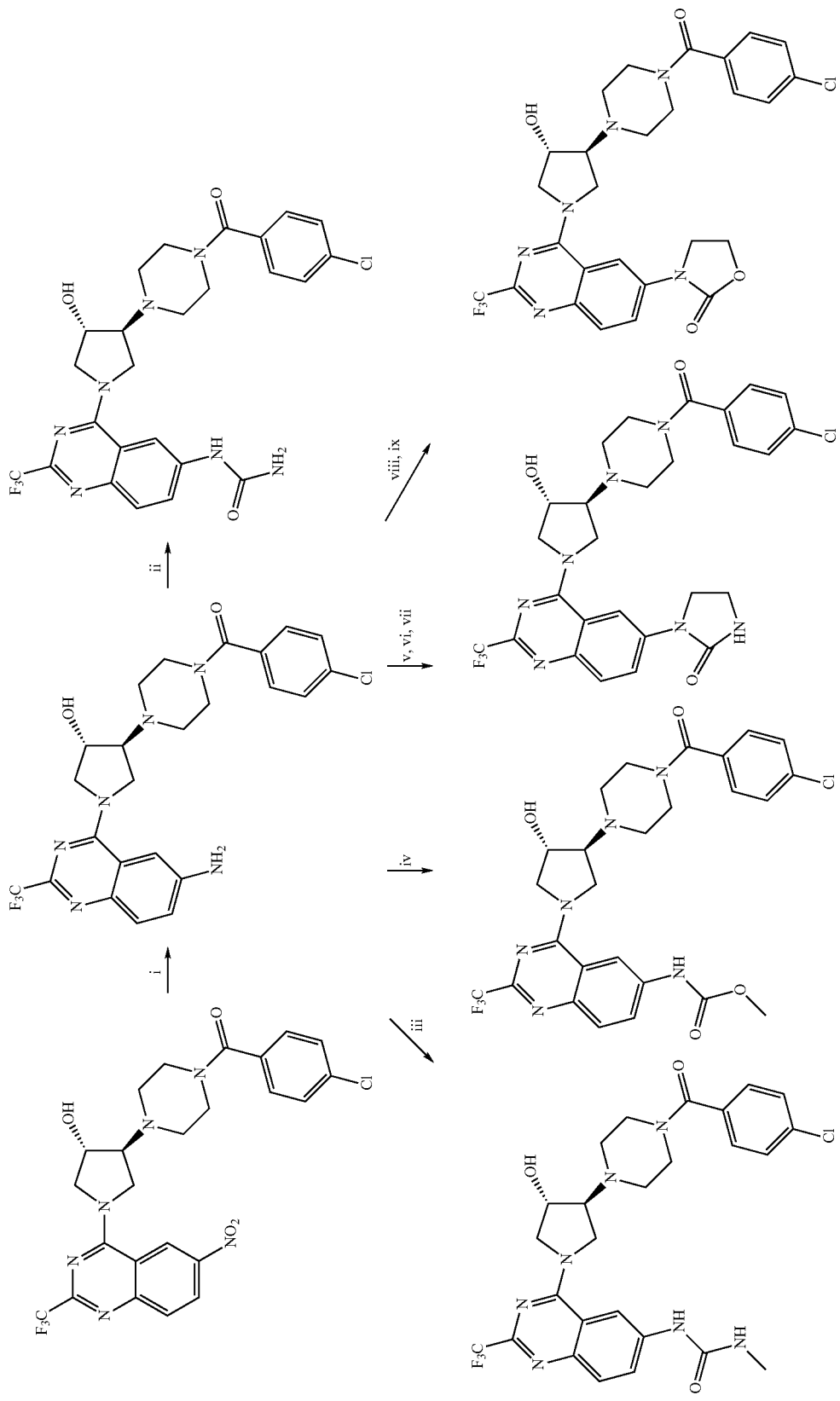

Reagents and conditions: (i) H$_2$, Pt—C, EtOH, r.t, 3 h; (ii) KNCO, CH$_3$CO$_2$H, H$_2$O, 40-42° C., 40 min. (iii) CH$_3$NCO, CH$_2$Cl$_2$, r.t., 16-18 h. (iv) CH$_3$OCOCl, Et$_3$N, CH$_2$Cl$_2$, r.t. 16-18 h (v) BocNHCH$_2$CHO, NaBH(OAc)$_3$, CH$_3$CO$_2$H, dichoroethane, r.t., 2 h (no purification) (vi) TFA, CH$_2$Cl$_2$, r.t., 1 h (vii) CDI, Et$_3$N, CH$_3$CN, r.t., 16 h (viii) BrCH$_2$CH$_2$OCOCl, CH$_2$Cl$_2$, r.t., 16-18 h. (no purification) (ix) DBU, CH$_3$CN, r.t., 3 h Scheme 10

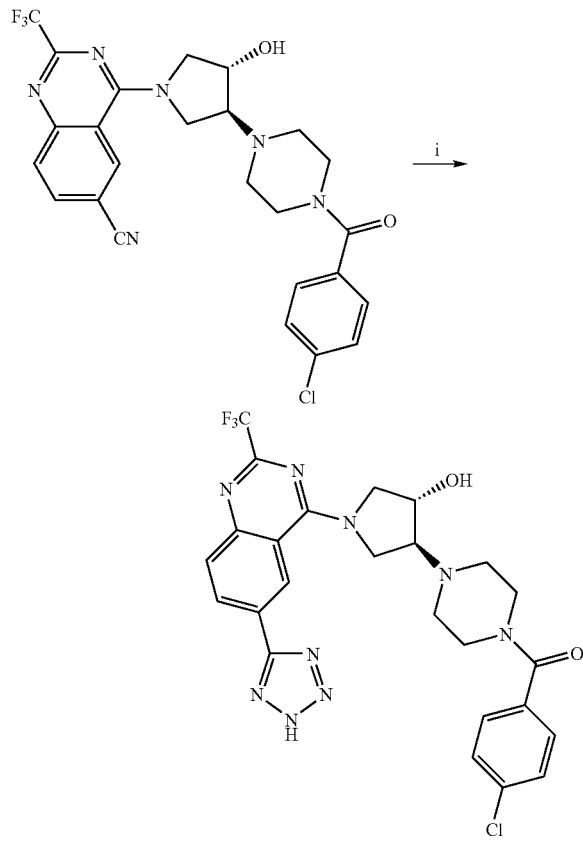

Reagents and conditions: (i) NaN$_3$, Et$_3$N, H$_2$SO$_4$, Toluene, 100° C., 16 h.

Scheme 11

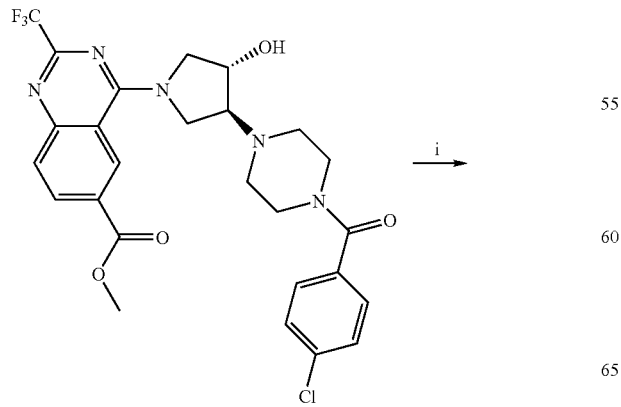

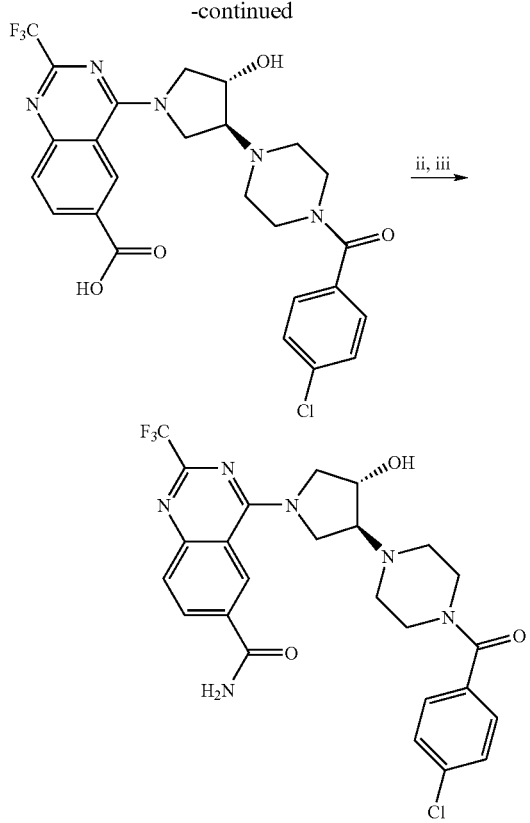

Reagents and conditions: (i) NaOH, MeOH, THF, H$_2$O, r.t, 2 h; (ii) CDI, CH$_3$CN, r.t., 30 min. (iii) conc. NH$_4$OH, r.t., 16 h.

In general, compounds of the invention can be prepared using the methods described above. Table 1 depicts certain exemplary compounds of the invention that can be prepared according to the methods described above, and Table 2 depicts characterization data for these exemplary compounds

| Compound Number (referring to Table 1) | m/z (M$^+$ + 1) |
| --- | --- |
| 1 | 471 |
| 2 | 457 |
| 3 | 456 |
| 4 | 442 |
| 5 | 420 |
| 6 | 406 |
| 7 | 387 |
| 8 | 466 |
| 9 | 452 |
| 10 | 514 |
| 11 | 500 |
| 12 | 505 |
| 13 | 505 |
| 14 | 499 |
| 15 | 485 |
| 16 | 454 |
| 17 | 426 |
| 18 | 421 |
| 19 | 388 |
| 20 | 374 |
| 21 | 437 |
| 22 | 455 |
| 23 | 472 |
| 24 | 472 |

-continued

| Compound Number (referring to Table 1) | m/z (M⁺ + 1) |
|---|---|
| 25 | 459 |
| 26 | 573 |
| 27 | 498 |
| 28 | 412 |
| 29 | 422 |
| 30 | 422 |
| 31 | 464 |
| 32 | 498 |
| 33 | 494 |
| 34 | 471 |
| 35 | 418 |
| 36 | 421 |
| 37 | 478 |
| 38 | 464 |
| 39 | 443 |
| 40 | 429 |
| 41 | 513 |
| 42 | 499 |
| 43 | 498 |
| 44 | 520 |
| 45 | 478 |
| 46 | 451 |
| 47 | 478 |
| 48 | 456 |
| 49 | 454 |
| 50 | 421 |
| 51 | 464 |
| 52 | 450 |
| 53 | 440 |
| 54 | 454 |
| 55 | 440 |
| 56 | 463 |
| 57 | 420 |
| 58 | 406 |
| 59 | 506 |
| 60 | 511 |
| 61 | 457 |
| 62 | 457 |
| 63 | 473 |
| 64 | 471 |
| 65 | 459 |
| 66 | 464 |
| 67 | 456 |
| 68 | 456 |
| 69 | 454 |
| 70 | 440 |
| 71 | 388 |
| 72 | 374 |
| 73 | 498 |
| 74 | 484 |
| 75 | 488 |
| 76 | 474 |
| 77 | 492 |
| 78 | 443 |
| 79 | 455 |
| 80 | 459 |
| 81 | 472 |
| 82 | 464 |
| 83 | 471 |
| 84 | 438 |
| 85 | 471 |
| 86 | 456 |
| 87 | 458 |
| 88 | 460 |
| 89 | 446 |
| 90 | 498 |
| 91 | 512 |
| 92 | 498 |
| 93 | 506 |
| 94 | 506 |
| 95 | 492 |
| 96 | 472 |
| 97 | 492 |
| 98 | 416 |
| 99 | 402 |
| 100 | 388 |

-continued

| Compound Number (referring to Table 1) | m/z (M⁺ + 1) |
|---|---|
| 101 | 514 |
| 102 | 474 |
| 103 | 442 |
| 104 | 472 |
| 105 | 472 |
| 106 | 581 |
| 107 | 470 |
| 108 | 456 |
| 109 | 524 |
| 110 | 510 |
| 111 | 574 |
| 112 | 486 |
| 113 | 522 |
| 114 | 508 |
| 115 | 442 |
| 116 | 510 |
| 117 | 482 |
| 118 | 438 |
| 119 | 456 |
| 120 | 470 |
| 121 | 484 |
| 122 | 470 |
| 123 | 498 |
| 124 | 484 |
| 125 | 452 |
| 126 | 437 |
| 127 | 451 |
| 128 | 491 |
| 129 | 512 |
| 130 | 498 |
| 131 | 506 |
| 132 | 506 |
| 133 | 472 |
| 134 | 507 |
| 135 | 470 |
| 136 | 456 |
| 137 | 507 |
| 138 | 452 |
| 139 | 438 |
| 140 | 458 |
| 141 | 458 |
| 142 | 528 |
| 143 | 514 |
| 144 | 510 |
| 145 | 496 |
| 146 | 470 |
| 147 | 469 |
| 148 | 506 |
| 149 | 470 |
| 150 | 470 |
| 151 | 472 |
| 152 | 472 |
| 153 | 458 |
| 154 | 523 |
| 155 | 509 |
| 156 | 484 |
| 157 | 484 |
| 158 | 472 |
| 159 | 474 |
| 160 | 550 |
| 161 | 490 |
| 162 | 473 |
| 163 | 452 |
| 164 | 427 |
| 165 | 536 |
| 166 | 472 |
| 167 | 468 |
| 168 | 457 |
| 169 | 471 |
| 170 | 459 |
| 171 | 524 |
| 172 | 524 |
| 173 | 540 |
| 174 | 520 |
| 175 | 456 |
| 176 | 540 |

-continued

| Compound Number (referring to Table 1) | m/z (M+ + 1) |
|---|---|
| 177 | 536 |
| 178 | 524 |
| 179 | 542 |
| 180 | 564 |
| 181 | 550 |
| 182 | 439 |
| 183 | 537 |
| 184 | 550 |
| 185 | 550 |
| 186 | 521 |
| 187 | 549 |
| 188 | 551 |
| 189 | 549 |
| 190 | 579 |
| 191 | 524 |
| 192 | 564 |
| 193 | 549 |
| 194 | 564 |
| 195 | 579 |
| 196 | 578 |
| 197 | 456 |
| 198 | 563 |
| 199 | 564 |
| 200 | 537 |
| 201 | 540 |
| 202 | 590 |
| 203 | 531 |
| 204 | 574 |
| 205 | 591 |

Biological Testing

THP-1 FLIPR Assay

The primary screening assay is a FLIPR® (Fluorometric Imaging Plate Reader, available from Molecular Devices Corporation, Sunnyvale, Calif.) assay using THP-1 cells (ATCC, Catalog No. TIB 202), a monocytic derived cell line that endogenously expresses CCR1.

The cells were resuspended at $1 \times 10^6$ cells/ml in dye loading media (growth media (RPMI+10% FBS (Fetal Bovine serum)+$5.5 \times 10^{-5}$M 2-mercaptoethanol)+10 mM HEPES (N-2-hydroxyethylpiperazine-N'-2-ethane-sulfonic acid)+ 2.5 mM probenecid+fluo-3 (1:250)). The cells were incubated for 1 hour at 37° C. and then washed in FLIPR wash buffer (100 mL 10× HBSS (Hanks Buffered Saline Solution) (w/Ca++/Mg++)+20 mL 1M HEPES+1 g BSA+10 mL 250 mM probenecid+water (to make 1 L)) and plated at 50,000 cells/well in black/clear 384 well plates. The plates were transferred to FLIPR where the ability of different concentrations of compounds to inhibit RANTES induced calcium flux was assessed. Inhibition of the CCR1 response was reflected by a decrease of the fluorescence signal relative to the positive controls (RANTES alone).

THP-1 Whole Cell Radioligand Binding Assay

The cells were washed with PBS (phosphate buffered saline) and resuspended in binding buffer (10 mM HEPES pH 7.2, 1× HBSS (w/$Ca^{2+}$, $Mg^{2+}$) 0.5% BSA, 0.02% Na-azide) at $4 \times 10^6$ cells/ml (for 200, 000 cells/well). Cells were incubated with 0.1 to 0.2 nM [$^{125}$I]-labeled MIP-1α with or without unlabeled competitor (MIP-1α) or various concentrations of compounds for 60 minutes at room temperature. The assay was terminated by vacuum filtration through glass fiber filters (GF/B, Packard) which were presoaked in 0.3% polyethyleneimine. The filters were washed with wash buffer (10 mM HEPES, pH 7.2, 1 mM $CaCl_2$, 5 mM $MgCl_2$ 0.5M NaCl), dried and the amount of bound radioactivity was determined by scintillation counting.

Compounds of the invention have been shown to inhibit CCR1.

In some embodiments, the following compounds have inhibitory activity of less than 1 uM (referring to compounds in Table 1): 1, 2, 3, 4, 5, 6, 8, 9, 10, 11, 12, 13, 16, 18, 21, 22, 23, 24, 25, 26, 31, 32, 34, 37, 38, 39, 41, 42, 44, 45, 46, 48-53, 57, 58, 59, 61, 62, 64-68, 73-82, 84, 85, 86, 87, 88, 89, 93, 94, 95, 96, 97, 98, 99, 101, 102, 103, 104, 105, 106, 107, 108, 109, 110, 111, 112, 113, 114, 115, 116, 118, 119, 120, 121, 122, 123, 124, 125, 126, 127, 128, 129, 130, 131, 132, 133, 134, 135, 136, 137, 138, 140, 141, 146, 147, 148, 149, 150, 152, 153, 154, 155, 156, 157, 158, 160, 161, 162, 163, 165, 167, 171, 172, 173, 174, 176-197, and 198-204.

In some embodiments, the following compounds have inhibitory activity of less than 100 nm (referring to compounds in Table 1): 1, 3, 12, 16, 21, 23, 26, 34, 37, 61, 68, 79, 80, 81, 85, 86, 87, 93, 94, 95, 97, 101, 102, 105, 106, 107, 108, 109, 110, 111, 113, 115, 119, 121, 123, 125, 127, 129, 132, 137, 141, 146, 149, 150, 157, 161, 162, 165, 171, 172, 173, 174, 176-196, and 198-204.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A compound of formula II-A:

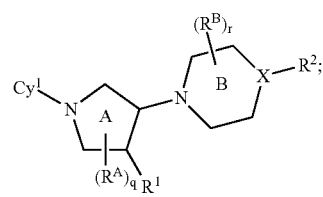

II-A or a pharmaceutically acceptable salt thereof, wherein:
a) $R^1$ is —OH or —OCO($C_1$-$C_6$ alkyl);
ring A is substituted with q occurrences of $R^A$;
q is 0, 1, or 2;
each occurrence of $R^A$ is independently halogen, an optionally substituted linear or branched $C_1$-$C_6$alkyl, or an optionally substituted $C_3$-$C_6$cycloalkyl ring;
b) ring B is substituted with r occurrences of —$R^B$;
r is 0, 1, or 2;
each occurrence of —$R^B$ is independently $C_1$-$C_3$alkyl;
c) $R^2$ is -$Cy^2$, or —T-$Cy^2$;
X is N;
T, when present, is —CO—, or —$CH_2$—;
$Cy^2$ is phenyl, or naphthyl;
wherein $Cy^2$ is substituted with 0, 1, or 2 occurrences of —$R^{6a}$;
each occurrence of —$R^{6a}$ is independently —Cl, —Br, —F, —CN, —$OCH_3$, —$OCH_2CH_3$, —$OCH_2CH_2CH_3$, —$CF_3$, —$CH_3$, —$CH_2CH_3$, —$CH_2CH_2CH_3$, —CH($CH_3$)$_2$, —C($CH_3$)$_3$, —COOH, —$COOCH_3$, or —$COOCH_2CH_3$;
d) $Cy^1$ is pyridyl, pyrimidinyl, pyrazinyl, pyridazinyl, 1,2,4-triazinyl, 1,3,5-triazinyl, 1,2,3-triazolyl, 1,2,4-triazolyl, imidazolyl, pyrazolyl, pyrrolyl, thiazolyl, isothiazolyl, thienyl, 1,3,4-thiadiazolyl, 1,2,4-thiadiazolyl, isoxazolyl, oxazolyl, furanyl, 1,3,4-oxadiazolyl, 1,2,4-oxadiazolyl, 1,3-dihydroimidazol-2-onyl, quinolinyl, isoquinolinyl, quinazolinyl, quinoxalinyl, [1,8]naphthyridinyl, 1,3-dihydro-benzoimidazol-2-on-1-yl, indolyl, benzo[c]isoxazolyl, benzofuranyl, benzothienyl, benzo[c]isothiazolyl, benzooxazol-2-yl, 5H-pyrrolo[3,2-d]pyrimidinyl, furo[3,2-d]pyrimidinyl, thieno[3,2-d]pyrimidinyl, indanyl, benzo[d]isothiazolyl, benzo[d]isoxazolyl, benzo[1,3]dioxolyl, benzothiazolyl, benzimidazolyl, indazolyl, purinyl, pyrido[2,3-d]pyrimidine, or pyrido[3,4-d]pyrimidine;

wherein $Cy^1$ is substituted with:

0, 1, or 2 occurrences of $—R^{10a}$;

each occurrence of $—R^{10a}$ is independently —Cl, —Br, —F, —NO₂, —CN, —OCH₃, —OCH₂CH₃, —OCH₂CH₂CH₃, —CF₃, —OCF₃, —CH₃, —CH₂CH₃, —CH₂CH₂CH₃, —C(CH₃)₃, —CH(CH₃)₂, t-Bu, —NHCOCH₃, —NHCONHCH₃, —SCH₃, —SCH₂CH₃, —SCH₂CH₂CH₃, —NH₂, —NHCH₃, —SO₂NH₂, —COON, —COOCH₃, —COOCH₂CH₃, —NHCH₃, —N(CH₃)₂, —NH(CH₂CH₃), —N(CH₂CH₃)₂, —OC(CH₃)₂CO₂H, —OCH₂CO₂H, —C(CH₃)₂OH, —CONH₂, —NHCONH₂, —NHCON(CH₃)₂, or —NHCOOCH₃; and 0 or 1 occurrence of $—R^{10b}$, $J-R^{10b}$, or $W-J-R^{10b}$, and $—R^{10b}$, $J-R^{10b}$, or $W-J-R^{10b}$ is morpholinyl, tetrazolyl,

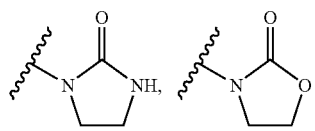

phenyl, benzyl, —NHCO(phenyl), —NHCO(benzyl), —NH(phenyl), —NHCH₂(phenyl), —NH(benzyl), —S(phenyl), —S(benzyl), —O(phenyl), or —O(benzyl), wherein the phenyl and benzyl groups are optionally substituted.

2. The compound of claim 1, wherein the compound has the structure of formula II-A-i:

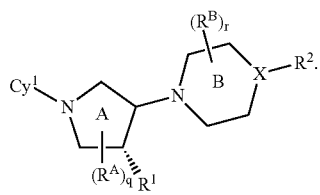

II-A-i

3. The compound of claim 1 or 2, wherein:
a) q is 0 or 1;
when q is 1, ring A has the structure:

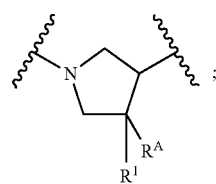

wherein $R^1$ is —OH, and $—R^A$ is —CH₃, CH₂CH₃, or F;
b) r is 0, 1, or 2, and $—R^B$ is methyl;
c) $Cy^2$ is phenyl; and
d) $Cy^1$ is:

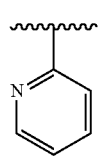
ii-a

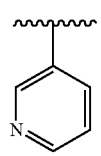
ii-b

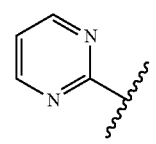
iii-a

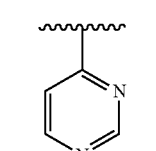
iii-b

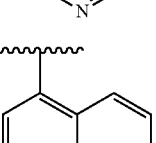
xxiv-a

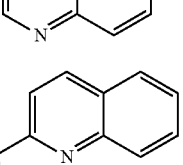
xxiv-b

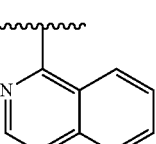
xxv-a

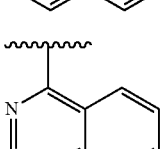
xxvi-a

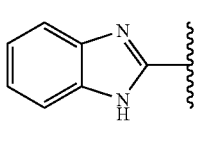
xLiv-a

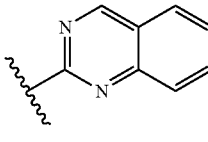
xLv-a

-continued

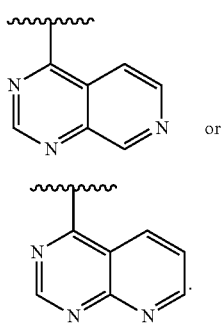

4. The compound of claim 3, wherein $R^1$ is —OH.
5. The compound of claim 3, wherein q is 0.
6. The compound of claim 3, wherein r is 0.
7. The compound of claim 3, wherein $Cy^2$ is substituted with 1 or 2 occurrences of —$R^{6a}$, and each —$R^{6a}$ is independently —Cl, —F, —$CF_3$, —$CH_3$, or —Br.
8. The compound of claim 3, wherein $Cy^2$ is substituted with 1 occurrence of —$R^{6a}$, and —$R^{6a}$ is —Cl.
9. The compound of claim 3, wherein $Cy^2$ is:

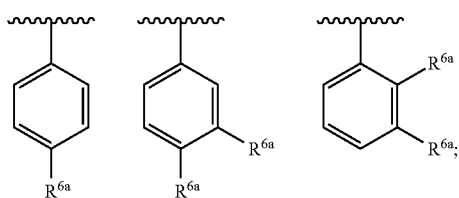

and each $R^{6a}$ is independently —Cl, —Br, —$CH_3$, —$CF_3$, or —F.
10. The compound of claim 3, wherein $Cy^2$ is phenyl substituted with 1 or 2 occurrences of —$R^{6a}$, and each —$R^{6a}$ is independently —Cl, —F, —$CF_3$, —$CH_3$, or —Br.
11. The compound of claim 3, wherein $Cy^2$ is phenyl substituted with 1 occurrence of —$R^{6a}$, and —$R^{6a}$ is —Cl.
12. The compound of claim 3, wherein $Cy_1$ is 2pyridyl (ii-a), pyrimidin-2-yl (iii-a), pyrimidin-4-yl (iii-b), quinolinyl (xxiv-a), or 4-quinaozlinyl (xxvi-a) 2-quinazolinyl (xLv-a), pyrido[2,3-d]pyrimidinyl (xLvi-a) or pyrido[3,4-d]pyrimidinyl (xLvii-a).
13. The compound of claim 3, wherein $Cy^1$ is 2-pyridyl (ii-a), pyrimidin-2-yl (iii-a), 4-quinazoline (xxvi-a) or 2-quinazolinyl (xLv-a).
14. The compound of claim 13, wherein $Cy^1$ is substituted with 1, 2, or 3 occurrences of $R^{10}a$, and each $R^{10a}$ is independently —Cl, —Br, —F, —$CH_3$, —$CF_3$, —$COOCH_3$, —$CONH_2$, —$NHCONH_2$, —$NHCOOCH_3$, —$NHCONHCH_3$, —$CONHCH_3$, —$C(CH_3)_2OH$, —$OCH_3$, —$OCH_2CH_3$, —CN, -tetrazole, —$NO_2$, —$N(CH_3)_2$, -or COOH.
15. The compound of claim 13, wherein $Cy^1$ is substituted with 0, 1, 2 or 3 occurrences of —$R^{10a}$, and 0 or 1 occurrences of —$R^{10a}$ each -$R^{10a}$ is independently —$COOCH_3$, —$CONH_2$, —$OCH_3$, —Cl, —Br, —F, or —$CF_3$, and —$R^{10b}$ is optionally substituted phenyl.
16. A pharmaceutical composition comprising a therapeutically effective amount of compound of claim 1, and a pharmaceutically acceptable carrier, adjuvant, or vehicle.
17. The composition of claim 16, comprising an additional therapeutic agent.

* * * * *